US006841154B2

(12) United States Patent
Foster et al.

(10) Patent No.: US 6,841,154 B2
(45) Date of Patent: Jan. 11, 2005

(54) CROSS-REACTIVE MONOCLONAL AND POLYCLONAL ANTIBODIES WHICH RECOGNIZE SURFACE PROTEINS FROM COAGULASE-NEGATIVE STAPHYLOCOCCI AND *STAPHYLOCOCCUS AUREUS*

(75) Inventors: Timothy Foster, Dublin (IE); Fiona Roche, Dublin (IE); Mark Pallen, Worcs (GB); Joseph M. Patti, Cumming, GA (US); Jeff T. Hutchins, Cumming, GA (US); Pietro Speziale, Pavia (IT)

(73) Assignees: Inhibitex, Inc., Alpharetta, GA (US); The Provost Fellows and Scholars of the College of the Holy and Undivided Trinity of Queen Elizabeth Near Dublin, Dublin (IE); Universita'degli Studi di Pavia, Pavia (IT)

( * ) Notice: Subject to any disclaimer, the term of this patent is extended or adjusted under 35 U.S.C. 154(b) by 0 days.

(21) Appl. No.: 10/172,502

(22) Filed: Jun. 17, 2002

(65) Prior Publication Data

US 2003/0185833 A1 Oct. 2, 2003

Related U.S. Application Data

(60) Provisional application No. 60/298,098, filed on Jun. 15, 2001.

(51) Int. Cl.[7] ............................................... A61K 39/40
(52) U.S. Cl. .............................. 424/165.1; 424/164.1; 530/387; 530/388.1; 530/388.15; 530/387.3; 530/387.9; 530/388.4
(58) Field of Search ........................... 424/165.1, 164.1; 530/387.1, 388.1, 388.15, 387.3, 387.9, 388.4

(56) References Cited

U.S. PATENT DOCUMENTS

| | | |
|---|---|---|
| 4,816,567 A | 3/1989 | Cabilly et al. |
| 5,175,096 A | 12/1992 | Hook et al. |
| 5,320,951 A | 6/1994 | Hook et al. |
| 5,416,021 A | 5/1995 | Hook et al. |
| 5,440,014 A | 8/1995 | Hook et al. |
| 5,571,514 A | 11/1996 | Hook et al. |
| 5,652,217 A | 7/1997 | Hook et al. |
| 5,707,702 A | 1/1998 | Brady, Jr. et al. |
| 5,789,549 A | 8/1998 | Hook et al. |
| 5,807,715 A | 9/1998 | Morrison et al. |
| 5,840,846 A | 11/1998 | Hook et al. |
| 5,851,794 A | 12/1998 | Guss et al. |
| 5,980,908 A | 11/1999 | Hook et al. |
| 5,981,216 A | 11/1999 | Kenten et al. |
| 6,008,341 A | 12/1999 | Foster et al. |
| 6,086,895 A | 7/2000 | Hook et al. |
| 6,177,084 B1 | 1/2001 | Foster et al. |
| 6,288,214 B1 | 9/2001 | Hook et al. |
| 6,294,177 B1 * | 9/2001 | Fattom .................... 424/243.1 |
| 6,331,415 B1 | 12/2001 | Cabilly et al. |

FOREIGN PATENT DOCUMENTS

| | | |
|---|---|---|
| EP | 0 519 596 A1 | 12/1992 |
| WO | WO 97/48727 | 12/1997 |
| WO | WO 00/12689 | 3/2000 |
| WO | WO 00/71585 | 11/2000 |

OTHER PUBLICATIONS

Kuroda et al. The Lancet. Apr. 2001. 357(9264):1225–1240.*

Foster et al., "Clumper factor B (ClfB), a new surface–located fibrinogen–binding adhesion of *Staplylococcus aureus*", EMBL–GenBank Submission, Aug. 3, 1998.

Cockayne et al., "Molecular Cloning of a 32–Kilodalton Lipoprotein Component of a Novel Iron–Regulated . . . ", Infection and Immunity, Aug. 1998, pp. 3767–3774.

McDevitt et al., "Molecular characterization of the clumping factor (fibrinogen receptor) of *Staphylococcus aureus*", Molecular Microbiology, 1994, 11(2) pp. 237–248.

McCrea et al., "The serine–aspartate repeat (Sdr) protein family in *Staphylococcus epidemidis*", Microbiology (2000), 146, pp. 1535–1546.

McCrea et al., "A Family of Putative Adherence Proteins Related to the Clumping Factor of *Staphylococcus aureus*", Abstracts of the General Meeting of the American Society for Microbiology (1998), vol. 98, p. 63.

Nilsson et al., "A Fibrinogen–Binding Protein of *Staphylococcus epidermidis*", Infection and Immunity, Jun. 1998, pp. 2666–2673.

Mazmanian et al., "Sortase–catalysed anchoring of surface proteins to the cell wall of *Staphylococcus aureus*", MicroReview, Molecular Microbiology (2001), 40(5), 1049–1057.

* cited by examiner

*Primary Examiner*—Jennifer E. Graser
(74) *Attorney, Agent, or Firm*—Stites & Harbison PLLC; B. Aaron Schulman

(57) ABSTRACT

Polyclonal and monoclonal antibodies which are cross-reactive to both coagulase-positive staphylococcus bacteria, such as *S. aureus* and to coagulase-negative bacteria, such as *S. epidermidis* and *S. hemolyticus*, are provided which can recognize surface proteins from both coagulase-positive and coagulase negative staph bacteria. The antibodies may be generated from surface proteins that have been isolated on the basis of characteristics that may be common between *S. aureus* and coagulase-negative staphylococci, and these recombinant surface proteins are used to generate the antibodies of the invention. There is also provided vaccines and methods which utilize these proteins and antibodies for the treatment or protection against a wide variety of staphylococcal infections.

11 Claims, 12 Drawing Sheets

|  | RESIDUES | PREDICTED MW | APPARENT MW |
|---|---|---|---|
| • RrkN 1 | 60-215 | 19 | 29 |
| • RrkN 2 | 60-437 | 45 | 48 |
| • DsqA 1 | 54-279 | 27 | 38 |
| • DsqA 2 | 54-533 | 58 | 62 |
| • KesK 1 | 55-335 | 34 | 47 |
| • KnkA | 39-210 | 20 | 27 |
| • KesK 2 | 329-591 | 31 | 40 |

CROSS-REACTIVE MONOCLONAL AND POLYCLONAL ANTIBODIES WHICH RECOGNIZE SURFACE PROTEINS FROM COAGULASE-NEGATIVE STAPHYLOCOCCI AND STAPHYLOCOCCUS AUREUS

CROSS REFERENCE TO RELATED APPLICATIONS

The present application claims the benefit of U.S. provisional application Ser. No. 60/298,098 filed Jun. 15, 2001.

FIELD OF THE INVENTION

The present invention relates in general to surface proteins from Staphylococcus aureus and their active regions such as their A domains which have homologue proteins on coagulase-negative Staphylococci such as S. epidermidis and S. hemolyticus as well as antibodies which recognize said proteins, and in particular to isolated monoclonal and polyclonal antibodies which recognize specific proteins from Staphylococcus aureus and coagulase-negative Staphylococci and which are cross-reactive against S. aureus and coagulase-negative Staphylococci and can thus be utilized in vaccines and methods useful for preventing or treating a wide variety of infections caused by staphylococcal bacteria.

BACKGROUND OF THE INVENTION

The successful colonization of the host is a process required for most microorganisms to cause infections in animals and humans. Microbial adhesion is the first crucial step in a series of events that can eventually lead to disease. Pathogenic microorganisms colonize the host by attaching to host tissues or serum conditioned implanted biomaterials, such as catheters, artificial joints, and vascular grafts, through specific adhesins present on the surface of the bacteria. MSCRAMM®s (Microbial Surface Components Recognizing Adhesive Matrix Molecules) are a family of cell surface adhesins that recognize and specifically bind to distinct components in the host's extracellular matrix. Once the bacteria have successfully adhered and colonized host tissues, their physiology is dramatically altered and damaging components such as toxins and proteolytic enzymes are secreted. Moreover, adherent bacteria often produce a biofilm and quickly become more resistant to the killing effect of most antibiotics.

S. aureus causes a spectrum of infections that range from cutaneous lesions such as wound infections, impetigo, and furuncles to life-threatening conditions that include pneumonia, septic arthritis, sepsis, endocarditis, and biomaterial related infections. S. aureus is known to express a repertoire of different MSCRAMMs that can act individually or in concert to facilitate microbial adhesion to specific host tissue components. In addition, another type of staphylococcus bacteria is identified as the coagulase-negative bacteria, including such species as S. epidermidis and S. hemolyticus which are also have been known to express MSCRAMMs, and which also are responsible for a wide range of bacterial infections and related diseases. In this regard, MSCRAMMs generally provide an excellent target for immunological attack by antibodies, both polyclonal and monoclonal antibodies.

However, because antibodies by nature are very specific and in the case of different types of Staphylococci, such as S. aureus on one hand (coagulase-positive) and S. epidermidis and S. hemolyticus on the other (coagulase-negative), it has still remained a significant problem to develop antibodies that exhibit cross-reactivity across the different types of bacteria. Such cross-reactive antibodies are particularly desirable because of their potential in immunizing human and animal patients and providing protection against infections caused by both types of Staphylococcal bacteria, namely coagulase-positive bacteria such as S. aureus and the coagulase-negative bacteria, such as S. epidermidis and S. hemolyticus. Such antibodies would thus be extremely useful in preventing or treating a wide variety of the infections caused by staphylococcal bacteria.

SUMMARY OF THE INVENTION

Accordingly, it is an object of the present invention to provide monoclonal antibodies that recognize MSCRAMM®'s from both coagulase-positive bacteria such as S. aureus as well as MSCRAMM®'s from coagulase-negative bacteria, such as S. epidermidis and S. hemolyticus.

It is also an object of the present invention to identify and isolate SCRAMM®'s from staphylococcal bacteria, as well as their active regions such as he A domain, which can be used to generate monoclonal and polyclonal antibodies hat will be cross-reactive against both coagulase-positive and coagulase-negative staphylococci.

It is still further an object of the present invention to provide isolated antibodies that can recognize the A domain of surface proteins such as the DgsK protein from coagulase-negative staphylococci and at the same time recognize surface proteins such as the SasA protein from Staphylococcus aureus.

It is yet another object of the present invention to utilize the isolated proteins, A domains and antibodies of the invention to produce vaccines useful in the treatment or prevention of staphylococcal infections, and to provide methods wherein the vaccines and antibodies of the invention are used to prevent or treat a staphylococcal infection.

These and other objects are provided by virtue of the present invention which comprises the identification and isolation of surface proteins from one type of staphylococcal bacteria, such as coagulase-negative or coagulase-positive staph, which can give rise to cross-reactive antibodies which can recognize surface proteins of both types of staph and which can thus be utilized in vaccines and methods of treating or preventing a wide range of staphylococcal infections. The present invention also relates to the generation of both polyclonal and monoclonal antibodies from these surface proteins and their use in preventing or treating staphylococcal infections.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

Figure 5A:
Figure 5A:
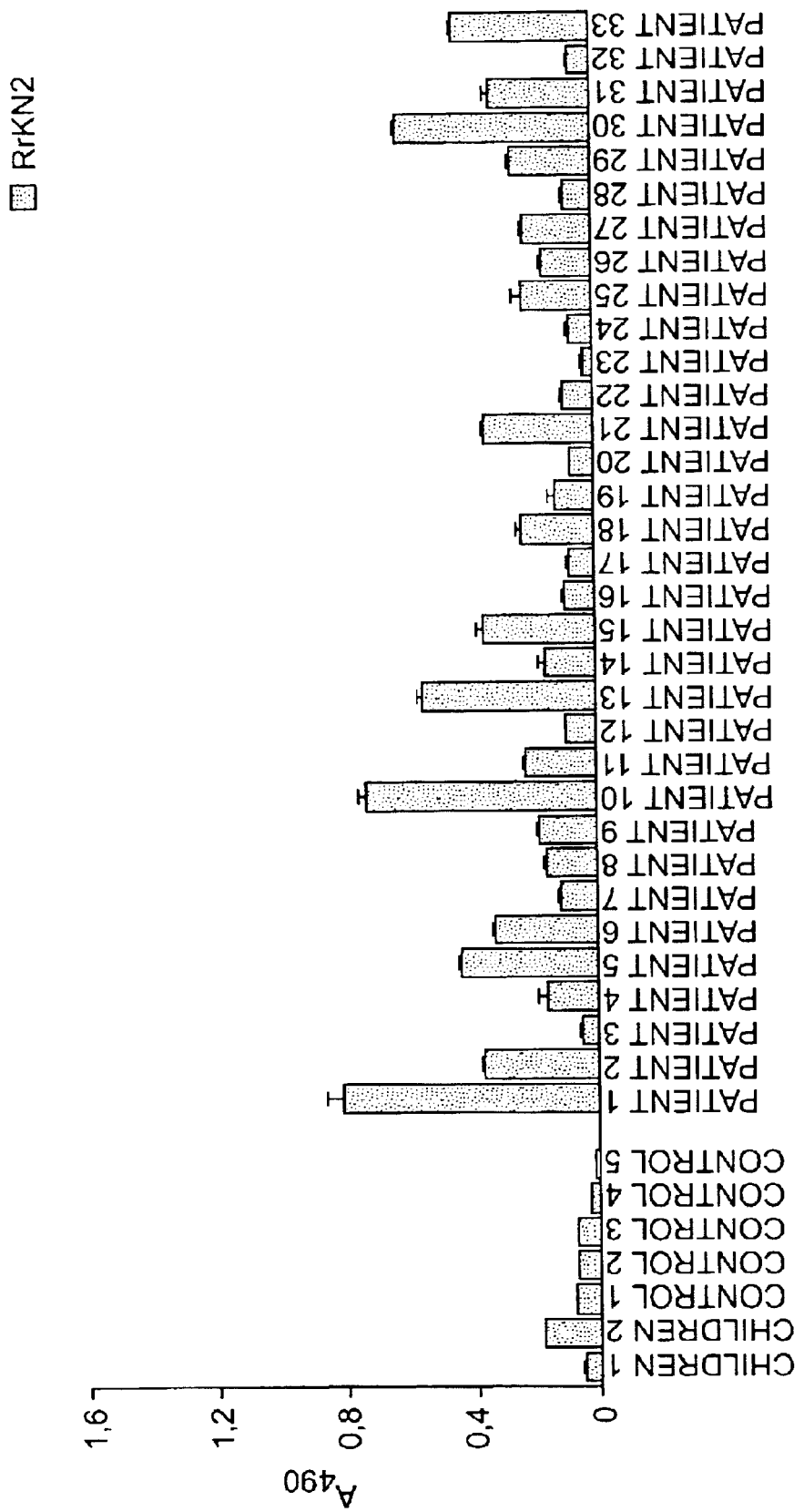
Figure 5B:
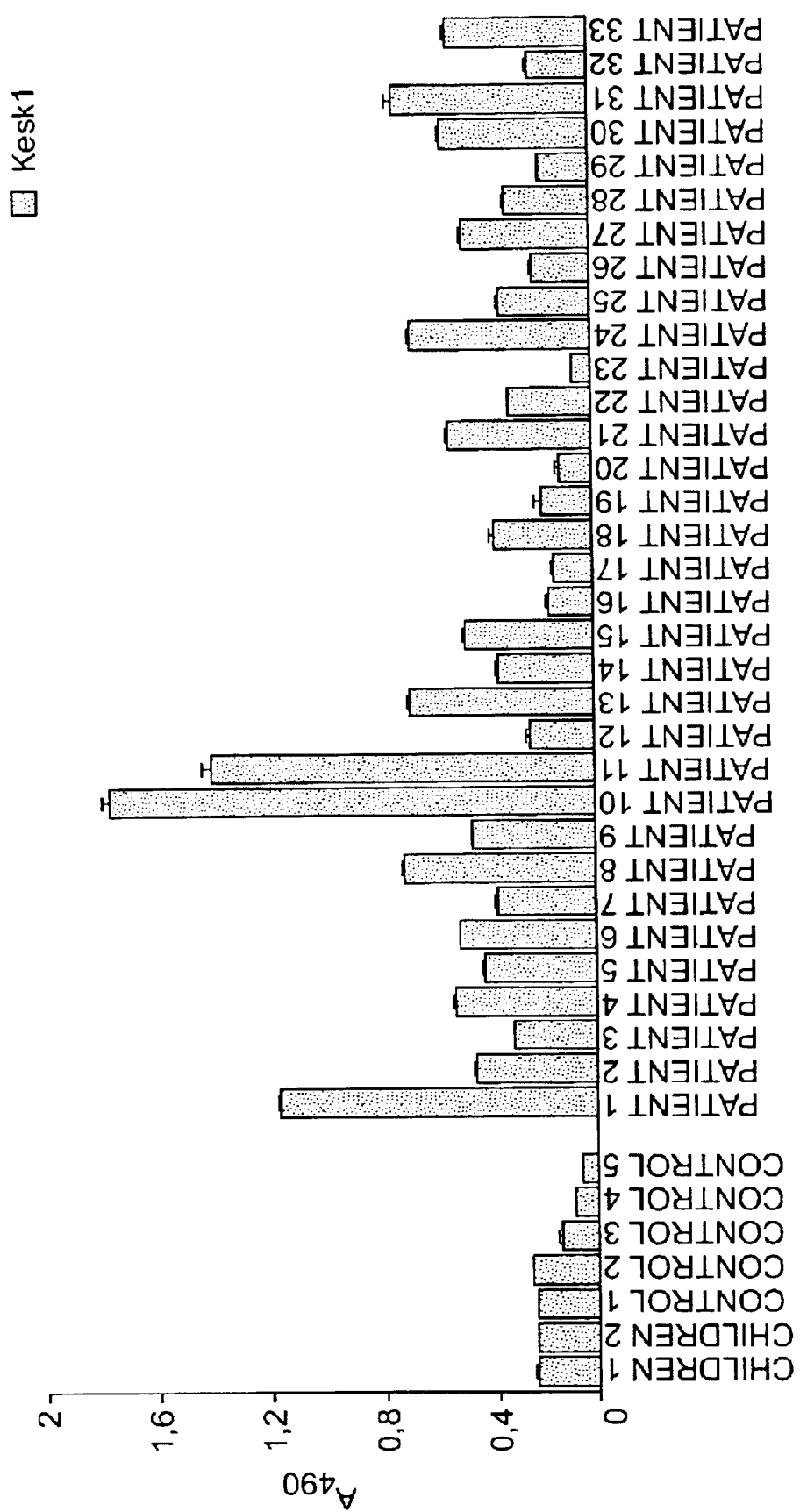
Figure 5B:
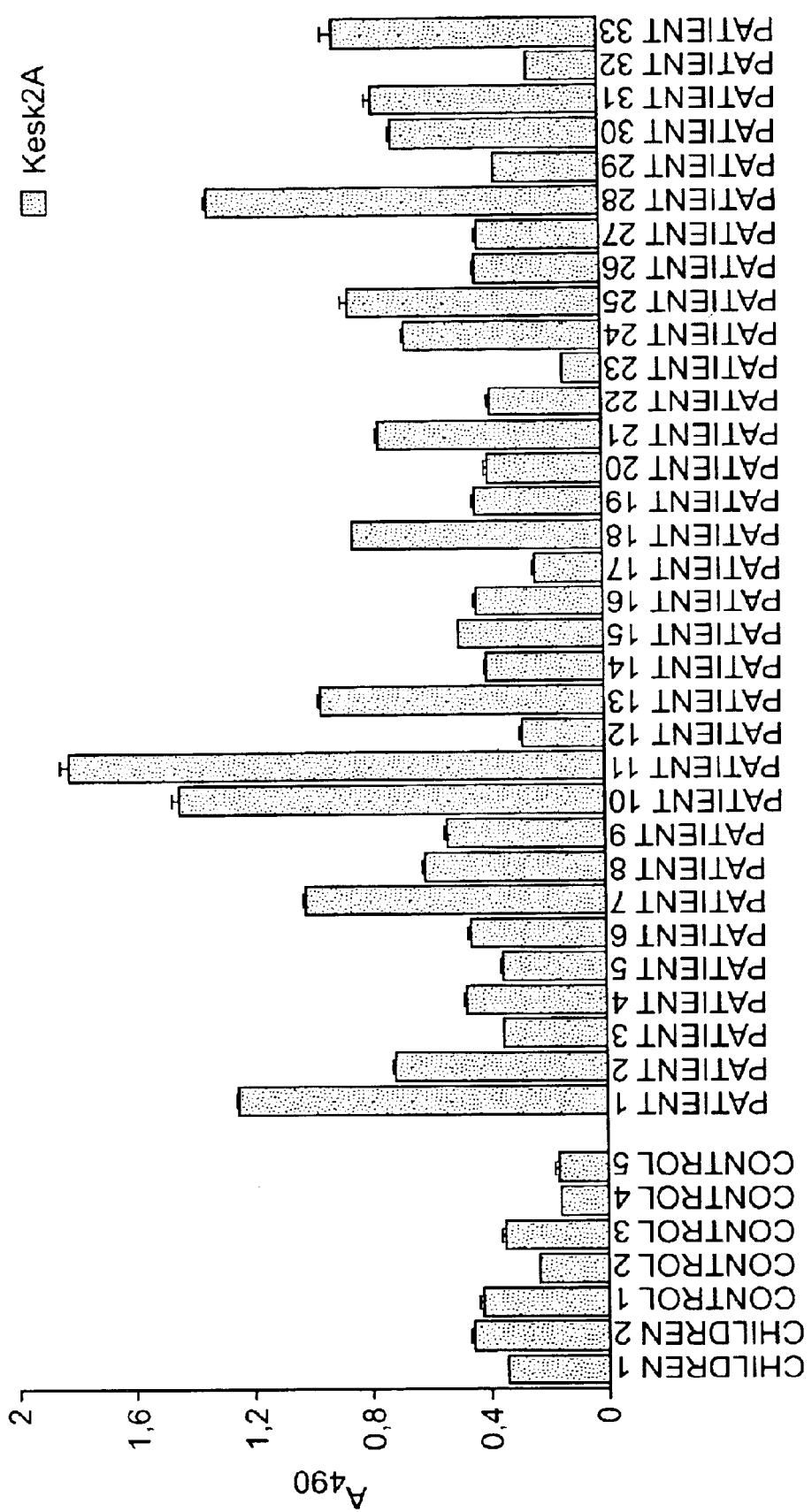
Figure 5C:
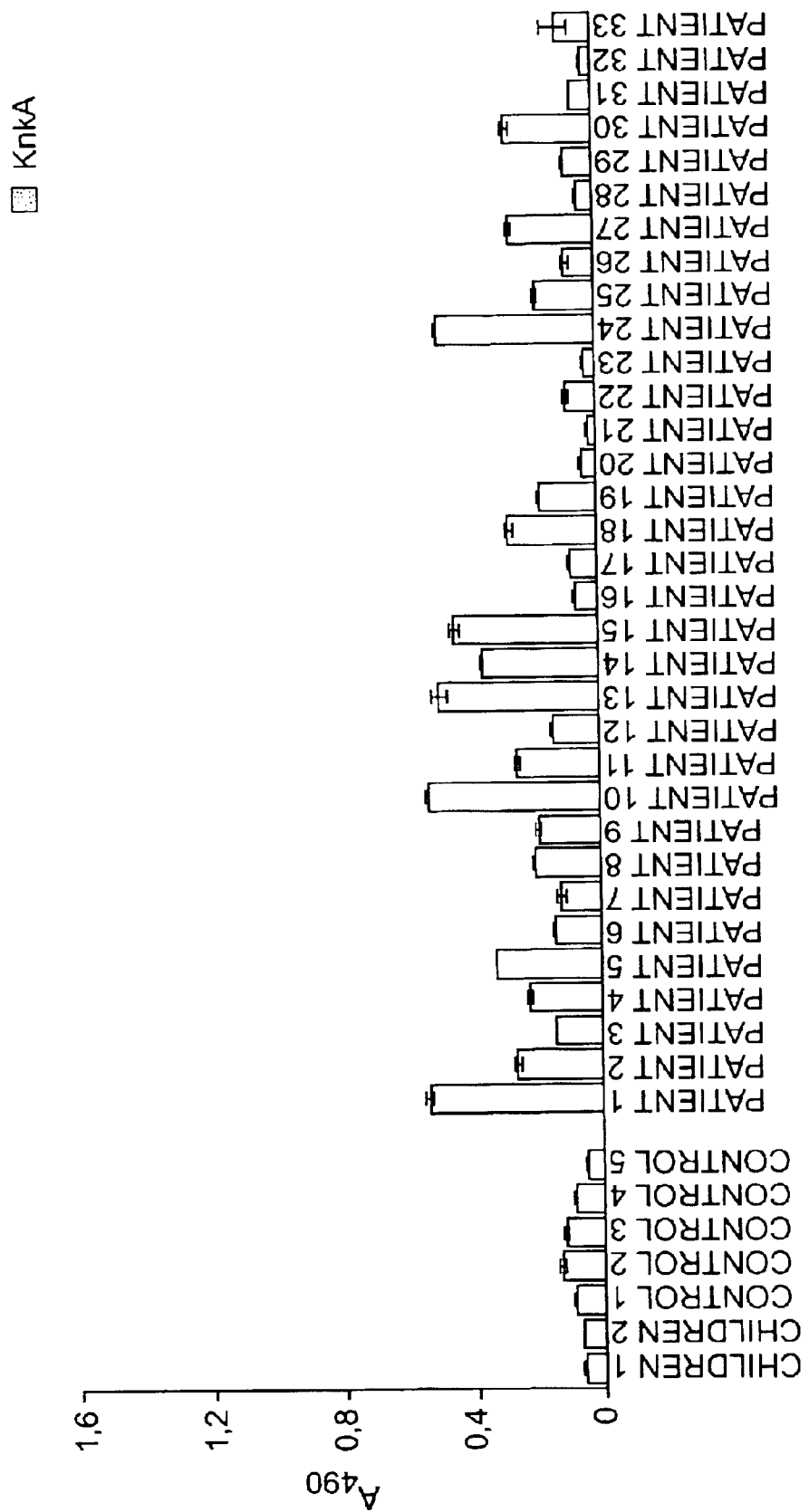
Figure 5D:
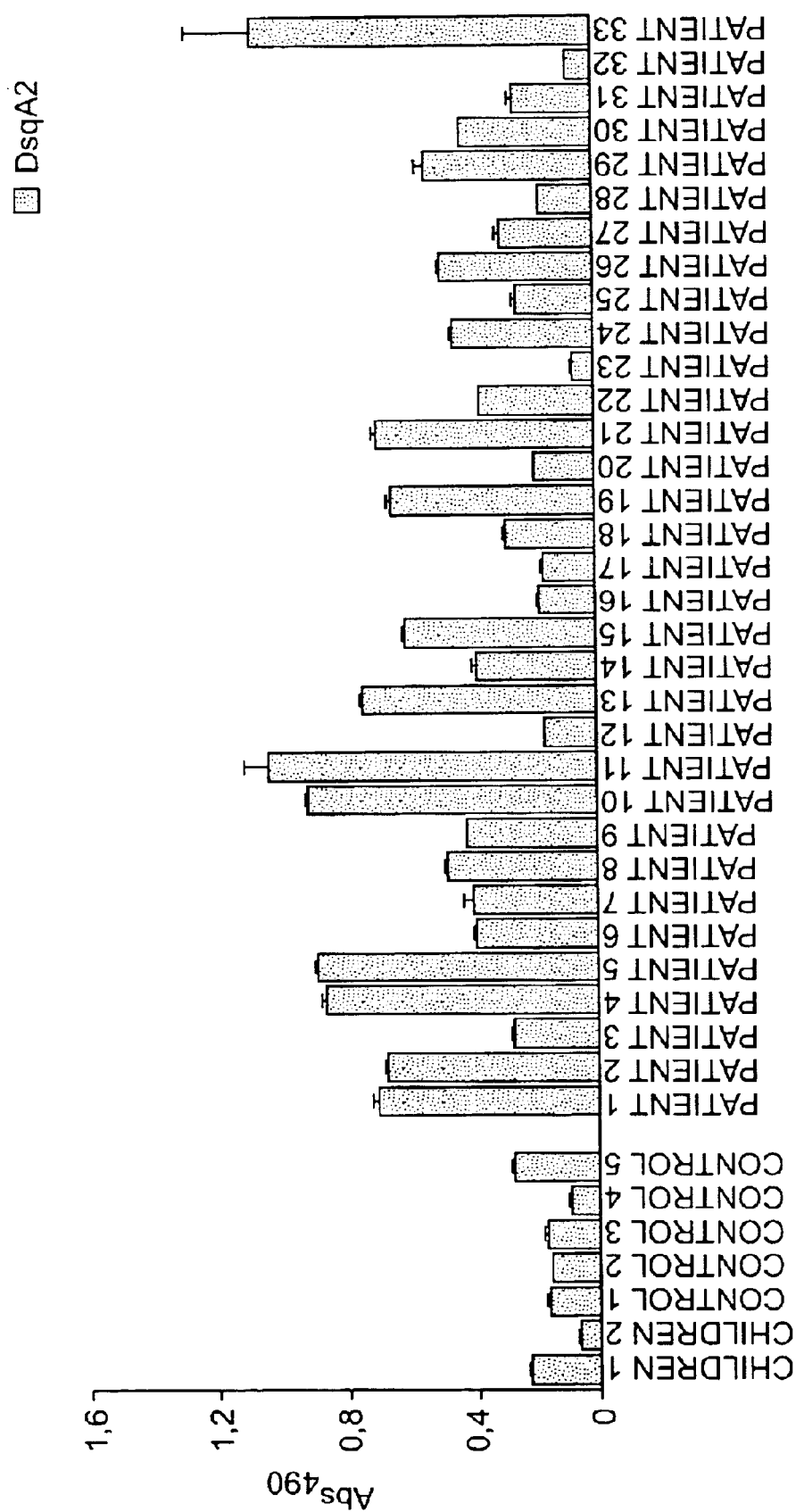

FIGS. 5A-5D representing the probing of recombinant LPXTG proteins in accordance with the present invention with convalescent sera examining in vivo expression, including RrKn and RrKN2 (FIG. 5A), Kesk1 and Kesk2A (FIG. 5B), KnkA (FIG. 5C) and DsqA2 (FIG. 5D).

Figure 6:
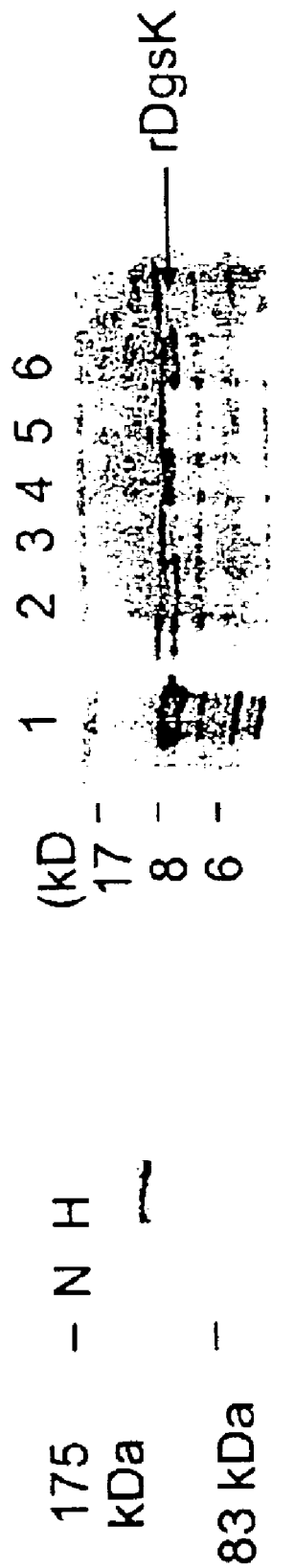

FIG. 6 shows a Western blot analysis demonstrating that rabbit polyclonal antibodies against *S. aureus* SasA cross-react with a protein released from the cell surface of *S. epidermidis* HB as well as the recombinant A-region from DsgK cloned from *S. epidermidis*.

DETAILED DESCRIPTION OF THE PREFERRED EMBODIMENTS

In accordance with the present invention, there are provided specific surface proteins from coagulase-positive staphylococcal bacteria, such as *S. aureus* as well as from coagulase-negative staph such as *S. epidermidis* and *S. hemolyticus*, including active fragments thereof such as the A domains of these proteins or other epitotic regions which can generate antibodies that recognize the whole protein. In accordance with the invention, the identification and isolation of candidate peptide sequences and proteins was carried out based on some of the common features of the MSCRAMM®s ((Microbial Surface Components Recognizing Adhesive Matrix Molecules) which are in most cases are covalently anchored to the cell wall peptidoglycan. These surface proteins had the following common features which were utilized in identifying and isolated the sequences of the present invention, namely: (i) an N-terminal signal peptide (approximately 40 residues in length) required for Sec-dependent secretion, (ii) a wall spanning domain either rich in proline and glycine residues or composed of serine and aspartate dipeptide repeats, (iii) an LPXTG motif required for covalent anchoring of the protein to the pentaglycine crossbridge in peptidoglycan, (iv) a hydrophobic membrane-spanning domain followed by (v) several positively charged residues.

In accordance with the invention, by exploiting the whole genome of *S. aureus* in light of the properties as set forth above, at least eight novel open reading frames encoding proteins with secretion and anchorage motifs indicative of MSCRAMMs were identified (i.e. bearing an N-terminal signal peptide and a C-terminal LPXTG motif followed by a hydrophobic domain and a positively charged tail). Table 1 illustrates the list of proteins identified including their distribution among *S. aureus* genomes, their protein size and C-terminal cell wall sorting sequence.

TABLE 1

| Name | Distribution | Size | C-terminus |
|---|---|---|---|
| EkeS | ENCSJM | 2189 aa | LPNTGSEEMDLPLKEL ALITGAALLARRRS KKEKES |
| DsqA | ENCSJM | ~1363–2283 aa | LPDTGDSIKQNGLLGG VMTLLVGLGLMKR KKKKDENDQDDSQA |
| KesK | ENCSJM | ~909 aa | LPKTGETTSSQSWWGL YALLGMLALFIPK FRKESK |

TABLE 1-continued

| Name | Distribution | Size | C-terminus |
|---|---|---|---|
| KrkN2 | ENCSJM (Cowan) | ~278 aa | LPKTGLTSVDNFISTV AFATLALLGSLSLLLF KRKESK |
| KrkN | ENCSJM | ~661 aa | LPQTGEESNKDMTLPL MALIALSSIVAFVLP RKRKN |
| RkaS | ENCSJM | ~801 aa | LPKTGTNQSSSPEAMF VLLAGIGLIATVRR RKAS |
| RrkN | NCSJM | 1629 aa | LPKTGLESTQKGLIFS SIIGIAGLMLLARRRK N |
| KnkA | NCSJM | 629 aa | LPKAGETIKEHWLPIS VIVGAMGVLMIWLS RRNKLKNKA |

Abbreviations: eMRSA-16; N, 8325; C, COL; S, MSSA; J, N315, M, Mu50. Six out of eight are conserved in all of the six staphylococcal genomes currently sequenced and the remaining two are present in 5/6 of these genomes.

In accordance with the invention, amino acid and nucleic acid sequences coding for the above proteins were obtained, and these were as follows: Ekes MRSA—SEQ ID NO:1 (DNA sequence); EkeS_MRSA—SEQ ID NO:2 (Protein sequence); DsqA (8325)—SEQ ID NO:3 (DNA sequence); DsqA (8325)—SEQ ID NO:4 (Protein sequence); KesK1 (8325)—SEQ ID NO:5 (DNA sequence); KesK1 (8325)—SEQ ID NO:6 (Protein sequence); KrkN2 (8325)—SEQ ID NO:7 (DNA sequence); KrkN2 (8325)—SEQ ID NO:8 (Protein sequence); KrkN (8325)—SEQ ID NO:9 (DNA sequence); KrkN (8325)—SEQ ID NO:10 (Protein sequence); RkaS (COL)—SEQ ID NO:11 (DNA sequence); RkaS (COL)—SEQ ID NO:12 (Protein sequence); RrkN (8325)—SEQ ID NO:13 (DNA sequence); RrkN (8325)—SEQ ID NO:14 (Protein sequence); KnkA (8325)—SEQ ID NO:15 (DNA sequence); KnkA (8325)—SEQ ID NO:16 (Protein sequence).

In accordance with the present invention, isolated antibodies may be generated from the above proteins or their active regions such as the A domain so as to be able to recognize said proteins and/or said domains. These antibodies may be either monoclonal or polyclonal. If polyclonal antibodies are desired, these may be generated in any of a number of conventional ways well known in the art. In a typical process, the desired surface protein or active region thereof may be injected into a suitable host animal, e.g., a mouse or rabbit, and after a suitable time period, antibodies may be isolated and recovered from the host animal. With regard to monoclonal antibodies, in accordance with the present invention, these may be produced in any number of suitable ways including, e.g., the well known method of Kohler and Milstein, Nature 256:495497 (1975), or other suitable ways known in the field, such as those methods disclosed in U.S. Pat. Nos. 6,331,415; 5,981,216; 5,807,715; and 4,816,567; Eur. Pat. App. 519,596; and PCT publication WO 00/71585, all of these patent publications incorporated herein by reference. These methods include their preparation as chimeric, humanized, or human monoclonal antibodies in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to the particular surface protein or its homologue from the different type of staph bacteria (i.e., coagulase negative or coagulase-positive), and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

As indicated above, antibodies to the isolated surface proteins and/or their active regions in accordance with the invention may be prepared in a number of suitable ways that would be well known in the art, such as the well-established Kohler and Milstein method described above which can be utilized to generate monoclonal antibodies. For example, in preliminary steps utilized in such a process, mice may be injected intraperitoneally once a week for a prolonged period with a purified recombinant MSCRAMM® in accordance with the invention or an active portion thereof, followed by a test of blood obtained from the immunized mice to determine reactivity to the purified protein. Following identification of mice reactive to the proteins, lymphocytes isolated from mouse spleens are fused to mouse myeloma cells to produce hybridomas positive for the antibodies against the surface proteins of the invention which are then isolated and cultured, following by purification and isotyping.

In order to generate monoclonal antibodies in accordance with the invention, it is preferred that these be generated using recombinantly prepared MSCRAMM®'s in accordance with the invention, and these recombinants may be generated and isolated using a number of standard methods well known in the art. For example, one such method employs the use of E. coli expression vector pQE-30 as an expression vector for cloning and expressing recombinant proteins and peptides. In one preferred method, using PCR, the A domain of the surface protein identified as DgsK or SasA was amplified from the sequences described above and subcloned into the E. coi expression vector PQE-30 (Qiagen), which allows for the expression of a recombinant fusion protein containing six histidine residues. This vector was subsequently transformed into E. coli strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size 0.45 μm) and the cell paste frozen at −80° C. Cells were lysed in 1× PBS (10 mL buffer/1 g of cell paste) using 2 passes through the French Press @ 1100 psi. Lysed cells were spun down at 17,000 rpm for 30 minutes to remove cell debris. Supernatant was passed over a 5-mL HiTrap Chelating (Pharmacia) column charged with 0.1 M $NiCl_2$. After loading, the column was washed with 5 column volumes of 10 mM Tris, pH 8.0, 100 mM NaCl (Buffer A). Protein was eluted using a 0–100% gradient of 10 mM Tris, pH 8.0, 100 mM NaCl, 200 mM imidazole (Buffer B) over 30 column volumes. SdrGN1N2N3 or SdrGN2N3 eluted at ~13% Buffer B (~26 mM imidazole). Absorbance at 280 nm was monitored. Fractions containing SdrGN1N2N3 or SdrGN2N3 were dialyzed in 1× PBS.

Next, each protein was then put through an endotoxin removal protocol. Buffers used during this protocol were made endotoxin free by passing over a 5-mL Mono-Q sepharose (Pharmacia) column. Protein was divided evenly between 4×15mL tubes. The volume of each tube was brought to 9 mL with Buffer A. 1 mL of 10% Triton X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1× PBS. The purified product was analyzed for concentration, purity and endotoxin level before administration into the mice.

In the preferred process, monoclonal antibodies in accordance with the present invention may be prepared from the recombinant proteins identified above in the following manner. In this process, E. coli expressed and purified recombinant SasA and DsgK proteins were used to generate a panel of murine monoclonal antibodies while the mouse sera was used as a source of polyclonal antibodies. Briefly, a group of Balb/C or SJL mice received a series of subcutaneous immunizations of 1–10 mg of protein in solution or mixed with adjuvant as described below in Table 2.

TABLE 2

| | Immunization Schemes | | | |
|---|---|---|---|---|
| | Day | Amount (μg) | Route | Adjuvant |
| RIMMS Injection | | | | |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection | | | | |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against MSCRAMM® proteins or on whole cells (S. epidermidis and S. aureus). Three days after the final boost, the spleens or lymph nodes were removed, teased into a single cell suspension and the lymphocytes harvested. Lymphocytes were then fused to a P3X63Ag8.653 myeloma cell line (ATCC #CRL-1580). Cell fusion, subsequent plating and feeding were performed according to the Production of Monoclonal Antibodies protocol from Current Protocols in Immunology (Chapter 2, Unit 2.), incorporated herein by reference.

Any clones that were generated from the fusion were then screened for specific anti-SasA antibody production using a standard ELISA assay. Positive clones were expanded and tested further for activity in a whole bacterial cell binding assay by flow cytometry and SasA binding by Biacore analysis. Throughout the Biacore analysis, the flow rate remained constant at 10 ml/min. Prior to the SasA or DgsK injection, test antibody was adsorbed to the chip via RAM-Fc binding. At time 0, SasA or DgsK at a concentration of 30 mg/ml was injected over the chip for 3 min followed by 2 minutes of dissociation. This phase of the analysis measured the relative association and disassociation kinetics of the Mab/SasA or DgsK interaction.

Next, the antibodies prepared as set forth above were tested for binding to whole bacteria. In these tests, bacterial samples S. aureus Newman, S. aureus 67-0, S. aureus 397 (Sal6), S. aureus Wood, S. aureus 8325-4, methicillin resistant S. aureus MRSA 16, S. epidermidis ATCC 35984, S. epidermidis HB, S. epidermidis CN-899 and S. haemolyticus ATCC 43253 were collected, washed and incubated with Mab or PBS alone (control) at a concentration of 2 µg/ml after blocking with rabbit IgG (50 mg/ml). Following incubation with antibody, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured. These data indicate that antibodies against S. aureus SasA were able to recognize a homologous protein on the surface of coagulase-negative staphylococci. The data support Western blot analysis demonstrating that rabbit polyclonal antibodies against S. aureus SasA cross-react with a protein released from the cell surface of S. epidermidis HB as well as the recombinant A-region from DsgK cloned from S. epidermidis (see FIG. 6 and Table 3 below).

in this art. Suitable methods of administering any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol. Additional forms of antibody compositions, and other information concerning compositions, vaccines, methods and applications with regard to other MSCRAMM®s will generally also be applicable to the present invention involving the aforementioned MSCRAMM®s and their active regions and antibodies thereto, and these other MSCRAMM®s are disclosed, for example, in U.S. Pat. Nos. 5,175,096; 5,320,951; 5,416,021; 5,440,014; 5,571,514; 5,652,217; 5,707,702; 5,789,549; 5,840,846; 5,980,908; 6,086,895; 6,008,341; 6,177,084; 5,851,794 and 6,288,214; all of these patents incorporated herein by reference.

TABLE 3

| | | | | | | | | | |
|---|---|---|---|---|---|---|---|---|---|
| | | | | Polyclonal Sera Reactivity | | | | | |
| | Newman | 67-0 | 397 (SAL 6) | Wood 46 | 8325-4 | MRSA 16 | ATCC 35984 | HB | CN-899 | ATCC 43253 |
| Normal Mouse Sera | – | – | – | – | – | – | – | – | – | – |
| Mouse anti-SasA | + | + | +/– | – | + | + | + | + | + | + |

Although production of antibodies using recombinant forms of the surface proteins of the present invention is preferred, antibodies may be generated from natural isolated and purified versions of these proteins or their active regions such as the A domain, and monoclonal or polyclonal antibodies can be generated using these proteins or active regions in the same manner as described above to obtain such antibodies. Still other conventional ways are available to generate the antibodies of the present invention using recombinant or natural purified proteins or their active regions, as would be recognized by one skilled in the art.

As would be recognized by one skilled in the art, the antibodies of the present invention may also be formed into suitable pharmaceutical compositions for administration to a human or animal patient in order to treat or prevent an infection caused by staphylococcal bacteria. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill The antibody compositions of the present invention may also be administered with a suitable adjuvant in an amount effective to enhance the immunogenic response. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Still other chemically defined preparations such as muramyl dipeptide, monophosphoryl lipid A, phospholipid conjugates such as those described by Goodman-Snitkoff et al. J. Immunol. 147:410–415 (1991) and incorporated by reference herein, encapsulation of the conjugate within a proteoliposome as described by Miller et al., J. Exp. Med. 176:1739–1744 (1992) and incorporated by reference herein, and encapsulation of the protein in lipid vesicles such as Novasome™ lipid vesicles (Micro Vascular Systems, Inc., Nashua, NH) may also be useful.

In any event, the antibody compositions of the present invention which recognize the proteins or their active regions as set forth above will be useful in methods of preventing or treating staphylococcal infection, and in inhibiting binding of staphylococcal bacteria to host tissue and/or cells. In accordance with the present invention, methods are provided for preventing or treating a staphylococcal infection which comprise administering an effective amount of an antibody to the surface proteins as set forth herein or their active subregions so as to treat or prevent a staphylococcal infection. In addition, these monoclonal antibodies will be useful in impairing the binding of staphylococcal bacteria to host cells Accordingly, in accordance with the invention, administration of the antibodies of the present invention in any of the conventional ways described above (e.g., topical, parenteral, intramuscular, etc.), and will thus provide an extremely useful method of treating or preventing staphylococcal infections in human or animal patients when an effective amount of the antibody compositions are administered to a human or animal patient. By effective amount is meant that level of use, such as of an antibody titer, that will be sufficient to either prevent adherence of the bacteria, to inhibit binding of staph bacteria to host cells and thus be useful in the treatment or prevention of a staph infection. As would be recognized by one of ordinary skill in this art, the level of antibody titer needed to be effective in treating or preventing staphylococcal infection will vary depending on the nature and condition of the patient, and/or the severity of the preexisting staphylococcal infection.

In addition to use in methods or treating or preventing a staphylococcal infection, the antibodies of the invention may also be used for the specific detection of staphylococcal proteins, or as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies to the surface proteins specified above, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. In the present case, antibodies to the surface proteins or their active regions as referred to above can be generated, isolated and/or purified, and then used to treat or protect against staphylococcal infection.

Any of the above described antibodies may be labeled directly with a detectable label for identification and quantification of staph bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

In accordance with the present invention, there are also provided vaccines for either active or passive immunization designed to treat or protect against staphylococcal infections, and these vaccines may be prepared from the surface proteins or their active regions as set forth above using a number of the conventional vaccine preparation methods well known in this field. In the typical vaccine, an immunogenic amount of a suitable surface protein or active fragment thereof is combined with a suitable pharmaceutically acceptable vehicle, carrier or excipient, and an amount of this vaccine effective to immunize a human or animal patent may be administered as appropriate. By immunogenic amount it would be understood by one of ordinary skill in this art that this refers to any amount of the protein or active fragment or subregion thereof which is able to raise an immunogenic response in the human or animal patient.

In addition to active vaccines wherein antibodies are generated in the patient by virtue of the introduction or administration of an immunogenic amount of a protein or active fragment in accordance with the present invention, the isolated antibodies of the present invention, or active fragments thereof, may also be utilized in the development of vaccines for passive immunization against staph infections. In such a case, the antibody compositions as described above, namely an effective amount of the antibody and a pharmaceutically acceptable vehicle, carrier or excipient, may be administered as appropriate to a human or animal patient.

Accordingly, in accordance with the invention, the proteins or active fragments thereof may be utilized as active vaccines, and the antibodies of the invention may be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

In addition, in certain cases, the antibodies of the present invention may be modified as necessary so that, when necessary, they become less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., Nature 321:522–525 (1986) or Tempest et al. Biotechnology 9:266–273 (1991) or"veneered" by changing the surface exposed murine framework residues in the immunoglobulin variable regions to mimic a homologous human framework counterpart as described, e.g., by Padlan, Molecular Imm. 28:489–498 (1991), these references incorporated herein by reference. Even further, when so desired, the monoclonal antibodies of the present invention may be administered in conjunction with a suitable antibiotic to further enhance the ability of the present compositions to fight bacterial infections when necessary.

In addition to treating human or animal patients, the present compositions may also be used to halt or prevent infection of a medical device or other biomaterials such as an implant. Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or active fragment, or pharmaceutical composition derived therefrom, to a surface of the device, preferably an outer surface that would be exposed to streptococcal bacterial infection. The surface of the device need not be entirely covered by the protein, antibody or active fragment.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may also contain stabilizers or pharmaceutically acceptable preservatives, such as thimerosal (ethyl(2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to one skilled in the art, such as immunofluorescence microscopy using procedures such as those described by Warren et al. (*Mol. Cell. Biol.*, 7: 1326–1337, 1987).

As indicated above, the monoclonal antibodies of the present invention, or active portions or fragments thereof, are particularly useful for interfering with the initial physical interaction between a staphylococcal pathogen responsible for infection and a mammalian host, and this interference with the physical interaction may be useful both in treating patients and in preventing or reducing bacteria infection on in-dwelling medical devices to make them safer for use.

In another embodiment of the present invention, a kit which may be useful in isolating and identifying staphylococcal bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the surface proteins or the antibodies of the invention. In general, these kits may contain an antibody in accordance with the invention and means to identify binding of that antibody when a sample from a patient is introduced to the antibody. For example, a suitable immunodetection reagent may comprise an appropriate detectable signal or label, such as a biotin or enzyme that produces a detectable color, etc., which may be linked to the antibody or utilized in other suitable ways so as to provide a detectable result when the antibody binds to the antigen.

In short, the antibodies of the present invention which recognize and bind to the surface proteins of the invention, or active fragments thereof, will thus be useful in treating a wide variety of staphylococcal infections in human and animal patients and in medical or other in-dwelling devices. In accordance with the invention, because of the nature of these proteins and the fact that they contain epitopes in common with proteins of the other type of staphylococcal bacteria, i.e., a protein from a coagulase-negative staph will raise antibodies that recognize a homologous protein from *S. aureus* and vice versa, the antibodies of the invention will exhibit cross-reactivity and should be effective against a broad range of staphylococcal infections. Accordingly, the present invention provides methods and compositions for improved methods of treating or protecting against a wide range of staphylococcal infections.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation and Sequencing of MSCRAMM's from S. Aureus

Staphylococcus aureus is known to express a class of surface-associated proteins which play important roles in pathogenicity by allowing bacteria to avoid host defenses and by acting as adhesins. These proteins are known as MSCRAMMs (Microbial Surface Components Recognizing Adhesive Matrix Molecules) and in most cases are covalently anchored to the cell wall peptidoglycan. They have several common features: (i) an N-terminal signal peptide (approximately 40 residues in length) required for Sec-dependent secretion, (ii) a wall spanning domain either rich in proline and glycine residues or composed of serine and aspartate dipeptide repeats, (iii) an LPXTG motif required for covalent anchoring of the protein to the pentaglycine crossbridge in peptidoglycan, (iv) a hydrophobic membrane-spanning domain followed by (v) several positively charged residues.

By exploiting the whole genome sequences of S. aureus, eight novel open reading frames encoding proteins with secretion and anchorage motifs indicative of MSCRAMMs were identified (i.e. bearing an N-terminal signal peptide and a C-terminal LPXTG motif followed by a hydrophobic domain and a positively charged tail). The following Table illustrates the list of proteins identified including their distribution among S. aureus genomes, their protein size and C-terminal cell wall sorting sequence.

| Name | Distribution | Size | C-terminus |
| --- | --- | --- | --- |
| EkeS | ENCSJM | 2189 aa | LPNTGSEEMDLPLKEL ALITGAALLARRRS KKEKES |
| DsqA | ENCSJM | ~1363–2283 aa | LPDTGDSIKQNGLLGG VMTLLVGLGLMKR KKKKDENDQDDSQA |
| KesK | ENCSJM | ~909 aa | LPKTGETTSSQSWWGL YALLGMLALFIPK FRKESK |
| KrkN2 | ENCSJM (Cowan) | ~278 aa | LPKTGLTSVDNFISTV AFATLALLGSLSLLLF KRKESK |
| KrkN | ENCSJM | ~661 aa | LPQTGEESNKDMTLPL MALIALSSIVAFVLP RKRKN |
| RkaS | ENCSJM | ~801 aa | LPKTGTNQSSSPEAMF VLLAGIGLIATVRR RKAS |
| RrkN | NCSJM | 1629 aa | LPKTGLESTQKGLIFS SIIGIAGLMLLARRRK N |
| KnkA | NCSJM | 629 aa | LPKAGETIKEHWLPIS VIVGAMGVLMIWLS RRNKLKNKA |

Abbreviations: eMRSA-16; N, 8325; C, COL; S, MSSA; J, N315, M, Mu50. Six out of eight are conserved in all of the six staphylococcal genomes currently sequenced and the remaining two are present in 5/6 of these genomes.

The following is a list of the DNA and protein sequences:
Ekes MRSA (SEQ ID NO:1)

acaacacagcagagaatagacaaccag-
gaggaaaacgaaatgaatttgttaaagaaaaataaatatagtattag
aaaatataaagtagggatattctc-
tactttaatcgggacagttattactttcaaacccaaatggtgcacaagctttaac
tacggatcataatgtgcaaggtggt-
tcaaatcaagcattacctggcaactcacaaaatacaaatgccgatactaatc gaga-
catagtaaatgattcgcaaaatactc-
ctaatgcacatgcaacagacaatacatcaacaaatcaagcattgac
taatcatcaaaacgttgatgtggcaaat-
caagtcgggcctgctccaatacagcctagcgcgtcgcctgcgcaaaata
ataataattctaatgctaattcaacag-
caacagagccagcggcgaatacaaataataatttagcatcaaataacaat acat-
taaacgtgcctaataatacagataa-
caatgattcagcgcgtcatctgactttaaaagaaattcaagaagatgtt
cgtcattcgtctgataagccagagt-
tagttgcgattgctgaagaagcatctaatagaccgaaaagagaagcagac
gtgctgcgccaacagatcctaatgcaa-
caccagcagatccaacggctacaccagcagatccaacggcaggaaat ggtagt-
gcaccagttgcaattacagcgccata-
cacgccaacaactgatcccaatgccaataatataggacaaaatg
cacctaacgaagtgctttcatttgat-
gataacaacattagaccaagtacgaaccgttctgtgcctacagtaactgttgtt
gataatttaccaggctacacactgat-
taatggtggtaaagtaggggtgtttagtcatgcaatggtaagaacgagcatgt
ttgattcaggagatgccaagaactat-
caagcgcaaggcaatgtaattgcattgggtcgtattagaggaaatgataca aat-
gatcatggcgatmaatggtatc-
gagaaaacattaacagtaaatccgaattctgaattaatctttgaatttaatact
atgactactaaaaactatcaaggtatga-
caaatttaatcattaaaaatgctgataacgatactgttattggtgaaaaag tagttgct-
tatggtccgatttggcgcttattaaaag-
tacctgaaaatgttagtcatctaaaaattcaatttgtacctaaaaat
gacgcaataacagatgcacgtggtatt-
tatcaattacgagatggatataaatactatgactttgtagactcaatcggtct tcat-
tctgggtcacatgtctatgttgaaa-
gacgtacaatggagccaacagcaacaaataataaagaatttacagttac
aacgtcattaaagaataatgg-
taactttggcgcttcattcaatacagatgattttgtatataaaattcaattacctgaaggt
gttgaatatgtaaataattcattgac-
taaagattttcctagcggtaattcaggtgttgatattaatgatatgaatgtgacgta
tgacgcagcaaatcgaattattacaat-
taaaagtactggtggaggtacagggaattcgccggcacgactaatgcctg
ataaaatattggatttgaagtataagc-
tacgtgtgaacaatgtgccaacaccaagaacagtaacatttaacgatacat taacg-
tataaaacatattcacaagattt-
tataattcacctgctgaaagtcatactgtaagtacaaatccatatacaattg
atatcatcatgaataaagacgcattg-
caagccgaagtcgatagacgaattcaacaagcggattatacatttgcatcat
tagatattttaatgatcttaaaa-
gacgcgcacaaacaattttagatgaaaaccgtaacaatgtacctttaaacaaaag
agtttctcaagcagatatcgattcatt-
agcaaatcagatgcaacatacgttaattcgcagtgttgacgctgaaaatgcc
gttaatagaaaagttgatgacatggaa-
gatttagttaaccaaaatgatgaactgacagatgaagaaaaacaagca gcgattcaagtcatcgaggaacataaaat-
gaaattaftgggaatattggtgaccaaacgactgatgatggcgttact
agaattaaagatcaaggtatacagactt-
taagtggagacactgcaacaccagttgttaaaccaaatgctaaacaag ctatacgt-
gataaagcagcgaaacaaagagaaat-
tatcaatcacacgccagatgctactcaagatgaaattcaag
atgcattaaatcaattaacaacggat-
gaaacagatgctattgataatgttacgaatgctactaccaatgctgatgttga
aacagctaaaataatggtattaata-
caattggtgcagttgcgccacaagtgacacacaaacaagctgcaagaga
tgcaattaatcaagcgacagcaac-
gaaacgacaacaataaatagcaatagagaagcaacacaagaagaga aaaatg-
cagcattgaatgaattaacgcaagccac-
gaaccacgcattagaacaaatcaatcaagcgacaaccaat
gatgatgtagatactgccaaaggtgatg-
gtctgaatgccattaatcctattgcgcctgtaactgttgtcaagcaagcag caa-
gagatgccgtatcacatgatgaacaa-
cagcatatcgcagagatcaatgcaaatcctgatgcgactcaagaag
aaagacaagcagcaatagagaaag-
taaatgctgctgtagctgtgcgaatactaatatataaatgctaataccaat gctgat-
gttgagcaagtaaagacaaatgcaat-
tcaaggtatacaagccattgaaccagctacaaaggttaaaaca
gatgctaaaaacgctattgatcaaagt-
gcggaaacgcaacataatgcgatataataataatgatgcgaccttaga agagcaa-
caagcagcacaacaattgcttgat-
caagctgtagccacagcgaagcaaaatattaatgcagcagata
cgaatcaagaagttgcacaagcaaaa-
gatcagggcacacaaaatatagttgtgattcaaccggcaacacaagtta aaacg-
gatgcacgcaatgctgtaaat-
gaaaaagcgcgagaggcgataacaaatatcaatgctacacctggcgcg
actcgagaagagaaacaagaagc-
gataaatcgtgtcaatacacttaaaaatagagcattaaatgatattggtgtga cgtc-
tactactgcgatggtcaatagtatta-
gagacgatgcagtcaatcaaatcggtgcagttcaaccgcatgtaacga
agaaacaaactgctacaggtgtat-
taacggacttagcaactgcaaaaaaacaagaaattaatcaaatacaaatg caac-
cactgaagaaaagcaagtagcattaaat-
caagtagaccaagatttagcaacggcaattaataattaaatc
aagctgatactaatgcagaagtagat-
caagcacaacaattaggtacaaaagcaattaatgcgattcagccaaatat
tgtaaaaaaacctgcagcattagca-
caaaccaatcagcaftatagtgctaaattagttgaaatcaatgctacaccag atg-
caacagatgatgagaaaaatgctgcgat-
caatactttaaatcaagacagacaacaagctattgaaagtattaa
acaagcaaataacaaatgcggaagtagac-
caagctgcgacagtggcagagaataatatcgatgctgttcaagttga cgttg-
taaaaaacaagcagcgcgagataaaat-
cactgctgaagtagcgaagcgtattgaagcggttaaacaaa
cacctaatgcaactgacgaagaaaag-
caggctgcagftaatcaaatcaatcaacttaaagatcaagcgtttaatca aattaat-
caaaaccaaacaaatgatcaggtagacg-
caactacaaatcaagcgattaatgctatagataatgttgaa
gctgaagtagtaattaaaccaaag-
gcaattgcagatattgaaaaagctgttaaagaaaagcaacagcaaattgat aat-
agtcttgattaacagataatgagaaa-
gaagttgctttacaagcattagctaaagaaaaagaaaaagcacttg
cagctattgaccaagctcaaacgaat-
agtcaggtgaatcaagcggcaacaaatggtgtatcagcgattaaaattatt caac-
ctgaaacaaaaaftaaaccagcag-
cacgtgaaaaaatcaatcaaaaagcgaatgaattacgtgcgcaaa
ttaatcaagataaagaagcgacagca-
gaagaaagcaagcggcgttagataaaatcaatgatttagttgctaaag ctatga-
caaatatcacgaatgatagaacaaat-
cagcaagttaatgactcaaacaaatcaagcgcttgacacattgc
attagtgacgcctgaccatattgtta-
gagcagctgctagagatgcagttaagcaacaatatgaagctaaaaagcac
gaaattgagcaagcggaacatgcgactgatgaagaaaaacaagttgctttaaatcaatagcgaataatgaaaaa cgtgcatta-
caaaacattaatcaagcaatagc-
gaataatgatgtgaaacgtgttgaatcaaatggtattgctacgttaa
aaggcgtagaaccgcacattgtggt-
taaacctgaagctcaagaagccaaaaagcgagcgcagataaccaagta gaatc-
tataaaagatacaccatgctactgacga-
gatgaattagatgaagcaaaccaacaaataaacgacacactt
aaacaaggtcaacaagatataga-
caatacgacacaagatgcagctgtcaatgatgttagaaaccaaacgattaa
ggcaatcgaacaaattaaaccgaaagt-
tagacgcaaacgtgcagcgttggataacattgatgaaagtaataataat caactc-
gatgcaatacgaaatacgctagata-
caacgcaagatgaacgaaatgttgctattgctgcgttaaataaaat
tgttaatgcaattaaaaatgatattgca-
caaaacaaaacgaatgcagaagtggatcaaactgaggctgatggtaac aacaa-
catcaaagtgattttacctaaagt-
tcaagttaaaccagcagcgcgtcaatctgtcagcgcaaaagctgaag
ctcaaaatgcacttattgatcaaagt-
gatttatctaccgaagaagaaagattagctgctaaacatttagtagaacaag cact-
taatcaagctattgatcagatcaat-
cacgcagataagactgcgcaagttaatcaaaatagtatcgatgctcaaa
atattatttcaaaaattaaaccagcga-
caacagttaaagcaacagcattcaacaaattcaaatatcgctacaaat aaaat-
taatttaattaaagcaaataacgaagc-
gacagatgaagaacaaaatgctgcaatagtacaagttgaaaaa
gagttaattaaagctaaacaacaaat-
tgctggtgcagtgactaatgctgatgtggcatatttattgcatgatgggaaaa
acgaaattcgtgaaatcgaacctgttat-
taataaaaaagcaactgcgcgagaacaattaacaacattattcaaagat aagaaa-
caagcaattgaagcgaatgttcaagcaa-
cagtagaagaagaaatagtattttagcacagttacaaaa
catttatgacactgctattggacaaat-
tgatcaagatcgtagcaatgcacaagttgataaaacagcaacattaaatct acaaa-
caatacatgatttagacgtacatcctat-
taaaaagccagatgctgaaaaaacgattaatgatgatcttgcac
gtgttacacattagtgcaaaattatc-
gaaaagtaagtgatcgtaataaggctgatgcattaaaagctataactgcatt aaaat-
tacaaatggatgaagaattaaaaacag-
cacgcactaatgctgatgttgatgcagttttaaaacgatttaatgtt
gcattaggcgatatagaagcagtaat-
tactgaaaaagaaaatagcttactgcgcattgataacattgctcaacaaac atat-
.gcgaaattcaaagcgatcgcaacacca-
gaacaattagctaaagtaaaagcattaattgatcaatatgttgcag
atggcaatagaatggttgatgaagatgc-
gacattaaatgacatcaaaaaagatacgcaactcattattgatgaaattt agcaat-
taaattacctgctgaagt-
gataaaagcgtcaccaaaagtggggcaacctgctccaaaagtttgtacgcct
attaaaaaagaagataaacaagaagtgc-
gaaaagttgtaaaagaacttccaaatactggttctgaagaaatggatt taccaf-
taaaagaattagcactaattacaggcg-
cagcattattagctagaagacgttctaaaaaagaaaaagaatc ataa
EkeS_MRSA (SEQ ID NO:2)
 MNLLKKNKYSIRKYKVGIFSTLIGTV-
LLLSNPNGAQALTTDHNVQGGSNQALPGNS QNT-
NADTNRDIVNDSQNTPNAHATDNTST-
NQALTNHQNVDVANQVGPAPIQPSA
SPAQNNNNSNANSTATEPAANT-
NNLASNNNTLNVPNNTDNNDSARHLTLKEIQE
DVRHSSDKPELVAIAEEASNRPKKRSR-
RAAPTDPNATPADPTATPADPTAGNGSA PVAITAPY-
TPTTDPNANNIGQNAPNEVLSFDDN-
NIRPSTNRSVPTVTVVDNLPGYTL
INGGKVGVFSHAMVRTSMFDS-
GDAKNYQAQGNVIALGRIRGNDTNDHGDFNGIEK
TLTVNPNSELIFEFNTMTTKNYQGMT-
NLIIKNADNDTVIGEKVVAYGPIWRLLKVPE
NVSHLKIQFVPKNDAITDARGIYQL- RDGYKYYDFVDSIGLHSGSHVYVERRTMEPT ATNN-
KEFTVTTSLKNNGNFGASFNTD-
DFVYKIQLPEGVEYVNNSLTKDFPSGNSG
VDINDMNVTYDAANRIITIKSTGGGT-
GNSPARLMPDKILDLKYKLRVNNVPTPRTVT FNDTL-
TYKTYSQDFINSPAESHTVSTNPYTIDI-
IMNKDALQAEVDRRIQQADYTFASL
DIFNDLKRRAQTILDENRNNV-
PLNKRVSQADIDSLANQMQHTLIRSVDAENAVNRK
VDDMEDLVNQNDELTDEEKQMIQVIEEH-
KNEIIGNIGDQTTDDGVTRIKDQGIQTL SGDTATPV-
VKPNAKQAIRDKAAKQREIINHTPDATQ-
DEIQDALNQLTTDETDAIDNV
TNATTNADVETAKNNGINTI-
GAVAPQVTHKQAARDAINQATATKRQQINSNREATQ
EEKNAALNELTQATNHALEQINQATTND-
DVDTAKGDGLNAINPIAPVTVVKQAARD AVSH-
DAQQHIAEINANPDATQEER-
QAAIEKVYAAVAVANTNILNANTNADVEQVKT
NAIQGIQAIEPATKVKTDAKNAIDQSA-
ETQHNAIFNNNDATLEEQQMQQLLDQAVA TAKQN-
INMDTNQEVAQAKDQGTQNIWIQ-
PATQVKTDARNAVNEKAREAITNINA
TPGATREEKQEAINRVNTLKNRALN-
DIGVTSTTAMVNSIRDDAVNQIGAVQPHVTK KQTAT-
GVLTDLATAKKQEINQNTNAT-
TEEKQVALNQVDQDLATAINNINQADTNAE
VDQAQQLGTKAINAIQP-
NIVKKPAALAQTNQHYSAKLVEINATP-
DATDDEKNMINT LNQDRQQAIESIKQANTNAE-
VDQAATVAENNIDAVQVDWKKQAARDKITAEVAKR
IEAVKQTPNATDEEKQMVNQIN-
QLKDQAFNQINQNQTNDQVDATTNQAINAIDNV
EAEWIKPKAIADIEKAVKEKQQ-
QIDNSLDSTDNEKEVALQALAKEKEKALAAIDQA
QTNSQVNQAATNGVSAIKIIQPETKIK-
PAAREKINQKANELRAQINQDKEATAEERQ MLD-
KINDLVAKAMTNITNDRTNQQVNDST-
NQALDDIALVTPDHIVRAAARDAVKQ
QYEAKKHEIEQAEHATDEEKQVALN-
QLANNEKRALQNINQAIANNDVKRVESNGIA
TLKGVEPHIWKPEAQEAIKASADN-
QVESIKDTPHATTDELDEANQQINDTLKQGQ
QDIDNTTQDAAVNDVRNQTIKAIEQIKP-
KVRRKRAALDNIDESNNNQLDAIRNTLDT TQDERN-
VAIMLNKIVNAIKNDIAQNKTNAE-
VDQTEADGNNNIKVILPKVQVKPAAR
QSVSAKAEAQNALIDQSDLSTEEERLAA-
KHLVEQALNQAIDQINHADKTAQVNQNS IDAQNI-
ISKIKPATTVKATALQQIQNIATNKIN-
LIKANNEATDEEQNMIVQVEKELIKA
KQQIAGAVTNADVAYLLHDGKNEIR-
EIEPVINKKATAREQLTTLFNDKKQAIEANVQ
ATVEERNSILAQLQNIYDTAIG-
QIDQDRSNAQVDKTATLNLQTIHDLDVHPIKKPDAE
KTINDDLARVTH LVQNYRKVSDRNKADAL-
KAITALKLQMDEELKTARTNADVDAVL KRFNVAL-
GDIEAVITEKENSLLRIDNIAQQTYAKF-
KAIATPEQLAKVKALIDQYVADG
NRMVDEDATLNDIKKDTQLII-
DEILAIKLPAEVIKASPKVGQPAPKVCTPIKKEDKQEV
RKWKELPNTGSEEMDLPLKELALIT-
GAALLARRRSKKEKES
DsqA (8325) (SEQ ID NO:3)
tctaatgaatgtaaagataatacaag-
gagttattacatgagtaaaagacagaaagcatttcatgacagcttagcaaa
cgaaaaaacaagagtaagactt-
tataaatctggaaaaaattgggtaaaatccggaattaaagaaatagaaatgttc
aaaattatggggctaccatttattagt-
catagtttagtgagtcaagataatcaaagcattagtaaaaaaatgacgggat acg-
gactgaaaactacggcggttattggtg-
gtgcattcacggtaaatatgttgcatgaccagcaagcttttgcggcttct
gatgcaccattaacttctgaattaaaca-
cacaaagtgaaacagtaggtaatcaaaactcaacgacaatcgaagcat caacat-
caacagccgattccacaagtgtaac-
gaaaaatagtagttcggtacaaacatcaaatagtgacacagtctc
aagtgaaaagtctgaaaaggtcacttc-
gacaactaatagtacaagcaatcaacaagagaaattgacatctcatc agaat-
caacatcctcaaagaatactacat-
caagttctgatactaaatctgtagcttcaacttcaagtacagaacaacc
aattaatacatcaacaaatcaaagtact-
gcatcaaataacacttcacaaagcacaacgccatcttcggtcaacttaa
acaaaactagcacaacgtcaactagcac-
cgcaccagtaaaacttcgaactttcagtcgcttagctatgtcaacatttg cgtcag-
cagcgacgacaaccgcagtaact-
gctaatacaattacagttaataaagataacttaaaacaatatatgac
aacgtcaggtaatgctacctatgat-
caaagtaccggtattgtgacgttaacacaggatgcatacagccaaaaggtg
ctattacattaggaacacgtat-
tgactctaataagagttttcattttctggaaaagtaaatttaggtaacaaatatgaag
ggcatggaaatggtggagatggtatcg-
gttttgccttttcaccaggtgtattaggtgaaacagggttaaacggtgccgc agtag-
gtattggtggcttaagtaaccgcatttg-
gcttcaaattggatacgtatcacaatacatctaaaccaaattcagctg
caaaggagaatgctgacccatctaatg-
tagctggtggaggtgcgtttggtgcatttgtaacaacagatagttatggtgtt gcga-
caacgtatacatcaagttcaacagct-
gataatgctgcgaagttaaatgttcaacctacaaataacacgttcca
agattttgatattaactataatggt-
gatacaaaggttatgactgtcaaatatgcaggtcaaacatggacacgtaatattt
cagattggaftgcgaaaagtggtacgac-
caacttttcattatcaatgacagcctcaacaggtggcgcgacaaatttac aacaag-
tacaatttggaacattcgaatataca-
gagtctgctgttacacaagtgagatacgttgatgtaacaacaggta
aagatattattccaccaaaaacatat-
tcaggaaatgttgatcaagtcgtgacaatcgataatcagcaatctgcattga
ctgctaaaggatataactacacgtc-
cgtcgatagttcatatgcgtcaacttataatgatacaaataaaactgtaaaaat gac-
gaatgctggacaatcagtgacatat-
tattttactgatgtaaaagcaccaactgtaactgtaggcaatcaaaccat
agaagtgggtaaaacaatgaatcctat-
tgtattgactacaacggataatggtactgggactgtgacaaatacagttac aggat-
taccaagcggattaagttaagatagtg-
caacgaattcaatcattgggacaccaacaaaaattggtcaatca
acagtgacagttgtgtctactgaccaag-
caaataacaaatcgacgacaacttttacaataaatgttgtggatacgaca gcac-
caacagtgacaccaataggagatcaat-
catcagaagtgtattcaccaatatccccgattaaaattgctacgca
agataacagtggaaatgcggtgac-
gaatacagtgactggattgccatccggactaacattgatagtcaaataata ctatt-
agtggtacaccaacaaacattggta-
caagtactatatcaatcgtttctacagatgcgagcggtaacaaaacga
cgacaacttttaaatatgaagtaacaa-
gaaatagcatgagtgattccgtatcaacatcaggaagtacacaacaatcc caaagt-
gtgtcaacaagtaaagctgactca-
caaagtgcatcaacgagtacatcaggatcgattgtggtatctacatc
agctagtacctcgaaatcgacaagtg-
taagcctatctgattctgtgagtgcatctaagtcattaagcacatctgaaagt aat-
agtgtatcaagctcaacaagcacaagtt-
tagtgaattcacaaagtgtatcatcaagcatgtcggattcagctagt
aaatcaacatcaftaagcgattc-
tatttcaaactctagcagtactgaaaaatccgaaagtctatcaacaagtacatctg
attcattgcgtacatcaacatcact-
cagtgactcattaagtatgagtacatcaggaagcttgtctaagtcacaaagctta tcaacgagtatatcagggtcgtctagta-
catcagcatcattaagtgacagtacatcgaatgcaattagtacatcaacat cat-
tgagcgagtcagctagcacctcggactc-
tatcagtatttcaaatagcatagccaactctcaaagtgcgtcaacaa
gcaaatcagattcacaaagtacat-
caatatcattaagtacaagtgattcaaaatcgatgagtacatcagaatcattga
gcgattcgacgagcacaagtggttct-
gtttctggatcactaagcatagcagcatcacaaagtgtctcaacaagtacat
cagactcgatgagtacttcagagatag-
taagtgactctatcagtacaagtgggtcattatctgcatcagacagtaaatc aat-
gtccgtaagtagttcaatgagcacgtct-
cagtcaggtagtacatcagaatcattaagtgattcacaaagtacatct
gattctgatagtaagtcattatca-
caaagtactagtcaatcaggttcaacaagtacatcaacgtcgacaagtgcttcag
tacgtacttcggaatcacaaag-
tacgtctggttcaatgagtgcaagtcaatccgattcaatgagcatatcaacgtcgttt
agtgattcaacgagtgatagcaaatcag-
catcaactgcatcaagtgaatcaatatcacaaagtgcttctacgagcac atctggt-
tcggtaagtacttcgacatcgttaagta-
caagtaattcagaacgtacatcaacatctatgagtgattccacaa
gcttaagtacatcagagtctgat-
tcaataagtgaatcaacgtcaacgagcgactctataagtgaagcaatatctgcttc
agagagcacgtttatatcattaagt-
gaatcaaatagtactagcgattcagaatcacaaagtgcatctgccttttaagtg
aatcattaagtgaaagtacgtctgaat-
caacatcagagtcagtgagtagttcgacaagtgagagtacgtcattatcag acag-
tacatcagaatctggtagcacatcaa-
catcattaagtaattcaacaagtggtagtacgtccatttcaacatcga
caagtatcagtgaatcaacgtcaacgtt-
taagagcgagagtgtttcaacatcactgagtatgtcaacgagtacaagtt tgtct-
gactctacaagtttgtcaacatcat-
taagtgattccacaagtgatagtaagtctgattcattaagtacatcaatgtc
gacaagtgattcaatcagtacaag-
taaatctgattccattagtacatccacatcattaagtggttctacaagtgaaagt
gaatccgactcaacatcatcaagt-
gaaagtaaatccgattcaacatcaatgagcataagtatgtctcaatcaacatc
aggaagtacaagtacgtcaacgagta-
caagtttgtctgactcaacgagtacatcattgtcactaagtgcctcaatgaa
tcaaagcggagtagactcaaactcag-
caagccaaagtgcctcaaactcaacaagtacaagcacgagcgaatcc gattca-
caaagcacatcatcatatacaagtcagt-
caacaagccaaagtgaatccacatcgacatcaacgtcactaa
gcgattcaacaagtatatctaaaagtac-
gagtcaatcaggttcggtaagcacatcagcgtcattaagtggttcagag agt-
gaatctgattcacaaagtatctcaa-
caagtgcaagtgagtcaacatcagaaagtgcgtcaacatcactcagtga
ctcaacaagtacaagtaactcaggat-
cagcaagtacgtcaacatcgctcagtaactcagcaagcgcaagtgaatc
cgatttgtcgtcaacatctttaagtgat-
tcaacatctgcgtcaatgcaaagcagtgaatccgattcacaaagaacatca gcat-
cattaagtgattcgctaagtacat-
caacttcaaaccgcatgtogaccattgcaagtttatctacatcggtaagtac
atcagagtctggctcaacatcagaaag-
tacaagtgaatcogattcaacatcaacatcattaagcgattcacaaagc acatcaa-
gaagtacaagtgcatcaggatcagcaag-
tacatcaacatcaacaagtgactctcgtagtacatcagctt
caactagtactcgatgcgtacaagtac-
tagtgattcacaaagtatgtcgctttcgacaagtacatcaacaagtatgag tgat-
tcaacgtcattatctgatagtgttagt-
gattcaacatcagactcaacaagtgcgagtacatctggttcgatgagtgt
gtctatatcgttaagtgattcgacaag-
tacatcaacatcggctagtgaagtaatgagcgcaagcatatctgattcacaa
agtatgtaagaatctgtaaatgattca-
gaaagtgtaagtgaatctaatctgaaagtgactctaaatcgatgagtggctc
aacaagtgtcagtgattctggctcat-
tgagcgtctcaacgtcattaagaaaatcagaaagtgtaagcgagtcaagttc
attgagttgctcacaatcgatgagagat-
tcagtaagcacaagcgattcgtcatcattaagtgtatcgacgtcactaaga agttca-
gaaagcgtgagtgaatctgattcat-
taagtgattcaaaatcaacaagtggttcgacttcaacaagtacatctg
gttcattgagtacctcaacatcaf-
taagtggttcagaaagcgtaagcgagtctacctcgctaagtgattcaatatcaatg
agtgattctactagtacaagtgactc-
cgactcattaagtggatcaatatctttaagtggttccacaagtcttagcacttcg gat-
tcattaagtgattcaaaatcattgag-
tagctcgcaaagtatgagtggatcagaatcaacgtcaacaagtgtgagc
gattcgcagtcaagctcaacaagtaat-
agtcaatttgactctatgagcatcagtgcatcagaaagcgactcaatgtct acaagt-
gattcgtctagcatcagtggatcaaat-
tcaacgagtacatcactttcaacatctgactcaatgagcggaagc
gtatcagtttcaacatcgacaagtt-
taagtgactcaatatcaggttcaacaagtgtaagtgactcgagctcaacaagc
acatctacatcattaagtgattcaatgt-
cacaaagccagtcaacaagtacaagtgcatctggttccttaagtacatcga tat-
caacatcaatgtcaatgagtgctagta-
catcgtcatcacaaagcacatcggtgtcgacatcattatcaacatcag
acagtatcagtgattctacttcaataag-
tatcagtggttcacaaagtacagtagaatcagaatctacaagtgattcaac ttctat-
cagtgactcagaatcattgagtacatca-
gattcagactcgacatcgacaagtacatcggactcaacaagtgg
ttcaacttcaacaagcatatctgaat-
cattaagtacgtctggftcaggttcaacgagcgtatctgactcaacatcaatga
gtgaatctaattcatagagtgtttcaat-
gtcacaagacaaatccgactcaacatcaattagtgactcagaatcagtgtc
aacaagcacatcaacgtcattgagca-
catccgattcgacaagcacatccgaatcactgagtacatctatgtctggttc
acaaagcatttctgactcaacatcaa-
caagtatgtccggctcaacaagtacatctgaatctaactcaatgcatccgtc
agactcaatgagtatgcatcatactca-
cagcacgagcacatctcgcttatcaagtgaagcaacaacgagcacgagt
gaatctcagtctacattaagtgcaa-
catctgaagtgactaaacataatggcaaccagcacaaagtgaaaaaaga ttgc-
cagatacaggtgactcaataaaa-
caaaatggattactaggtggcgttatgacattattagttggtttaggtttaatg
aagagaaagaaaaagaaagatgaaaatgatcaagatgattctcaagcataa DsqA (8325) (SEQ ID NO:4)

SNECKDNTRSYYMSKRQKAFHDSLANEK-
TRVRLYKSGKNWVKSGIKEIEMFKIMG LPFISH-
SLVSQDNQSISKKMTGYGLKTTAVIG-
GAFTVNMLHDQQAFMSDAPLTSE
LNTQSETVGNQNSTTIEASTSTADSTS-
VTKNSSSVQTSNSDTVSSEKSEKVTSTTN STSN-
QQEKLTSTSESTSSKNTTSSSDTKS-
VASTSSTEQPINTSTNQSTASNNTSQS
TTPSSVNLNKTSTTSTSTAPVKLRTFSR-
LAMSTFASAATTTAVTANTITVNKDNLKQ YMTTSG-
NATYDQSTGIVTLTQDAYSQK-
GAITLGTRIDSNKSFHFSGKVNLGNKYEG
HGNGGDGIGFAFSPGVLGETGLNGMV-
GIGGLSNAFGFKLDTYHNTSKPNSAAKA NADPSN-
VAGGGAFGAFVTTDSYGVATTYTSSS-
TADNNMKLNVQPTNNTFQDFDIN
YNGDTKVMTVKYAGQTWTRNISDWIAKS-
GTTNFSLSMTASTGGATNLQQVQFGT FEYTESAV-
TQVRYVDVTTGKDIPPPKTYSGN-
VDQWTIDNQQSALTAKGYNYTSVD
SSYASTYNDTNKTVKMTNAGQSVTYYFT-
DVKAPTVTVGNQTIEVGKTMNPIVLTTT DNGT-
GTVTNTVTGLPSGLSYDSATNSIIGTPT-
KIGQSTVTwSTDQANNKSTTTFTI
NWDTTAPTVTPIGDQSSEVYSPISPIKI-
ATQDNSGNAVTNTVTGLPSGLTFDSTNN TISGTPT-
NIGTSTISIVSTDAS-
GNKTTTTFKYEVTRNSMSDSVSTSGSTQQSQSVST

SKADSQSASTSTSGSIWSTSASTSKSTS-
VSLSDSVSASKSLSTSESNSVSSSTST SLVNSQS-
VSSSMSDSASKSTSLSDSISNSSSTEK-
SESLSTSTSDSLRTSTSLSDSL
SMSTSGSLSKSQSLSTSISGSSST-
SASLSDSTSNAISTSTSLSESASTSDSISISNSI
ANSQSASTSKSDSQSTSISLSTSD-
SKSMSTSESLSDSTSTSGSVSGSLSIMSQSV STSTS-
DSMSTSEIVSDSISTSGSLSASDSKSMS-
VSSSMSTSQSGSTSESLSDSQST
SDSDSKSLSQSTSQSGSTSTSTSTSAS-
VRTSESQSTSGSMSASQSDSMSISTSFS DSTSD-
SKSASTASSESISQSASTSTSGS-
VSTSTSLSTSNSERTSTSMSDSTSLSTS
ESDSISESTSTSDSISEAISASEST-
FISLSESNSTSDSESQSASAFLSESLSESTSES TSES-
VSSSTSESTSLSDSTSESGSTSTSL-
SNSTSGSTSISTSTSISESTSTFKSESV
STSLSMSTSTSLSDSTSLSTSLSDSTSD-
SKSDSLSTSMSTSDSISTSKSDSISTSTS LSGSTSESES-
DSTSSSESKSDSTSMSISM-
SQSTSGSTSTSTSTSLSDSTSTSLSLS
ASMNQSGVDSNSASQSASNSTSTSTSES-
DSQSTSSYTSQSTSQSESTSTSTSLS DST-
SISKSTSQSGSVSTSASLSGSESESDSQ-
SISTSASESTSESASTSLSDSTSTS
NSGSASTSTSLSNSASASESDLSSTSLS-
DSTSASMQSSESDSQSTSASLSDSLST STSNRMS-
TIASLSTSVSTSESGSTSESTSES-
DSTSTSLSDSQSTSRSTSASGSAST
STSTSDSRSTSASTSTSMRTSTSD-
SQSMSLSTSTSTSMSDSTSLSDSVSDSTSDS TSAS-
TSGSMSVSISLSDSTSTSTSASEVMSA-
SISDSQSMSESVNDSESVSESNSE
SDSKSMSGSTSVSDSGSLSVSTSLRK-
SESVSESSSLSCSQSMSDSVSTSDSSSLS VSTSLRSS-
ESVSESDSLSD-
SKSTSGSTSTSTSGSLSTSTSLSGSESVSESTSLSDS
ISMSDSTSTSDSDSLSG-
SISLSGSTSLSTSDSLSDSKSLSSSQSMSGSESTSTSVS
DSQSSSTSNSQFDSMSISASESDSMSTS-
DSSSISGSNSTSTSLSTSDSMSGSVSV STSTSLSD-
SISGSTSVSDSSSTSTSLSDSM-
SQSQSTSTSASGSLSTSISTSMSM
SASTSSSQSTSVSTSLSTSDSISDSTSI-
SISGSQSTVESESTSDSTSISDSESLSTSD SDSTSTSTS-
DSTSGSTSTSISESLSTSGSGSTSVS-
DSTSMSESNSSSVSMSQDKS
DSTSISDSESVSTSTSTSLSTSDSTST-
SESLSTSMSGSQSISDSTSTSMSGSTSTS ESNSMHPS-
DSMSMHHTHSTSTSRLSSEATTST-
SESQSTLSATSEVTKHNGTPAQ
SEKRLPDTGDSIKQNGLLG-
GVMTLLVGLGLMKRKKKKDENDQDDSQA
KesK1 (8325) (SEQ ID NO:5)

ttattatcaattaaatataatcttatag-
gagttgttaacaacatgaacaaacatcacccaaaattaaggtcttttctattctat
tagaaaatcaactctaggcgttgcatcg-
gtcattgtcagtacactattttaattacttctcaacatcaagcacaagcag
cagaaaatacaaatacttca-
gataaaatctcggaaaatcaaataataatgcaactaacaactcagccacctaagg
atacaaatcaaacacaacctgctacg-
caaccagcaaacactgcgaaaaactatcctgcagcggatgaatcactta aagat-
gcaattaaagatcctgcatta-
gaaaataaagaacatgatataggtccaagagaacaagtcaatttccagtta
ttagataaaaacaatgaaacgcagtac-
tatcactttttcagcatcaaagatccagcagatgtgtattacactaaaaag aaagcagaagttgaattagacatcaatactgct-
tcaacatggaagaagtttgaagtctatgaaaacaatcaaaaatt
gccagtgagacttgtatcatatagtcct-
gtaccagaagaccatgcctatattcgattccagtttcagatggcacacaa gaat-
tgaaaattgtttcttcgactcaaat-
tgatgatgggaagaaacaaattatgattatactaaattagtatttgctaaa
cctatttataacgatccttcacttg-
taaaatcagatacaaatgatgcagtagtaacgaatgatcaatcaagttcagtcgc
aagtaatcaaacaaacacgaata-
catctaatcaaaatatatcaacgatcaacaatgctaataatcaaccgaaggc aac-
gaccaatatgagtcaacctgcacaac-
caaaatcgtcaacgaatgcagatcaagcgtcaagccaaccagctc
atgaaacaaattctaatggtaatac-
taacgataaaacgaatgagtcaagtaatcagtcggatgttaatcaacagtatc cac-
cagcagatgaatcactacaagatgcaat-
taaaaacccggctatcatcgataaagaacatacagctgataattg
gcgaccaattgattttcaaatgaaaat-
gataaaggtgaaagacagttctatcattatgctagtactgttgaaccagca actgt-
catttttacaaaaacaggaccaataat-
tgaattaggtttaaagacagcttcaacatggaagaaatttgaagttt
atgaaggtgacaaaagttaccagtc-
gaattagtatcatatgattctgataaagattatgcctatattcgtttcccagtat
ctaatggtacgagagaagttaaaattgt-
gtcatctaftgaatatggtgagaacatccatgaagactatgattatacgcta atg-
gtctttgcacagcctattactaataac-
cagacgactatgtggatgaagaaacatacaatttacaaaaattattag
ctccgtatcacaaagctaaaacgtta-
gaaagacaagtttatgaattagaaaaaftacaagagaaattgccagaa
aaatataaggcggaatataaaa-
gaaattagatcaaactagagtagagttagctgatcaagttaaatcagcagtga
cggaatttgaaaatgftacaccta-
caaatgatcaattaacagatttacaagaagcgcattttgttgtttttgaaagtgaa
gaaaatagtgagtcagttatggacg-
gctttgttgaacatccattctatacagcaacttaaatggtcaaaaatatgtagt gat-
gaaaacaaaggatgacagttactggaaa-
gatttaattgtagaaggtaaacgtgtcactactgttctaaagatcct
aaaaataattctagaacgctgattttc-
ccatatatacctgacaaagaagtttaacaatgcgattgttaaagtcgttgtggc aaa-
cattggttatgaaggtcaatatcatgt-
cagaattataaatcaggatatcaatacaaaagatgatgatacatcaca
aaataacacgagtgaaccgctaaatgta-
caaacaggacaagaaggtaaggttgctgatacagatgtagctgaaa atagcag-
cactgcaacaaatcctaaagatgcgtct-
gataaagcagatgtgatagaaccagagtctgacgtggttaa
agatgctgataataatattgataaagat-
gtgcaacatgatgttgatcatttatccgatatgtcgataataatcacttcga
taaatatgatttaaaagaaatggatact-
caaattgccaaagatactgatagaaatgtggataaagatgccgataat agcgttg-
gtatgtcatctaatgtcgatact-
gataaagactctaataaaaataaagacaaagtcatacagctgaatcat
attgccgataaaaataatcatactg-
gaaaagcagcaaagcttgacgtagtgaaacaaaattataataatacagaca aagt-
tactgacaaaaaaacaactgaacatct-
gccagtgatattcataaaactgtagataaaacagtgaaaacaa
aagaaaagccggcacaccatcgaaa-
gaaaacaaacttagtcaatctaaaatgctaccaaaaactggagaa acaacft-
caagccaatcatggtggggcttatat-
gcgttattaggtatgttagctttattcattcctaaattcagaaaagaat ctaaataa
KesK1 (8325) (SEQ ID NO:6)
LLSIKYNLIGWNNMNKHHPKLRSFY-
SIRKSTLGVASVIVSTLFLITSQHQAQMENT NTSD-
KISENQNNNATTTQPPKDTNQTQPATQ-
PANTAKNYPMDESLKDAIKDPALE
NKEHDIGPREQVNFQLLDKNNETQYYH-
FFSIKDPADVYYTKKKAEVELDINTASTW KKFEVY-
ENNQKLPVRLVSYSPVPEDHAYIRFPVS-
DGTQELKIVSSTQIDDGEETNY DYTKLVFAKPIYNDPSLVKSDTNDAVVT-
NDQSSSVASNQTNTNTSNQNISTINNAN NQPQATT-
NMSQPAQPKSSTNADQASSQPAHET-
NSNGNTNDKTNESSNQSDVNQ
QYPPADESLQDAIKNPAIIDKEHTADN-
WRPIDFQMKNDKGERQFYHYASTVEPATV IFTKTG-
PIIELGLKTASTWKKFEVYEGD-
KKLPVELVSYDSDKDYAYIRFPVSNGTRE
VKIVSSIEYGENIHEDYDYTLMV-
FAQPITNNPDDYVDEETYNLQKLLAPYHKAKTLE
RQVYELEKLQEKLPEKY-
KAEYKKKLDQTRVELADQVKSAVTEFEN-
VTPTNDQLTD LQEAHFVVFESEENSESVMDGFVEH-
PFYTATLNGQKYVVMKTKDDSYWKDLIVEG
KRVTTVSKDPKNNSRTLIFPYIPD-
KAVYNAIVKVVVANIGYEGQYHVRIINQDINTKD
DDTSQNNTSEPLNVQTGQEGKVADTD-
VAENSSTATNPKDASDKADVIEPESDWK DADNNID-
KDVQHDVDHLSDMSDNNHFDKY-
DLKEMDTQIAKDTDRNVDKDADNSV
GMSSNVDTDKDSNKNKDKVIQLNHIAD-
KNNHTGKAAKLDWKQNYNNTDKVTDKK TTE-
HLPSDIHKTVDKTVKTKEKAGTPSKEN KLSQSKM-
LPKTGETTSSQSWWGLYA LLGMLALFIPKFRKESK
KrkN2 (8325) (SEQ ID NO:7)
gaggaaaacaacatgacaaaacattatt-
taaacagtaagtatcaatcagaacaacgttca tcagctatgaaaaagatta-
caatgggtacagcatctatcatttaggttcccttgtatac ataggcgcagacagc-
caacaagtcaatgcggcaacagaagctacgaacgcaactaataat
caaagcacacaagtttctcaagcaacat-
cacaaccaattaatttccaagtgcaaaaagat ggctcttcagagaagtcacacatg-
gatgactatatgcaacaccctggtaaagtaattaaa caaaataataaatattattc-
caaaccgtgttaaacaatgcatcattctggaaagaatac
aaattttacaatgcaaacaatcaa-
gaattagcaacaactgttgttaacgataataaaaaa gcggatactagaacaat-
caatgttgcagttgaacctggatataagagcttaactactaaa gtacatattgtcgt-
gccacaaattaattacaatcatagatatactacgcatttggaattt
gaaaaagcaattcctacattagctgacg-
cagcaaaaccaaacaatgttaaaccggttcaa ccaaaaccagctcaacctaaaa-
cacctactgagcaaactaaaccagttcaacctaaagtt gaaaaagttaaacctact-
gtaactacaacaagcaaagttgaagacaatcactctactaaa
gttgtaagtactgacacaacaaaagat-
caaactaaaacacaaactgctcatacagttaaa acagcacaaactgctcaagaa-
caaaataaagttcaaacacctgttaaagatgttgcaaca gcgaaatctgaaag-
caacaatcaagctgtaagtgataaatcacaacaaactaacaaa
gttacaaaacataacgaaacgcctaaa-
caagcatctaaagctaaagaattaccaaaaact ggtttaacttcagttgataactt-
tattagcacagttgccttcgcaacacttgccctftta ggttcattatctttat-
tacttttcaaaagaaaagaatctaaataa
KrkN2 (8325) (SEQ ID NO:8)
EENNMTKHYLNSKYQSEORSSAMKKIT-
MGTASIILGSLVYIGADSQQVNMTEATN
ATNNQSTQVSQATSQPIN-
FQVQKDGSSEKSHMDDYMQHPGK-
VIKQNNKYYFQTV LNNASFWKEYKFYNAN-
NQELATTVVNDNKKADTRTINVAVEPGYKSLTTKVHIVVPH
QINYNHRYTTHLEFEKAIPTLADMKPN-
NVKPVQPKPAQPKTPTEQTKPVQPKVEK
VKPTVTTTSKVEDNHSTKVVSTDTT-
KDQTKTQTAHTVKTAQTAQEQNKVQTPVKD
VATAKSESNNQAVSDNKSQQTNKVTKH-
NETPKQASKAKELPKTGLTSVDNFISTV AFATLA-
LLGSLSLLLFKRKESK
KrkN (8325) (SEQ ID NO:9)
tatacaattaggagttgtttctacaa-
catgaacaaacagcaaaaagaatttaaatcatttattcaattagaaagtcatc act-
aggcgttgcatctgtagcaattagta-
cactttattattaatgtcaaatggcgaagcacaagcagcagctgaaga
aacaggtggtacaaatacagaagca-
caaccaaaaactgaagcagttgcaagtccaacaacaacatctgaaaaa gctcca-
gaaactaaaccagtagctaatgctgtct-
cagtatctaataaagaagttgaggccccctacttctgaaacaaa
agaagctaaagaagttaaagaagt-
taaagcccctaaggaaacaaaagaagttaaaccagcagcaaaagccac taa-
caatacatatcctatttgaatcag-
gaacttagagaagcgattaaaaaccctgcaataaaagacaaagatcata
gcgcaccaaaactctcgtccaat-
tgattttgaaatgaaaaagaaagatggaactcaacagttttatcattatgcaagttc
tgttaaacctgctagagttattttcact-
gattcaaaaccagaaattgaattaggattacaatcaggtcaattttggagaaa
atttgaagtttatgaaggtga-
caaaaagttgccaattaaattagtatcataogatactgttaaagattatgcttacattcg
cftctctgtatcaaacggaacaaaagct-
gttaaaattgttagttcaacacacttcaataacaaagaagaaaaatacg attaca-
cattaatggaattcgcacaaccaatt-
tataacagtgcagataaattcaaaactgaagaagattataaagctg
aaaaattattagcgccatataaaaaagc-
gaaaacactagaaagacaagtttatgaattaaataaaattcaagataa acttcct-
gaaaaattaaaggctgagtacaagaa-
gaaattagaggatacaaagaaagctttagatgagcaagtgaa
atcagctattactgaattccaaaatgta-
caaccaacaaatgaaaaaatgactgattatcaagatacaaaatatgttgtt tat-
gaaagtgttgagaataacgaatctat-
gatggatactttgttaaacaccctattaaaacaggtatgcttaacggcaa
aaaatatatggtcatggaaactactaat-
gacgattactggaaagatttcatggttgaaggtcaacgtgttagaactata
agcaaagatgctaaaaataatactagaa-
caattattttcccatatgttgaaggtaaaactctatatgatgctatcgttaa agt-
tcacgtaaaaacgattgattatgatgga-
caataccatgtcagaatcgttgataaagaagaatttacaaaagcca
ataccgataaatctaacaaaaagaa-
caacaagataactcagctaagaaggaagctactccagctacgcctagc aaac-
caacaccatcacctgttgaaaaagaat-
cacaaaaacaagacagccaaaaagatgacaataaacaattac
caagtgttgaaaaagaaaatgacg-
catctagtgagtcaggtaaagacaaaacgcctgctacaaaaccaactaaa ggt-
gaagtagaatcaagtagtacaactc-
caactaaggtagtatctacgactcaaaatgttgcaaaaccaacaactg
cttcatcaaaaacaacaaaagatgttgt-
tcaaacttcagcaggttctagcgaagcaaaagatagtgctcattacaa aaag-
caaacattaaaaacacaaatgatggaca-
cactcaaagccaaaacaataaaaatacaagaaaataaa
gcaaatcattaccacaaactggtgaa-
gaatcaaataaagatatgacattaccattaatggcattattagctttaagta
gcatcgttgcattcgtattacctagaaaacgtaaaaactaa
KrkN (8325) (SEQ ID NO:10)
YTIRSCFYNMNKQQKEFKSFYSIRKSS-
LGVASVAISTLLLLMSNGEAQAAAEETGG TNTEAQP-
KTEAVASPTTTSEKAPETKPVANAVS-
VSNKEVEAPTSETKEAKEVKEV
KAPKETKEVKPMKATNNTYPILNQEL-
REAIKNPAIKDKDHSAPNSRPIDFEMKKKD GTQQFY-
PHYASSVKPARVIFTDSKPEIELGLQS-
GQFWRKFEVYEGDKKLPIKLVSYD
TVKDYAYIRFSVSNGTKAVKIVSSTH-
FNNKEEKYDYTLMEFAQPIYNSADKFKTEED
YKAEKLLAPYKKAKTLERQVYELNKIQD-
KLPEKLKAEYKKKLEDTKKALDEQVKSAI TEFQN-
VQPTNEKMTDLQDTKYVVYESVENNESM-
MDTFVKHPIKTGMLNGKKYMV
METTNDDYWKDFMVEGQRVR-
TISKDAKNNTRTIIFPYVEGKTLYDAIVKVHVKTIDY
DGQYHVRIVDKEAFTKANTDK-
SNKKEQQDNSAKKEATPATPSKPTPSPVEKESQK QDSQKDDNKQLPSVEKENDASSESGKDK-
TPATKPTKGEVESSSTTPTKVVSTTQ NVAKPT-
TASSKTTKDWQTSAGSSEAKDSAPLQ-
KANIKNTNDGHTQSQNNKNTQE
NKAKSLPQTGEESNKDMTLPLMALLA-
LSSIVAFVLPRKRKN RkaS (COL) (SEQ ID NO:11)

tttataaataatttacataaaatcaat-
cattttaataataaggattatgataatatattggtgtatgacagttaatggaggga
acgaaatgaaagctttatttactaaaa-
caagtgtatggctcgtttgcttttagtgtaatgggattatggcaagtctcgaa cgcg-
gctgagcagcatacaccaatgaaagca-
catgcagtaacaacgatagacaaagcaacaacagataagca
acaagtaccgccaacaaaggaagcggct-
catcattctggcaaagaagcggcaaccaacgtatcagcatcagcg cagggaa-
cagctgatgatacaaacagcaaagtaa-
catccaacgcaccatctaacaaaccatctacagtagtttca
acaaaagtaaacgaaacacgcgacgta-
gatacacaacaagcctcaacacaaaaaccaactcacacagcaac gttcaaattat-
caaatgctaaaacagcatcactttcac-
cacgaatgtttgctgctaatgcaccacaaacaacaaca
taaaatattacatacaaatgatatc-
catggccgactagccgaagaaaaaggggcgtgtcatcggtatggctaaaftaa
aaacagtaaagaacaagaaaagcct-
gatttaatgttagacgcaggagacgccttccaaggtttaccactttcaaa
ccagtctaaaggtgaagaaatg-
gctaaagcaatgaatgcagtaggttatgatgctatggcagtcggtaaccatgaat
ttgactttggatacgatcagt-
tgaaaaagttagagggtatgttagact-
tcccgatgctaagtactaacgtttataaagatg gaaaacgcgcgtttaagcct-
tcaacgattgtaacaaaaaatggtattcgttatggaattattggtgtaacgacaccag
aaacaaagacgaaacaagacctgaag-
gcattaaaggcgttgaatttagagatccattacaaagtgtgacagcg gaaatgat-
gcgtatttataagacgtagata-
catttgttgttatatcacatttaggaaftgatccttcaacacaagaaaca
tggcgtggtgattacttagtgaaacaat-
taagtcaaatccacaattgaagaaacgtattacagttattgatggtcattc acata-
cagtacttcaaaatggtcaaatttataa-
caatgatgcattggcacaaacaggtacagcacttgcgaatatcgg
taagattacatttaattatcgcaatg-
gagaggtatcgaatattaaaccgtcattgattaatgttaaagacgttgaaaatgt
aacaccgaacaaagcattagctgaa-
caaattaatcaagctgatcaaacatttagagcacaaactgcagaggtaat tattc-
caaacaataccattgatttcaaag-
gagaaagagatgacgttagaacgcgtgaaacaaatttaggaaacgcg
attgcagatgctatggaagcgtatg-
gcgttaagaatttctctaaaaagactgactttgccgtgacaaatggtggaggta
ttcgtgcctctatcgcaaaaggtaaggt-
gacacgctatgatttaatctcagtattaccatttggaaatacgattgcgcaa attgat-
gtaaaaggttcagacgtctggacg-
gctttcgaacatagtttaggcgcaccaacaacacaaaaggacggta
agacagtgttaacagcgaatggcggtt-
tactacatatctctgattcaatccgtgtttactatgatataaataaaccgtctg
gcaaacgaattaatgctattcaaattt-
taaataaagagacaggtaagtttgaaaatattgatttaaaacgtgtatatcac
gtaacgatgaatgacttcacagcatcag-
gtggcgacggatatagtatgttcggtggtcctagagaagaaggtatttca ttagat-
caagtactagcaagttatttaaaaa-
cagctaacttagctaagtatgatacgacagaaccacaacgtatgttat
taggtaaaccagcagtaagtgaacaac-
cagctaaaggacaacaaggtagcaaaggtagtaagtctggtaaagat acacaac-
caattggtgacgacaaagtgatggatc-
cagcgaaaaaaccagctccaggtaaagttgtattgttgctag
cgcatagaggaactgttagtagcggta-
cagaaggttctggtcgcacaatagaaggagctactgtatcaagcaaga gtgg-
gaaacaattggctagaatgtcagtgc-
ctaaaggtagcggcatgagaaacagttaccaaaaactggaacta atcaaagttcaagcccagaagcgat-
gtttgtattattagcaggtataggtttaatcgcgactgtacgacgtagaaaag
ctagctaa RkaS (COL) (SEQ ID NO:12)

FINNLHKINHFNIRIMIIYWCMTVNG-
GNEMKALLLKTSVWLVLLFSVMGLWQVSNM
EQHTPMKAHAVTTIDKATTDKQQVPPT-
KEAAHHSGKEAATNVSASAQGTADDTN SKVT-
SNAPSNKPSTVVSTKVNETRD-
VDTQQASTQKPTHTATFKLSNAKTASLSPR
MFMNAPQTTTHKILHTNDIHGR-
LAEEKGRVIGMAKLKTVKEQEKPDLMLDAGDAF
QGLPLSNQSKGEEMAKAMNAVGY-
DAMAVGNHEFDFGYDQLKKLEGMLDFPMLS
TNVYKDGKRAFKPSTIVTKNGIRYGI-
IGVTTPETKTKTRPEGIKGVEFRDPLQSVTA
EMMRIYKDVDTFVVISHLGIDPSTQET-
WRGDYLVKQLSQNPQLKKRITVIDGHSHT VLQNG-
QIYNNDALAQTGTALANIGKITFNYRN-
GEVSNIKPSLINVKDVENVTPN KAL
AEQINQADQTFRAQTAEVIIPNNTID-
FKGERDDVRTRETNLGNAIADAMEAYGVKN FSKKT-
DFAVTNGGGIRASIAKGKVTRYDLISV-
LPFGNTIAQIDVKGSDVWTAFEHSL
GAPTTQKDGKTVLTANGGLLHISD-
SIRVYYDINKPSGKRINAIQILNKETGKFENIDL KRVY-
HVTMNDFTASGGDGYSMFGGPREEG-
ISLDQVLASYLKTANLAKYDTTEPQR
MLLGKPAVSEQPAKGQQGSKGSKS-
GKDTQPIGDDKVMDPAKKPAPGKVVLLLAH
RGTVSSGTEGSGRTIEGATVSSKS-
GKQLARMSVPKGSAHEKQLPKTGTNQSSSP EAMFV-
LLAGIGLIATVRRRKAS

RrkN (8325) (SEQ ID NO:13)

agtggaaaatatggaaaaggagtatg-
caaatgagagataagaaggaccggtaaataaagagtagatttct
atcaaataaattgaataaatat-
tcaataagaaaatttacagttggaacagcatctatttaattggctcactaatgtatttg
ggaactcaacaagaggcagaagcagct-
gaaaacaatattgagaatccaactacattaaaagataatgtccaatc aaaagaagt-
gaagattgaagaagtaacaaacaaga-
cactgcaccacagggtgtagaagctaaatctgaagta
acttcaaacaaagacacaatcgaacat-
gaaccatcagtaaaagctgaagatatatcaaaaaaggaggatacac caaaa-
gaagtagctgatgttgctgaagttcagc-
cgaaatcgtcagtcactcataaccgcagagacacctaaggttag
aaaagctcgttctgttgatgaag-
gctcttttgatattacaagagattctaaaaatgtagttgaatctaccccaattacaatt
caaggtaaagaacattttgaaggttacg-
gaagtgttgatatacaaaaaaaaccaacagatttaggggtatcagagg taaccag-
gtttaatgttggtaatgaaagtaatg-
gtttgataggagcttttacaattaaaaaataaaatagattttagtaag
gatttcaattttaaagttagagtgg-
Gaaataaccatcaatcaaataccacaggtgctgatggttggggggttcttatttagt
aaaggaaatgcagaagaatatttaac-
taatggtggaatccttggggataaaggtctggtaaattcaggcggatttaa aat-
tgatactggatacatttatacaagttc-
catggacaaaactgaaaagcaagctggacaaggttatagaggatacg
gagcttttgtgaaaaatgacagttctgg-
taattcacaaatggttggagaaaatattgataaatcaaaaactaattttttaa actat-
gcggacaattcaactaatacatcagatg-
gaaagtttcatgggcaacgtttaaatgatgtcatcttaacttatgttg
cttcaactggtaaaatgagagca-
gaatatgctggtaaaacttgggagacttcaataacagatttaggtttatcaaaaa
tcaggcatataatttcttaatta-
catcagtcaaagatggggccttaatcaagggataaatgcaaatggctggatgaga
actgacttgaaaggttcagagtttactttacaccagaagcgccaaaaacaataacagaaftagaaaaaaagttg aagagattccattcaagaaagaacgtaaatttaatccggatttagcaccagggacagaaaaagtaacaagagaaggacaaaaggtgagaagacaataacgacaccaacactaaaaaatccattaactggagtaattattagtaaaggt gaaccaaaagaagagattacaaaagatccgattaatgaattaacagaatacggacctgaaacaatagcgccagtcatcgagacgaatttgatccgaagttaccaacaggagagaaagaggaagttccaggtaaaccaggaattaag aatccagaaacaggagacgtagttagaccgccggtcgatagcgtaacaaaatatggacctgtaaaaggagactcgattgtagaaaagaagagattccattcgagaaagaacgtaaactaatcctgamagcaccagggacagaaaaa gtaacaagagaaggacaaaaggtgagaagacaataacgacgccaacactaaaaaatccattaactggagaattattagtaaaggtgaatcgaaagaagaaatcacaaaagatccgattaatgaattaacagaatacggaccagaa acgataacaccaggtcatcgagacgaatttgatccgaagttaccaacaggagagaaagaggaagttccaggtaaaccaggaattaagaatccagaaacaggagatgtagttagaccaccggtcgatagcgtaacaaaatatggacctgt aaaaggagactcgattgtagaaaagaagagattccattcgagaaagaacgtaaatttaatcctgatttagcaccagggacagaaaaagtaacaagagaaggacaaaaggtgagaagacaataacgacaccaacactaaaaaatc cattaactgagtaattattagaaggtgaaccaaaagaaatcacaaaagatccgattaatgaattaacagaatacggaccagaaacgataacaccaggtcatggagacgaatttgatccgaagttaccaacaggagagaaagaa gaagttccaggtaaaccaggaattaagaatccagaaacaggagacgtagttagaccaccggtcgatagcgtaacaaaatatggacctgtaaaaggagactcgattgtagaaaagaagagattccattcaagaaagaacgtaaatttaat ccggatttagcaccagggacagaaaaagtaacaagagaaggacaaaaggtgagaagacaataacgacgccaacactaaaaaatccattaactggagaaattattagtaaaggtgaatcgaaagaagaaatcacaaaagatccgattaatgaattaacagaatacggaccagaaacgataacaccaggtcatcgagacgaatttgatccgaagttaccaacaggagagaaagaggaagttccaggtaaaccaggaattaagaatccagaaacaggagacgtagttagaccaccggtcgatagcgtaacaaaatatggacctgtaaaaggagactcgattgtagaaaagaagagattccattcgagaaagaacgtaaatttaatcctgaatagcaccagggacagaaaaagtaacaagagaaggacaaaaggtgagaagacaataacgacgccaacactaaaaaatccattaactggagaaattattagtaaaggtgaatcgaaagaagaaatcacaaaagatccgattaatgaattaacagaatacggaccagaaacgataacaccaggtcatcgagacgaatttgatccgaagttaccaacaggagagaaagaggaagttccaggtaaaccaggaattaagaatccagaaacaggagacgtagttagaccaccggtcgatagcgtaacaaaatatggacctgtaaaaggagactcgattgtagaaaagaagaaattccattcgagaaagaacgtaaatttaatcctgatttagcaccagggacagaaaaagtaacaagagaaggacaaaaggtgagaagacaataacgacgccaacactaaaaaatccattaactggagaattattagt aaaggtgaatcgaaagaagaaatcacaaaagatcgattaatgaattaacagaatacggaccagaaacgataacaccaggtcatcgagacgaatttgatccgaagttaccaacaggagagaagaggaagttccaggtaaaccagga attaagaatccagaaacaggagatgtagttagaccaccggtcgattgtagaaaagaagaaattccattcgagaaagaacgtaaatttaatcctgatttagcaccagggacag aaaaagtaacaagagaaggacaaaaggtgagaagacaataacgacgccaacactaaaaaatccattaactggagaaattattagtaaaggtgaatcgaaagaagaaatcacaaaagatccagttaatgaattaacagaattcggtggcgagaaaataccgcaaggtcataaagatatctttgatccaaacttaccaacagatcaaacggaaaaagtaccagg taaaccaggaatcaagaatccagacacaggaaaagtgatcgaagagccagtggatgatgtgattaaacacggaccaaaaacgggtacaccagaaacaaaaacagtagagataccgtttgaaacaaaacgtgagtttaatccaaaatt acaacctggtgaagagcgagtgaaacaagaaggacaaccaggaagtaagacaatcacaacaccaatcacagtgaacccattaacaggtgaaaaagttggcgagggtcaaccaacagaagagatcacaaaacaaccagtagataagattgtagagttcggtggagagaaaccaaaagatccaaaaaggacctgaaaacccagagaagccgagcagaccaactcatccaagtggcccagtaaatcctaacaatccaggattatcgaaagacagagcaaaaccaaatggcccagttcattcaatgataaaaatgataaagttaaaaaatctaaaattgctaaagaatcagtagctaatcaagagaaaaaacgagcagaattaccaaaaacaggtttagaaagcacgcaaaaaggttgatcttagtagtataattggaattgctggattaatgtattggctcgtagaagaaagaattaa
RrkN (8325) (SEQ ID NO:14)
SGKYGKRSMQMRDKKGPVNKRVDFLSN KLNKYSIRKFTVGTASILIGSLMYLGTQ QEAEAAENNIENPTTLKDNVQSKEVKIEEVTNKDTAPQGVEAKSEVTSNKDTIEHEPSVKAEDISKKEDTPKEVADVAEVQPKSSVTHNAETPKVRKARSVDEGSFDITRDSKNWESTPITIQGKEHFEGYGSVDIQKKPTDLGVSEVTRFNVGNESNGLIGALQLKNKIDFSKDFNFKVRVANNHQSNTTGADGWGFLFSKGNAEEYLTNGGILGDKGLVN SGGFKIDTGYIYTSSMDKTEKQAGQGYRGYGAFVKNDSSGNSQMVGENIDKSKT NFLNYADNSTNTSDGKFHGQRLNDVILTYVASTGKMRAEYAGKTWETSITDLGLSKNQAYNFLITSSQRWGLNQGINANGWMRTDLKGSEFTFTPEAPKTITELEKKVEEI PFKKERKFNPDLAPGTEKVTREGQKGEKTITTPTLKNPLTGVIISKGEPKEEITKDPINELTEYGPETIAPGHRDEFDPKLPTGEKEEVPGKPGIKNPETGDWRPPVDSVTKY GPVKGDSIVEKEEIPFEKERKFNPDLAPGTEKVTREGQKGEKTITTPTLKNPLTGEIISKGESKEEITKDPINELTEYGPETITPGHRDEFDPKLPTGEKEEVPGKPGIKNPETG DWRPPVDSVTKYGPVKGDSIVEKEEIPFEKERKFNPDLAPGTEKVTREGQKGEKTITTPTLKNPLTGVIISKGEPKEEITKDPINELTEYGPETITPGHRDEFDPKLPTGEKE EVPGKPGIKNPETGDWRPPVDSVTKYGPVKGDSIVEKEEIPFKKERKFNPDLAPGTEKVTREGQKGEKTITTPTLKNPLTGEIISKGESKEEITKDPINELTEYGPETITPGH RDEFDPKLPTGEKEEVPGKPGIKNPETGDWRPPVDSVTKYGPVKGDSIVEKEEIPFEKERKFNPDLAPGTEKVTREGQKGEK TITTPTLKNPLTGEIISKGESKEEITKDPIN ELTEYG-
PETITPGHRDEFDPKLPTGEKEEVPGK-
PGIKNPETGDWRPPVDSVTKYG
PVKGDSIVEKEEIPFKKERKFNPD-
LAPGTEKVTREGQKGEKTITTPTLKNPLTGEIIS
KGESKEEITKDPINELTEYGPETITPGH-
RDEFDPKLPTGEKEEVPGKPGIKNPETGD WRPPVDS-
VTKYGPVKGDSIVEKEEIPFEKERKFNP-
DLAPGTEKVTREGQKGEKTI
TTPTLKNPLTGEIISKGESKEEITKD-
PINELTEYGPETITPGHRDEFDPKLPTGEKEE VPGK-
PGIKN PETGDWRPPVDSVTKYGPVKGDSIVE-
KEEIPFEKERKFNPDLAPGT
EKVTREGQKGEKTITTPTLKNPLTGEI-
ISKGESKEEITKDPVNELTEFGGEKIPQGH KDIFDPN-
LPTDQTEKVPGKPGIKNPDT-
GKVIEEPVDDVIKHGPKTGTPETKTVEIPF
ETKREFNPKLQPGEERVKQEGQPGSK-
TITTPITVNPLTGEKVGEGQPTEEITKQPV
DKIVEFGGEKPKDPKGPENPE-
KPSRPTHPSGPVNPNNPGLSKDRAKPNGPVHSM
DKNDKVKKSKIAKESVANQEKKRAELPK-
TGLESTQKGLIFSSIIGIAGLMLLARRRK N
KnkA (8325) (SEQ ID NO:15)

ggaaggagtatgttgatggctaaatatc-
gagggaaaccgtttcaattatatgtaaagttatcgtgttcgacaatgatggc
gacaagtatcattttaacgaatatct-
tgccgtacgatgcccaagctgcatctgaaaaggatactgaaattacaaaaga
gatattatctaagcaagatttataga-
caaagttgacaaggcaattcgtcaaattgagcaattaaaacagttatcggctt
catctaaagaacattataaagcacaac-
taaatgaagcgaaaacagcatcgcaaatagatgaaatcataaaacga gctaat-
gagttggatagcaaagacaataaaagt-
tctcacactgaaatgaacggtcaaagtgatatagacagtaaatt
agatcaattgcttaaagatttaaatgag-
gtttctcaaatgttgataggggtcaacaaagtggcgaggacgatcttaat gcaat-
gaaaaatgatatgtcacaaacggcta-
caacaaaacatggagaaaaagatgataaaaatgatgaagca
atggtaaataaggcgttagaagaccta-
gaccatttgaatcagcaaatacacaaatcgaaagatgcatcgaaagat acatcg-
gaagatccagcagtgtctacaaca-
gataataatcatgaagtagctaaaacgccaaataatgatggttatg
gacatgttgtgttaaataaattc-
ctttcaaatgaagagaatcaaagccatagtaatcgactcactgataaattacaagg
aagcgataaaattaatcatgctatgat-
tgaaaaattagctaaaagtaatgcctcaacgcaacattacacatatcataa act-
gaatacgttacaatctttagatcaacg-
tattgcaaatacgcaacttcctaaaaatcaaaaatcagacttaatgagc
gaagtaaataagacgaaagagcg-
tataaaaagtcaacgaaatattattttggaagaacttgcacgtactgatgata
aaaagtatgctacacaaagcatttta-
gaaagtatatttaataaagacgaggcagttaaaattctaaaagatatacgt
gttgatggtaaaacagatcaacaaatg-
cagatcaaattactcgtcatattgatcaattatctctgacaacgagtgatg atttat-
taacgtcattgattgatcaatcacaa-
gataagtcgctattgatttctcaaattttacaaacgaaattaggaaaag
ctgaagcagataaattggctaaagattg-
gacgaataaaggattatcaaatcgccaaatcgtgaccaattgaagaa acattttg-
catcaactggcgacacgtcttcagat-
gatatattaaaagcaattttgaataatgccaaagataaaaaaca
agcaattgaaacgatttttagcaacacg-
tatagaaagacaaaaggcaaaattactggcagatttaattactaaaata gaaaca-
gatcaaaataaattttaatttagt-
taaatcggcattgaatggtaaagcggatgatttattgaatttacaaaa
gagactcaatcaaacgaaaaaagatata-
gattatattttatcaccaatagtaaatcgtccaagtttactagatcgattg
aataaaaatgggaaaacgacagatttaaataagttagcaaatttaatgaatcaaggatcagatttattagacagtatt cca-
gatatacccacaccaaagccagaaaa-
gacgttaacacttggtaaaggtaatggattgttaagtggattattaaa
tgctgatggtaatgtatctttgc-
ctaaagcgggggaaacgataaaagaacattggttgccgatatctgtaattgttggtg
caatgggtgtactaatgatttggttat-
cacgacgcaataagttgaaaaataaagcataa
KnkA (8325) (SEQ ID NO:16)

GRSMLMAKYRGKPFQLYVKLSCSTM-
MATSIILTNILPYDAQMSEKDTEITKEILSK QDLLD-
KVDKAIRQIEQLKQLSASSKEHYKAQL-
NEAKTASQIDEIIKRANELDSKDNK
SSHTEMNGQSDIDSKLDQLLKDLNEVSS-
NVDRGQQSGEDDLNAMKNDMSQTATT KHGEKD-
DKNDEAMVNKALEDLDHLNQQIHKSK-
DASKDTSEDPAVSTTDNNHEVA
KTPNNDGSGHWLNKFLSNEENQSHSNR-
LTDKLQGSDKINHAMIEKLAKSNASTQ HYTYH-
KLNTLQSLDQRIANTQLPKNQKSDLM-
SEVNKTKERIKSQRNIILEELARTDD
KKYATQSILESIFNKDEAVKILKDIRVDGKTDQQIA
DQITRHIDQLSLTTSDDLLTSLID QSQDKSLLISQILQT-
KLGKAEADKLAKDWTNKGLSNR-
QIVDQLKKHFASTGDTSSD DILKAILNNAKDKKQAI-
ETILATRIERQKAKLLADLITKIETDQNKIFNLVK
SALNGKAD DLLNLQKRLNQTKKDIDYILSPIVN-
RPSLLDRLNKNGKTTDLNKLANLMNQGSDLLD SIP-
DIPTPKPEKTLTLGKGNGLLS-
GLLNADGNVSLPKAGETIKEHWLPISVIVGAMG
VLMIWLSRRNKLKNKA

Primary Structure Analysis

Figure 1:
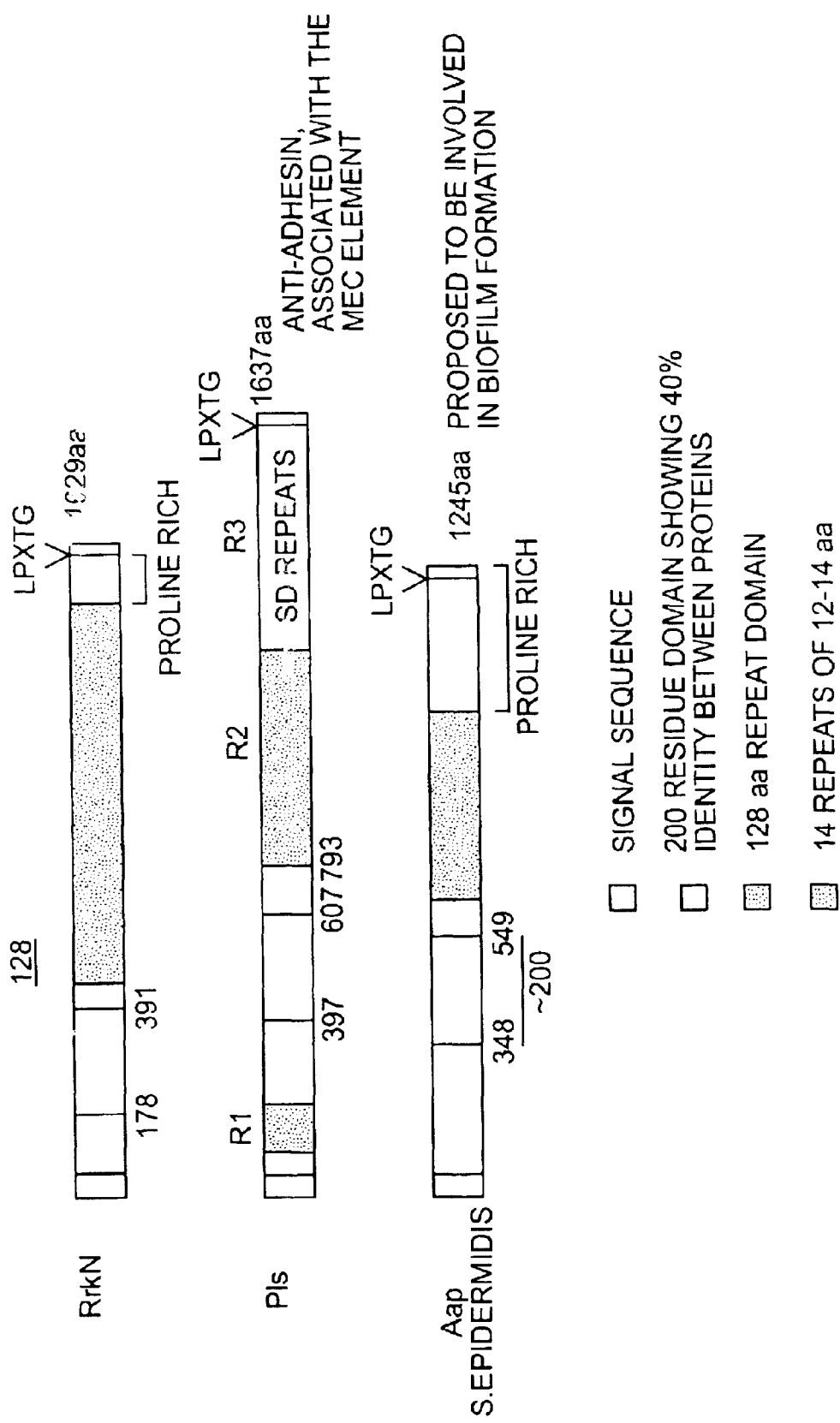
FIG. 1 is a depiction of the primary structure of the in silico-predicted proteins in accordance with the present invention.
Figure 1:
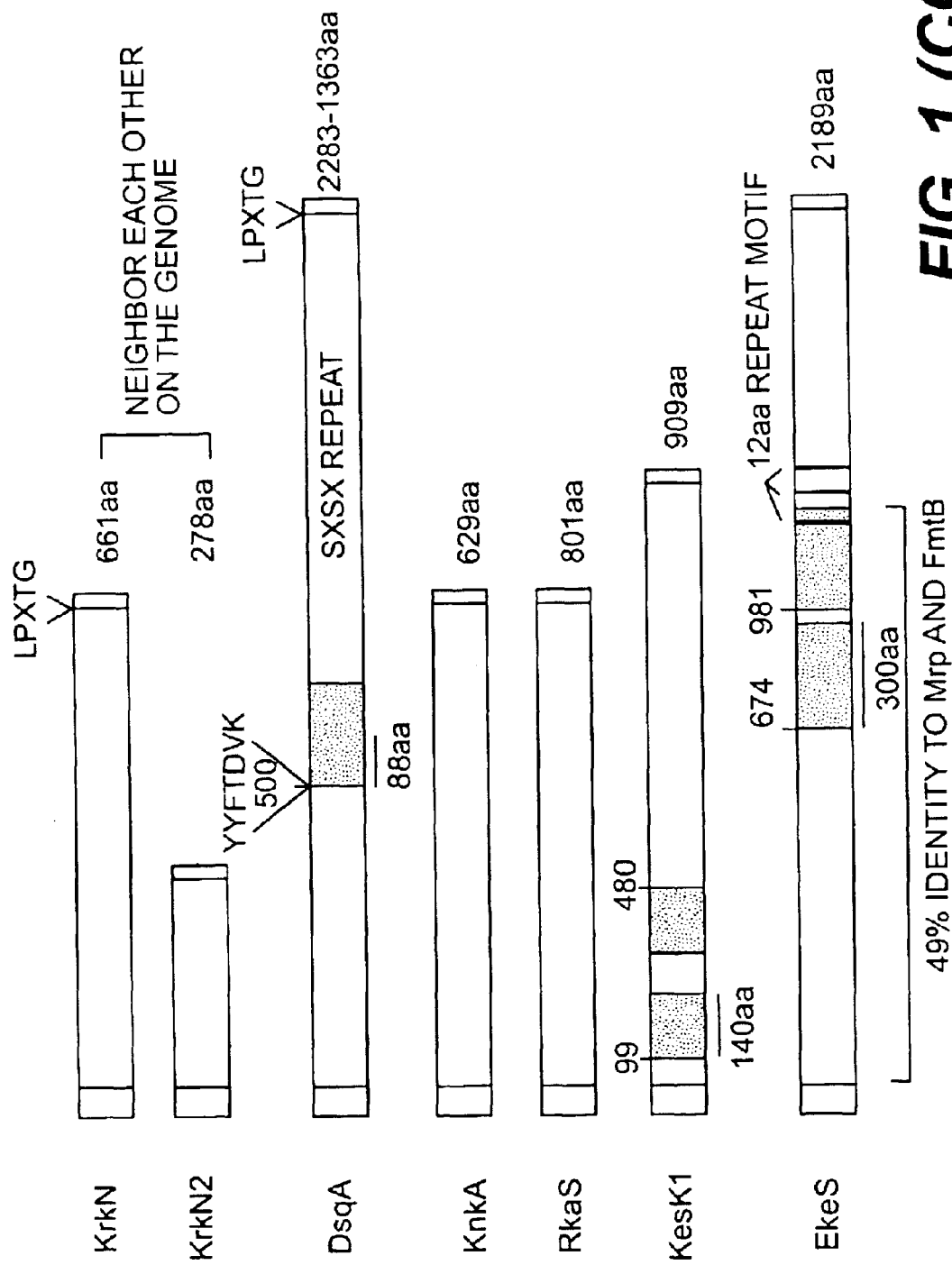

A bioinforrnatic approach was used for primary structure and function prediction (FIG. 1). Proteins RrkN and DsqA possessed a similar structural organization to previously described MSCRAMMs. RrkN is similar in structure to the PIs/Aap proteins of S. aureus and S. epidermidis, respectively. It contains a 200-residue domain at its N-terminus showing 40% identity to PIs and Aap. The C-terminus of the protein is predominantly composed of a 128 residue repeat domain, which varies in the numbers of repeats from strain to strain. These repeats are also present in PIs and Aap. A putative sar homolog and fnbpA and fnbpB lie directly upstream from RrkN on the genome.

DsqA is similar in structural organization to the Sdr family of proteins. It contains a typical A domain followed by a TYYFTDVK motif which is similar to a conserved TYTFTVYVD motif found in all of the Sdr proteins. The function of this motif has yet to be determined. Two 88 residue repeat domains reside in the centre of the protein followed by a C-terminal SX-repeat motif similar to the SD-repeat motif found in the Sdr proteins. The size of this repeat varies from strain to strain. DsqA neighbors secY and secA on the genome. A DsqA homolog (>90% identical) is also found in S. epidermidis.

KnkA contains no repeat domains in its sequence. Secondary structure prediction analysis indicate that this protein is predominantly composed of alpha-helices.

RkaS contains no repeat domains in its sequence. BLAST analysis indicates that it is similar to a 5' nucleotidase UDP-sugar hydrolase. The gene encoding RkaS lies directly upstream from orfX, the insertion site of the mec element.

KesK contains two 140 residue repeat domains at the N-terminus of the protein which are 38% identical. Hydropathy plot analysis (Kyte and Doolittle, 1982) indicates that there is a large hydrophilic domain in the center of the protein (residue 500–560).

EkeS contains two 300 residue repeat domains in the center of the protein which are 38% identical. Blast analysis indicates that the N-terminus of the protein (residues 1–1268, bearing both repeats) is 49% identical to FmtB, an LPXTG protein with 17 tandem repeats. FmtB is proposed to be involved indirectly in methicillin resistance as inactivation of fmtB abolishes methicillin resistance. This appears to be due to affecting cell wall composition as methicillin sensitivity can be relieved by increasing the production of the cell wall precursor glucosamine-1-phosphate (Komatsuzawa et al., 2000).

KrkN and KrkN2 neighbor each other on the genome.

Figure 2:
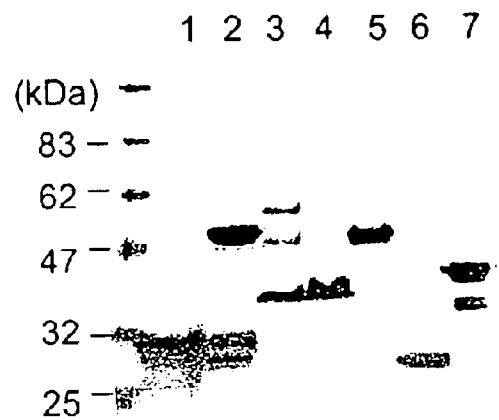
FIG. 2 shows a Coomassie gel of the purified N-terminal recombinant His-tagged proteins expressing the orfs of the present invention.
Figure 3A:
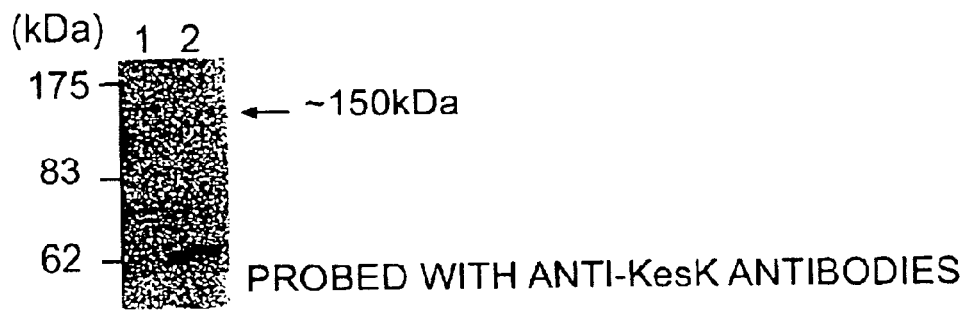
FIGS. 3A-3C show Western blotting of S. aureus cell wall extracts showing robing with anti-KesK antibodies (FIG. 3A), anti-KnkA antibodies (FIG. 3B) and anti-DsqA antibodies (FIG. 3C), respectively.
Figure 3B:
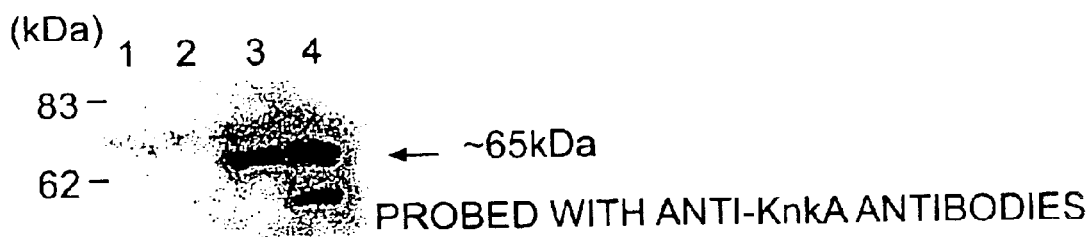
Figure 3C:
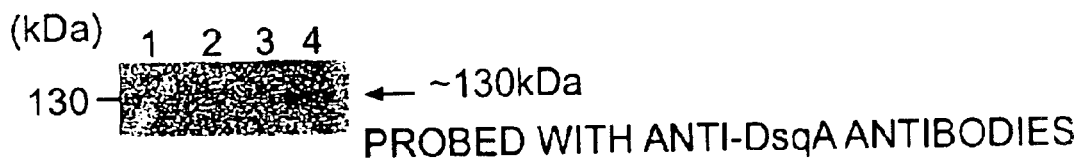

Expression Analysis:

Due to lack of sequence homology with protein databases, a putative function for each of these proteins could not be predicted and hence a molecular approach was taken. Unique regions of four of the orfs were expressed in E. coli as recombinant his-tagged fusion proteins using the Qiagen pQE-30 expression system. FIG. 2. represents a Coomassie stained SDS-PAGE gel of the purified N-terminal his-tag fusion proteins. The recombinant proteins RrkN1, DsqA2, KesK1 and KnkA were used to generate antibodies in rabbits. Western blotting analysis of S. aureus cell wall extracts revealed that KesK, KnkA and DsqA are expressed and cell wall-associated (FIG. 3). Strain eMRSA-16 represents a knka-negative strain since it lacks the knka gene. An immunoreactive band of 65 kDa reacts with the cell wall fraction from both exponential and stationary phase cells of strain 8325-4 (FIG. 3, B). The absence of this band in strain eMRSA-16 suggests that it represents the gene product of knka.

Western immunoblotting of the cell wall fraction of strain 8325-4 using anti-KesK antibodies identified a 150 kDa immunoreactive band in both exponential and stationary phase cultures. A similar sized immunoreactive protein released from the cell wall fraction of Lactococcus lactis expressing full length KesK on an expression plasmid (pKS80) suggests that the 150 kDa band represents the kesK gene product (data not shown). A kesK knockout mutant in S. aureus would be required to confirm the size of the cell wall-released KesK protein.

Western immunoblotting of the cell wall fraction of S. aureus strain MSSA and eMRSA-16 using anti-DsqA antibodies identified a 130 kDa immunoreactive band. Expression levels are higher in stationary phase cells.

Figure 4A:
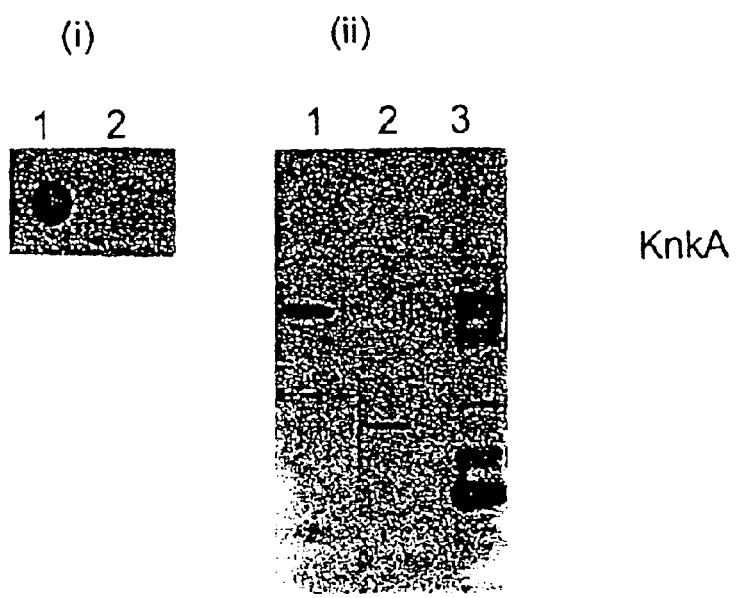
FIGS. 4A-4B show Dot-blotting and Western immunoblotting of *Lactococcus lactis* expressing *S. aureus* MSCRAMM®S, namely KnkA (FIG. 4A) and KesK (FIG. 4B).
Figure 4B:
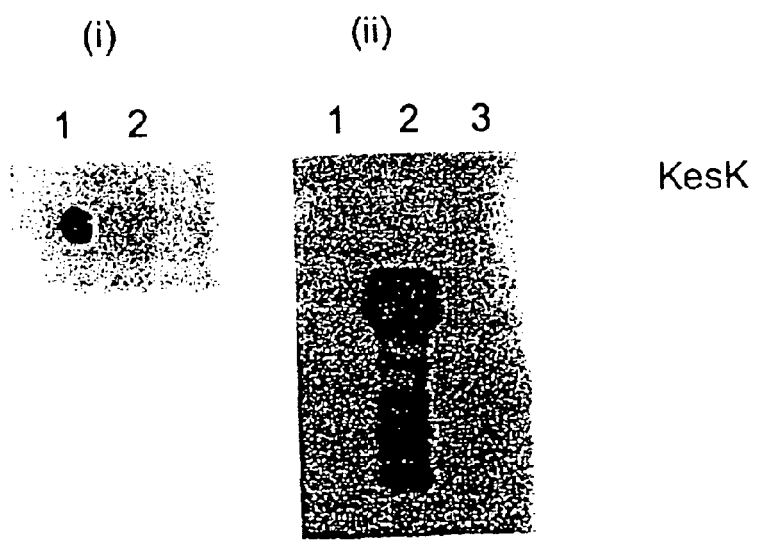

Heterologous Expression in Lactococcus lactis:

Heterologous expression of S. aureus surface proteins in Lactococcus lactis (L. lactis) has previously been used as a tool to study protein function (Sinha et al., 2000). In this study this surrogate system will be used to express each of the in silico-predicted MSCRAMMs on the surface of L. lactis to fish for a function. KesK and KnkA have been cloned into L. lactis and shown by dot blotting to be surface expressed (FIG. 4). No cross reaction was observed with the negative control (pKS80 plasmid without an insert) indicating that this is a specific reaction. Cell wall and protoplast fractions of Lactococcus lactis bearing pKS-KnkA and pKS-KesK were generated by digestion of cells with lysozyme and mutanolysin and used in Western blotting studies using anti-KnkA and anti-KesK antibodies, respectively. Unlike what was observed in S. aureus, KnkA was not detected in the cell wall fraction of L. lactis but found to be associated with the protoplast fraction. The anchoring motif of KnkA differs from the consensus LPXTG sequence in that it contains an Alanine residue instead of a Threonine (i.e. LPKAG) (Table 1). It has been recently been published that S. aureus contains two sortase genes, srtA and srtB (Pallen, 2001). It is possible that this variant form of the LPXTG motif is processed by the second sortase gene, which is absent in L. lactis. This would also explain the slight increase in size of the KnkA protein observed in the protoplast fraction, as the cell wall sorting signal has not been cleaved.

KesK was detected in the cell wall fraction of L. lactis but migrated at a smaller molecular weight than the KesK protein released from the cell wall of S. aureus. The majority of MSCRAMMs expressed on the surface of L. lactis are prone to proteolysis during the cell wall extraction procedure (Louise O'Brien, personal communication). Therefore, it is possible that the KesK protein released from the surface of L. lactis represents a truncated form of KesK. Shorter digestion times with lysozyme and mutanolysin has been shown to limit the extent of proteolysis.

Expression of in Silico-Predicted MSCRAMMs in Vivo:

Convalescent-phase sera from 33 patients recovering from S. aureus infections were tested in their ability to recognize the purified N-terminal his-tag fusion proteins in an ELISA assay. Pooled sera from children and healthy blood donors were used as negative controls. A positive reaction was taken as a value equal to or greater than twice the value of the negative control. FIGS. 5A-5D illustrate that all of the proteins were recognized by 27–42% of the patients suggesting that these proteins are expressed in vivo and are immunogenic during infection of the host.

References:

Komatsuzawa, H., Ohta, K., Sugai, M., Fujiwara, T., Glanzmann, P., Berger-Bachi, B., Suginaka, H. (2000) Tn551-mediated insertional inactivation of the fmtB gene encoding a cell wall-associated protein abolishes methicillin resistance in Staphylococcus aureus. J. Antimicrob. Chemother. 45: 421–31.

Sinha, B., Francois, P., Que, Y. A., Hussain, M., Heilmann, C., Moreillon, P., Lew, D., Krause, K. H., Peters, G., Herrmann, M. (2000) Heterologously expressed Staphylococcus aureus fibronectin-binding proteins are sufficient for invasion of host cells.

Infect. Immun. 68: 6871–6878.

Pallen, M. J., Lam, A. C., Antonio, M., Dunbar, K. (2000) An embarrassment of sortases—a richness of substrates? Trends. Microbiol. 9: 97–101

Example 2

Isolation and Sequencing of Cross-Reactive Proteins from S. Aureus and from Coagulase-Negative Staphylococci It has been recently shown that S. epidermidis contains surface proteins structurally related to S. aureus MSCRAMM® proteins (U.S. Ser. No. 09/386,962). One protein from S. aureus is of particular interest since it has a close homologue in S. epidermidis. The protein is called DsqA or SasA (S. aureus) and DgsK (S. epidermidis). They are characterized by a typical "A" domain of approximately 500 amino acid residues, followed by two B repeats of 88 residues that are ~40% identical, and a unique SXSX dipeptide repeat that can vary in length depending on the strain. Contained within the A domain of the S. aureus DsqA/SasA is a 180 residue region that has ~40% identity to a similar sized domain within region A of S. aureus proteins RrkN, PIs and S. epidermidis protein Aap The A regions of the DsqA/SasA and DgsK proteins are 46% identical at the amino acid level, the BB repeats are 50% identical. Active and passive immunization strategies that include; vaccines, polyclonal and monoclonal antibodies recognizing both *S. aureus* and coagulase-negative staphylococcal proteins are the subject of this invention.

Specific Examples of Antibodies that Cross-React with Coagulase-Negative Staphylococci and *S. aureus*.

Coagulase-negative Staphylococcal DgsK A-Domain:

Amino Acid Sequence (SEQ ID NO:17) ASETPIT-SEISSNSETVANQNSTTIKN-SQKETVNSTSLESNHSNSTNKQMSSEVTN TAQSSEK-AGISQQSSETSNQSSKLNTYASTDHVESTTINND NTAQQDQNKSSNVT SKSTQSNTSSSEKNISSNLTQSI-ETKATDSLATSEARTSTNQISTNLTSTSTSNQSSP TSFANLRTFSRFTVLNTMAAPTTTSTTI-ISSLTSNSVVVNKDNFNEHMNLSGSATY DPKT-GIATLTPDAYSQKGAISLNTRLDSNRS-FRFIGKVNLGNRYEGYSPDGVAGGD GIGFAFSPGPLGQIGKEGAAVGIG-GLNNAFGFKLDTYHNTSTPRSDAKAKADPRN VGGGGAFGAFVSTDRNGMATTEESTMKL-NVQPTDNSFQDFVIDYNGDTKVMTV TYAGQTFTRN-LTDWIKNSGGTTFSLSMTASTGGAKN-LQQVQFGTFEYTESAVAKV RYVDANTGKDIIPPKTIAGEVDGTVNID-KQLNNFKNLGYSYVGTDALKAPNYTETSG TPTLKLTNSSQTVIYKFKDVQ

*S. aureus* SasA A-domain:

Amino Acid Sequence (SEQ ID NO:18) ASDAPLT-SELNTQSETVGNQNSTTIEASTS-TADSTSVTKNSSSVQTSNSDTVSSEK SEKVTSTT-NSTSNQQEKLTSTSESTSSKNTTSSSDTKSVASTS STEQPINTSTNQS TASNNTSQSTTPSSVNLNKTSTTST-STAPVKLRTFSRLAMSTFASAATTTAVTANTI TVNKDNLKQYMTTSGNATYDQST-GIVTLTQDAYSQKGAITLGTRIDSNKSFHFSGK VNLGNKYEGHGNGGDGIGFAFSPGV-LGETGLNGMVGIGGLSNAFGFKLDTYHNT SKPNSM-KANADPSNVAGGGAFGAFVTTDSYGVAT-TYTSSSTADNMKLNVQPT NNTFQDFDINYNGDTKVMTVKY-AGQTWTRNISDWIAKSGTTNFSLSMTASTGGAT NLQQVQFGTFEYTESAVTQVRYVDVT-TGKDIIPPKTYSGNVDQVVTIDNQQSALTA KGYNY-TSVDSSYASTYNDTNKTVKMTNAGQSVTYYFTDW The entire sequence of the Aap protein and the DNA coding therefor (with an indication of the presence of the A domain) is shown below:

*S. epidermidis* Aap Protein (A-domain Underlined) (SEQ ID NO:19)

MGKRRQGPINKKVDFLPNKLNKYSIRKFTVGTASILLGSTLIFGSSSHEAKAAE<u>EKQ</u>

<u>VDPITQANQNDSSERSLENTNQPTVNNEAPQMSSTLQAEEGSNAEAPQSEPTKA</u>

<u>EEGGNAEAAQSEPTKAEEGGNAEAPQSEPTKAEEGGNAEAAQSEPTKTEEGSNV</u>

<u>KAAQSEPTKAEEGSNAEAPQSEPTKTEEGSNAKAAQSEPTKAEEGGNAEAAQSE</u>

<u>PTKTEEGSNAEAPQSEPTKAEEGGNAEAPQSEPTKTEEGGNAEAPNVPTIKANSD</u>

<u>NDTQTQFSEAPTRNDLARKEDIPAVSKNEELQSSQPNTDSKIEPTTSEPVNLNYSS</u>

<u>PFMSLLSMPADSSSNNTKNTIDIPPTTVKGRDNYDFYGRVDIESNPTDLNATNLTR</u>

<u>YNYGQPPGTTTAGAVQFKNQVSFDKDFDFNIRVANNRQSNTTGADGWGFMFSK</u>

<u>KDGDDFLKNGGILREKGTPSAAGFRIDTGYYNNDPLDKIQKQAGQGYRGYGTFVK</u>

<u>NDSQGNTSKVGSGTPSTDFLNYADNTTNDLDGKFHGQKLNNVNLKYNASNQTFT</u>

<u>ATYAGKTWTATLSELGLSPTDSYNFLVTSSQYGNGNSGTYASGVMRADLDGATL</u>

TYTPKAVDGDPIISTKEIPFNKKREFDPNLAPGTEKVVQKGEPGIETTTTPTYVNPN

TGEKVGEGEPTEKITKQPVDEIVHYGGEEIKPGHKDEFDPNAPKGSQTTQPGKPG

VKNPDTGEVVTPPVDDVTKYGPVDGDPITSTEEIPFDKKREFNPDLKPGEERVKQ

KGEPGTKTITTPTTKNPLTGEKVGEGEPTEKITKQPVDEITEYGGEEIKPGHKDEFD

PNAPKGSQEDVPGKPGVKNPGTGEVVTPPVDDVTKYGPVDGDPITSTEEIPFDKK

REFNPDLKPGEERVKQKGEPGTKTITTPTTKNPLTGEKVGEGEPTEKITKQPVDEI

VHYGGEQIPQGHKDEFDPNAPVDSKTEVPGKPGVKNPDTGEVVTPPVDDVTKYG

PVDGDSITSTEEIPFDKKREFDPNLAPGTEKVVQKGEPGTKTITTPTTKNPLTGEKV

GEGKSTEKVTKQPVDEIVEYGPTKAEPGKPAEPGKPAEPGKPAEPGTPAEPGKPA

EPGTPAEPGKPAEPGKPAEPGKPAEPGKPAEPGTPAEPGTPAEPGKPAEPGTPA

EPGKPAEPGTPAEPGKPAESGKPVEPGTPAQSGAPEQPNRSMHSTDNKNQLPD

TGENRQANEGTLVGSLLAIVGSLFIFGRRKKGNEK

S. epidermidis aap DNA (SEQ ID NO:20)

atgggcaaac gtagacaagg tcctattaat aaaaaagtgg atttttttacc taacaaatta aacaagtatt ctataagaaa attcactgtt ggtacggcct caatattact tggttcgaca cttatttttg gaagtagtag ccatgaagcg aaagctgcag aagaaaaaca agttgatcca attacacaag ctaatcaaaa tgatagtagt gaaagatcac ttgaaaacac aaatcaacct actgtaaaca atgaagcacc acagatgtct tctacattgc aagcagaaga aggaagcaat gcagaagcac ctcaatctga gccaacgaag gcagaagaag gaggcaatgc agaagcagct caatctgagc caacgaaggc agaagaagga ggcaatgcag aagcacctca atctgagcca acgaaggcag aagaaggagg caatgcagaa gcagctcaat ctgagccaac gaagacagaa gaaggaagca acgtaaaagc agctcaatct gagccaacga aggcagaaga aggaagcaat gcagaagcac ctcaatctga gccaacgaag acagaagaag gaagcaacgc aaaagcagct caatctgagc caacgaaggc agaagaagga ggcaatgcag aagcagctca atctgagcca acgaagacag aagaaggaag caatgcagaa gcacctcaat ctgagccaac gaaggcagaa gaaggaggca atgcagaagc acctcaatct gagccaacga agacagaaga aggaggcaat gcagaagcac cgaatgttcc aactatcaaa gctaattcag ataatgatac acaaacacaa ttttcagaag cccctacaag aaatgaccta gctagaaaag aagatatccc tgctgtttct aaaaacgagg aattacaatc atcacaacca aacactgaca gtaaaataga acctacaact tcagaacctg tgaatttaaa ttatagttct ccgtttatgt ccttattaag catgcctgct gatagttcat ccaataacac taaaaataca atagatatac cgccaactac ggttaaaggt agagataatt acgatttta cggtagagta gatatcgaaa gtaatcctac agatttaaat gcgacaaatt taacgagata taattatgga cagccacctg gtacaacaac agctggtgca gttcaattta aaaatcaagt tagttttgat aaagatttcg actttaacat tagagtagca aacaatcgtc aaagtaatac aactggtgca gatggttggg gctttatgtt cagcaagaaa gatggggatg atttcctaaa aaacggtggt atcttacgtg aaaaaggtac acctagtgca gctggtttca gaattgatac aggatattat aataacgatc cattagataa aatacagaaa caagctggtc aaggctatag agggtatggg acatttgtta aaaatgactc ccaaggtaat acttctaaag taggatcagg tactccatca acagattttc ttaactacgc agataatact actaatgatt tagatggtaa attccatggt caaaaattaa ataatgttaa tttgaaatat aatgcttcaa atcaaacttt tacagctact tatgctggta aaacttggac ggctacgffa tctgaattag gattgagtcc aactgatagt tacaatttt tagttacatc aagtcaatat ggaaatggta atagtggtac atacgcaagt ggcgttatga gagctgattt agatggtgca acattgacat acactcctaa agcagtcgat ggagatccaa ttatatcaac taaggaaata ccatttaata agaaacgtga atttgatcca aacttagccc caggtacaga aaaagtagtc caaaaaggtg aaccaggaat tgaaacaaca acaacaccaa cttatgtcaa tcctaataca ggagaaaaag ttggcgaagg tgaaccaaca gaaaaaataa caaaaaaacc agtggatgaa atcgttcatt atggtggcga agaaatcaag ccaggccata aggatgaatt tgatccaaat gcaccgaaag gtagtcaaac aacgcaacca ggtaagccgg gggttaaaaa tcctgataca ggcgaagtag ttactccacc tgtggatgat gtgacaaaat atggtccagt tgatggagat ccgatcacgt caacggaaga aattccattc gacaagaaac gtgaattaac cctgacaag aacgcaacca cgtcaacgg aagaaattcc attcgacaag aaacgtgaat caatcctga tttaaaacca ggtgaagagc gcgttaaaca gaaaggtgaa ccaggaacaa aaacaattac aacgccaaca actaagaacc cattaacagg agaaaaagtt ggcgaaggtg aaccaacaga aaaaataaca aaacaaccag tggatgagat tgttcattat ggtggtgaac aaataccaca aggtcataaa gatgaattg atccaaatgc acctgtagat agtaaaactg aagttccagg taaccagga gttaaaaatc ctgatacagg tgaagttgtt accccaccag tggatgatgt gacaaaatat ggtccagttg atggagattc gattacgtca acggaagaaa ttccgtttga taaaaacgc gaatttgatc caaacttagc gccaggtaca gagaaagtcg ttcaaaaagg tgaaccagga acaaaaacaa ttacaacgcc aacaactaag aacccattaa caggagaaaa agttggcgaa ggtaaatcaa cagaaaaagt cactaaaaca cctgttgacg aaattgttga gtatggtcca acaaaagcag aaccaggtaa accagcggaa ccaggtaaac cagcggaacc aggtaaacca gaggaaccag gtacgccagc agaaccaggt aaaccagcgg aaccaggtac gccagcagaa ccaggtacgc cagcagaacc aggtaaacca gcggaaccag aaccaggtac gccagcagaa ccaggtaaac cagcggaatc aggtaaacca gtggaaccag gtacgccagc acaatcaggt gcaccagaac aaccaaatag atcaatgcat tcaaaagata ataaaaatca attacctgat acaggtgaaa atcgtcaagc taatgaggga acttagtcg gatctctatt agcaattgtc ggatcattgt tcatatttgg tcgtcgtaaa aaaggtaatg aaaaataatt tcatataaaa acttctgcc attaa

A-Domain from S. epidermidis Aap (Amino Acids 55–600) (SEQ ID NO:21)

$^{55}$EKQVDPITQANQNDSSERSLENT-
NQPTVNNEAPQMSSTLQAEEGSNAEAPQSE
PTKAEEGGNAEAAQSEPTKAEEGGNAE-
APQSEPTKAEEGGNAEAAQSEPTKTEE GSNV-
KAAQSEPTKAEEGSNAEAPQSEPTK-
TEEGSNAKAAQSEPTKAEEGGNAEA
AQSEPTKTEEGSNAEAPQSEPTKAEEGG-
NAEAPQSEPTKTEEGGNAEAPNVPTIK ANS-
DNDTQTQFSEAPTRNDLARKEDI-
PAVSKNEELQSSQPNTDSKIEPTTSEPVNL
NYSSPFMSLLSMPADSSSNNTKNTID-
IPPTTVKGRDNYDFYGRVDIESNPTDLNAT
NLTRYNYGQPPGTTTAGAVQFKNQVSFD-
KDFDFNIRVANNRQSNTTGADGWGF MFSKKDGD-
DFLKNGGILREKGTPSAAGFRIDT-
GYYNNDPLDKIQKQAGQGYRGYG
TFVKNDSQGNTSKVGSGTPSTDFLNY-
ADNTTNDLDGKFHGQKLNNVNLKYNASN
QTFTATYAGKTWTATLSELGLSPTDSYN-
FLVTSSQYGNGNSGTYASGVMRADLD GA$^{600}$

Protein Production and Purification

Using PCR, the A domain of DgsK or SasA was amplified from the sequences described above and subcloned into the E. coli expression vector PQE-30 (Qiagen), which allows for the expression of a recombinant fusion protein containing six histidine residues. This vector was subsequently transformed into the E. coli strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size of 0.45 □m) and the cell paste frozen at −80° C. Cells were lysed in 1× PBS (10 mL of buffer/1 g of cell paste) using 2 passes through the French Press @ 1100 psi. Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0–100% gradient of 10 mM Tris, pH 8.0, 100 mM NaCl, 200 mM imidazole (Buffer B) over 30 column volumes. SdrGN1N2N3 or SdrGN2N3 eluted at ~13% Buffer B (~26 mM imidazole). Absorbance at 280 nm was monitored. Fractions containing SdrGN1 N2N3 or SdrGN2N3 were dialyzed in 1× PBS.

Each protein was then put through an endotoxin removal protocol. Buffers used during this protocol were made endotoxin free by passing over a 5-mL Mono-Q sepharose (Pharmacia) column. Protein was divided evenly between 4×15 mL tubes. The volume of each tube was brought to 9 mL with Buffer A. 1 mL of 10% Triton X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with 0.1M $NiCl_2$ to remove remaining detergent. The column was washed with 9 column volumes of Buffer A before the protein was eluted with 3 column volumes of Buffer B. The eluant was passed over a 5-mL Detoxigel (Sigma) column and the flow-through collected and reapplied to the column. The flow-through from the second pass was collected and dialyzed in 1× PBS. The purified product was analyzed for concentration, purity and endotoxin level before administration into the mice.

Monoclonal Antibody Production

*E. coli* expressed and purified recombinant SasA and DsgK proteins were used to generate a panel of murine monoclonal antibodies while the mouse sera was used as a source of polyclonal antibodies. Briefly, a group of Balb/C or SJL mice received a series of subcutaneous immunizations of 1–10 mg of protein in solution or mixed with adjuvant as described in the Table below.

Immunization Schemes

|  | Day | Amount (μg) | Route | Adjuvant |
|---|---|---|---|---|
| RIMMS Injection |  |  |  |  |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |
| Conventional Injection |  |  |  |  |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against MSCRAMM® proteins or on whole cells (*S. epidermidis* and *S. aureus*). Three days after the final boost, the spleens or lymph nodes were removed, teased into a single cell suspension and the lymphocytes harvested. The lymphocytes were then fused to a P3X63Ag8.653 myeloma cell line (ATCC #CRL-1580). Cell fusion, subsequent plating and feeding were performed according to the Production of Monoclonal Antibodies protocol from *Current Protocols in Immunology* (Chapter 2, Unit 2.).

Any clones that were generated from the fusion were then screened for specific anti-SasA antibody production using a standard ELISA assay. Positive clones were expanded and tested further for activity in a whole bacterial cell binding assay by flow cytometry and SasA binding by Biacore analysis.

Biacore Analysis

Throughout the analysis, the flow rate remained constant at 10 mV/min. Prior to the SasA or DgsK injection, test antibody was adsorbed to the chip via RAM-Fc binding. At time 0, SasA or DgsK at a concentration of 30 mg/ml was injected over the chip for 3 min followed by 2 minutes of dissociation. This phase of the analysis measured the relative association and disassociation kinetics of the Mab/SasA or DgsK interaction.

Binding to Whole Bacteria

Bacterial samples *S. aureus* Newman, *S. aureus* 67-0, *S. aureus* 397 (Sal6), *S. aureus* Wood, *S. aureus* 8325-4, methicillin resistant *S. aureus* MRSA 16, *S. epidermidis* ATCC 35984, *S. epidermidis* HB, *S. epidernidis* CN-899 and *S. haemolyticus* ATCC 43253 were collected, washed and incubated with Mab or PBS alone (control) at a concentration of 2 μg/ml after blocking with rabbit IgG (50 mg/ml). Following incubation with antibody, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured. These data indicate that antibodies against *S. aureus* SasA were able to recognize a homologous protein on the surface of coagulase-negative staphylococci. The data support Western blot analysis demonstrating that rabbit polyclonal antibodies against *S. aureus* SasA cross-react with a protein released from the cell surface of *S. epidermidis* HB as well as the recombinant A-region from DsgK cloned from *S. epidermidis* (see Table below and FIG. 6).

| | | | | Polyclonal Sera Reactivity | | | | | |
|---|---|---|---|---|---|---|---|---|---|
| | Newman | 67-0 | 397 (SAL 6) | Wood 46 | 8325-4 | MRSA 16 | ATCC 35984 | HB | CN-899 | ATCC 43253 |
| Normal Mouse Sera | − | − | − | − | − | − | − | − | − | − |
| Mouse anti-SasA | + | + | +/− | − | + | + | + | + | + | + |

What is claimed is:

1. An isolated antibody which specifically binds to a staphylococcal surface protein consisting essentially of the amino acid sequence of SEQ ID NO: 18.

2. The antibody according to claim 1 wherein the antibody is raised against the A domain of the surface protein.

3. The antibody according to claim 1, wherein the antibody is suitable for parenteral, oral, intranasal, subcutaneous, aerosolized or intravenous administration in a human or animal.

4. The antibody according to claim 1, wherein said antibody is a monoclonal antibody.

5. The antibody according to claim 1, wherein said antibody is a polyclonal antibody.

6. The antibody according to claim 4 wherein the monoclonal antibody is of a type selected from the group consisting of murine, chimeric, humanized and human monoclonal antibodies.

7. The antibody according to claim 4 wherein the antibody is a single chain monoclonal antibody.

8. An isolated antibody fragment which specifically binds to a staphylococcal surface protein consisting essentially of the amino acid sequence of SEQ ID NO: 18.

9. The antibody according to claim 1 that is raised against a protein having an amino acid sequence of SEQ ID NO: 18.

10. Isolated antisera containing an antibody according to claim 1.

11. A composition comprising the isolated antibody according to claim 1 and a physiologically acceptable antibiotic.

* * * * *

SEQUENCE LISTING

<160> NUMBER OF SEQ ID NOS: 29
<210> SEQ ID NO 1
<211> LENGTH: 6609
<212> TYPE: DNA
<213> ORGANISM: Staphylococcus epidermidis

<400> SEQUENCE: 1

| | | | | | |
|---|---|---|---|---|---|
| acaacacagc | agagaataga | caaccaggag | gaaaacgaaa | tgaatttgtt | aaagaaaaat | 60 |
| aaatatagta | ttagaaaata | taaagtaggg | atattctcta | ctttaatcgg | gacagtttta | 120 |
| ttactttcaa | acccaaatgg | tgcacaagct | taactacgg | atcataatgt | gcaaggtggt | 180 |
| tcaaatcaag | cattacctgg | caactcacaa | aatacaaatg | ccgatactaa | tcgagacata | 240 |
| gtaaatgatt | cgcaaaatac | tcctaatgca | catgcaacag | acaatacatc | aacaaatcaa | 300 |
| gcattgacta | atcatcaaaa | cgttgatgtg | gcaaatcaag | tcgggcctgc | tccaatacag | 360 |
| cctagcgcgt | cgcctgcgca | aaataataat | aattctaatg | ctaattcaac | agcaacagag | 420 |
| ccagcggcga | atacaaataa | taatttagca | tcaaataaca | atacattaaa | cgtgcctaat | 480 |
| aatacagata | acaatgattc | agcgcgtcat | ctgactttaa | aagaaattca | agaagatgtt | 540 |
| cgtcattcgt | ctgataagcc | agagttagtt | gcgattgctg | aagaagcatc | taatagaccg | 600 |
| aaaaagagaa | gcagacgtgc | tgcgccaaca | gatcctaatg | caacaccagc | agatccaacg | 660 |
| gctacaccag | cagatccaac | ggcaggaaat | ggtagtgcac | cagttgcaat | tacagcgcca | 720 |
| tacacgccaa | caactgatcc | caatgccaat | aatataggac | aaaatgcacc | taacgaagtg | 780 |
| ctttcatttg | atgataacaa | cattagacca | agtacgaacc | gttctgtgcc | tacagtaact | 840 |
| gttgttgata | atttaccagg | ctacacactg | attaatggtg | gtaaagtagg | ggtgtttagt | 900 |
| catgcaatgg | taagaacgag | catgtttgat | tcaggagatg | ccaagaacta | tcaagcgcaa | 960 |
| ggcaatgtaa | ttgcattggg | tcgtattaga | ggaaatgata | caaatgatca | tggcgatttt | 1020 |
| aatggtatcg | agaaaacatt | aacagtaaat | ccgaattctg | aattaatctt | tgaatttaat | 1080 |
| actatgacta | ctaaaaacta | tcaaggtatg | acaaatttaa | tcattaaaaa | tgctgataac | 1140 |
| gatactgtta | ttggtgaaaa | agtagttgct | tatggtccga | tttggcgctt | attaaaagta | 1200 |
| cctgaaaatg | ttagtcatct | aaaaattcaa | tttgtaccta | aaaatgacgc | aataacagat | 1260 |
| gcacgtggta | tttatcaatt | acgagatgga | tataaatact | atgactttgt | agactcaatc | 1320 |
| ggtcttcatt | ctgggtcaca | tgtctatgtt | gaaagacgta | caatggagcc | aacagcaaca | 1380 |
| aataataaag | aatttacagt | tacaacgtca | ttaaagaata | tggtaacttt | ggcgcttca | 1440 |
| ttcaatacag | atgattttgt | atataaaatt | caattacctg | aaggtgttga | atatgtaaat | 1500 |
| aattcattga | ctaaagattt | tcctagcggt | aattcaggtg | ttgatattaa | tgatatgaat | 1560 |
| gtgacgtatg | acgcagcaaa | tcgaattatt | acaattaaaa | gtactggtgg | aggtacaggg | 1620 |
| aattcgccgg | cacgactaat | gcctgataaa | atattggatt | tgaagtataa | gctacgtgtg | 1680 |
| aacaatgtgc | caacaccaag | aacagtaaca | tttaacgata | cattaacgta | taaaacatat | 1740 |
| tcacaagatt | ttattaattc | acctgctgaa | agtcatactg | taagtacaaa | tccatataca | 1800 |
| attgatatca | tcatgaataa | agacgcattg | caagccgaag | tcgatagacg | aattcaacaa | 1860 |
| gcggattata | catttgcatc | attagatatt | tttaatgatc | ttaaaagacg | cgcacaaaca | 1920 |
| attttagatg | aaaaccgtaa | caatgtacct | ttaaacaaaa | gagtttctca | agcagatatc | 1980 |
| gattcattag | caaatcagat | gcaacatacg | ttaattcgca | gtgttgacgc | tgaaaatgcc | 2040 |

-continued

| | |
|---|---|
| gttaatagaa aagttgatga catggaagat ttagttaacc aaaatgatga actgacagat | 2100 |
| gaagaaaaac aagcagcgat tcaagtcatc gaggaacata aaaatgaaat tattgggaat | 2160 |
| attggtgacc aaacgactga tgatggcgtt actagaatta aagatcaagg tatacagact | 2220 |
| ttaagtggag acactgcaac accagttgtt aaaccaaatg ctaaacaagc tatacgtgat | 2280 |
| aaagcagcga acaaagaga aattatcaat cacacgccag atgctactca agatgaaatt | 2340 |
| caagatgcat taaatcaatt aacaacggat gaaacagatg ctattgataa tgttacgaat | 2400 |
| gctactacca atgctgatgt tgaaacagct aaaaataatg gtattaatac aattggtgca | 2460 |
| gttgcgccac aagtgacaca caaacaagct gcaagagatg caattaatca agcgacagca | 2520 |
| acgaaacgac aacaaataaa tagcaataga gaagcaacac aagaagagaa aaatgcagca | 2580 |
| ttgaatgaat taacgcaagc cacgaaccac gcattagaac aaatcaatca agcgacaacc | 2640 |
| aatgatgatg tagatactgc caaaggtgat ggtctgaatg ccattaatcc tattgcgcct | 2700 |
| gtaactgttg tcaagcaagc agcaagagat gccgtatcac atgatgcaca acagcatatc | 2760 |
| gcagagatca atgcaaatcc tgatgcgact caagaagaaa gacaagcagc aatagagaaa | 2820 |
| gtaaatgctg ctgtagctgt tgcgaatact aatatattaa atgctaatac caatgctgat | 2880 |
| gttgagcaag taaagacaaa tgcaattcaa ggtatacaag ccattgaacc agctacaaag | 2940 |
| gttaaaacag atgctaaaaa cgctattgat caaagtgcgg aaacgcaaca taatgcgata | 3000 |
| tttaataata atgatgcgac cttagaagag caacaagcag cacaacaatt gcttgatcaa | 3060 |
| gctgtagcca cagcgaagca aaatattaat gcagcagata cgaatcaaga gttgcacaa | 3120 |
| gcaaagatc agggcacaca aaatatagtt gtgattcaac cggcaacaca agttaaaacg | 3180 |
| gatgcacgca atgctgtaaa tgaaaaagcg cgagaggcga taacaaatat caatgctaca | 3240 |
| cctggcgcga ctcgagaaga gaaacaagaa gcgataaatc gtgtcaatac acttaaaaat | 3300 |
| agagcattaa atgatattgg tgtgacgtct actactgcga tggtcaatag tattagagac | 3360 |
| gatgcagtca atcaaatcgg tgcagttcaa ccgcatgtaa cgaagaaaca aactgctaca | 3420 |
| ggtgtattaa cggacttagc aactgcaaaa aaacaagaaa ttaatcaaaa tacaaatgca | 3480 |
| accactgaag aaaagcaagt agcattaaat caagtagacc aagatttagc aacggcaatt | 3540 |
| aataatataa atcaagctga tactaatgca gaagtagatc aagcacaaca attaggtaca | 3600 |
| aaagcaatta atgcgattca gccaaatatt gtaaaaaaac ctgcagcatt agcacaaacc | 3660 |
| aatcagcatt atagtgctaa attagttgaa atcaatgcta caccagatgc aacagatgat | 3720 |
| gagaaaaatg ctgcgatcaa tactttaaat caagacagac aacaagctat tgaaagtatt | 3780 |
| aaacaagcaa atacaaatgc ggaagtagac caagctgcga cagtggcaga gaataatatc | 3840 |
| gatgctgttc aagttgacgt tgtaaaaaaa caagcagcgc gagataaaat cactgctgaa | 3900 |
| gtagcgaagc gtattgaagc ggttaaacaa acacctaatg caactgacga agaaaagcag | 3960 |
| gctgcagtta atcaaatcaa tcaacttaaa gatcaagcgt ttaatcaaat taatcaaaac | 4020 |
| caaacaaatg atcaggtaga cgcaactaca aatcaagcga ttaatgctat agataatgtt | 4080 |
| gaagctgaag tagtaattaa accaaggca attgcagata ttgaaaaagc tgttaaagaa | 4140 |
| aagcaacagc aaattgataa tagtcttgat tcaacagata tgagaaaga agttgcttta | 4200 |
| caagcattag ctaaagaaaa agaaaaagca cttgcagcta ttgaccaagc tcaaacgaat | 4260 |
| agtcaggtga atcaagcggc aacaaatggt gtatcagcga ttaaaattat tcaacctgaa | 4320 |
| acaaaaatta aaccagcagc acgtgaaaaa atcaatcaaa aagcgaatga attacgtgcg | 4380 |
| caaattaatc aagataaaga agcgacagca gaagaaagac aagcggcgtt agataaaatc | 4440 |

-continued

```
aatgatttag ttgctaaagc tatgacaaat atcacgaatg atagaacaaa tcagcaagtt    4500
aatgactcaa caaatcaagc gcttgacgac attgcattag tgacgcctga ccatattgtt    4560
agagcagctg ctagagatgc agttaagcaa caatatgaag ctaaaaagca cgaaattgag    4620
caagcggaac atgcgactga tgaagaaaaa caagttgctt taaatcaatt agcgaataat    4680
gaaaaacgtg cattacaaaa cattaatcaa gcaatagcga ataatgatgt gaaacgtgtt    4740
gaatcaaatg gtattgctac gttaaaaggc gtagaaccgc acattgtggt taaacctgaa    4800
gctcaagaag ccataaaagc gagcgcagat aaccaagtag aatctataaa agatacacca    4860
catgctacga cagatgaatt agatgaagca aaccaacaaa taaacgacac acttaaacaa    4920
ggtcaacaag atatagacaa tacgacacaa gatgcagctg tcaatgatgt tagaaaccaa    4980
acgattaagg caatcgaaca aattaaaccg aaagttagac gcaaacgtgc agcgttggat    5040
aacattgatg aaagtaataa taatcaactc gatgcaatac gaaatacgct agatacaacg    5100
caagatgaac gaaatgttgc tattgctgcg ttaaataaaa ttgttaatgc aattaaaaat    5160
gatattgcac aaaacaaaac gaatgcagaa gtggatcaaa ctgaggctga tggtaacaac    5220
aacatcaaag tgattttacc taaagttcaa gttaaaccag cagcgcgtca atctgtcagc    5280
gcaaaagctg aagctcaaaa tgcacttatt gatcaaagtg atttatctac gaagaagaa     5340 agattagctg ctaaacattt agtagaacaa gcacttaatc aagctattga tcagatcaat    5400
cacgcagata agactgcgca agttaatcaa aatagtatcg atgctcaaaa tattatttca    5460
aaaattaaac cagcgacaac agttaaagca acagcattac aacaaattca aaatatcgct    5520
acaaataaaa ttaatttaat taaagcaaat aacgaagcga cagatgaaga acaaaatgct    5580
gcaatagtac aagttgaaaa agagttaatt aaagctaaac aacaaattgc tggtgcagtg    5640
actaatgctg atgtggcata tttattgcat gatgggaaaa acgaaattcg tgaaatcgaa    5700
cctgttatta ataaaaaagc aactgcgcga gaacaattaa caacattatt caacgataag    5760
aaacaagcaa ttgaagcgaa tgttcaagca acagtagaag aaagaaatag tattttagca    5820
cagttacaaa acatttatga cactgctatt ggacaaattg atcaagatcg tagcaatgca    5880
caagttgata aaacagcaac attaaatcta caaacaatac atgatttaga cgtacatcct    5940
attaaaaagc cagatgctga aaaaacgatt aatgatgatc ttgcacgtgt tacacattta    6000
gtgcaaaatt atcgaaaagt aagtgatcgt aataaggctg atgcattaaa agctataact    6060
gcattaaaat tacaaatgga tgaagaatta aaaacagcac gcactaatgc tgatgttgat    6120
gcagttttaa aacgatttaa tgttgcatta ggcgatatag aagcagtaat tactgaaaaa    6180
gaaaatagct tactgcgcat tgataacatt gctcaacaaa catatgcgaa attcaaagcg    6240
atcgcaacac cagaacaatt agctaaagta aaagcattaa ttgatcaata tgttgcagat    6300
ggcaatagaa tggttgatga agatgcgaca ttaaatgaca tcaaaaaaga tacgcaactc    6360
attattgatg aaatttttagc aattaaatta cctgctgaag tgataaaagc gtcaccaaaa    6420
gtggggcaac ctgctccaaa agtttgtacg cctattaaaa aagaagataa acaagaagtg    6480
cgaaaagttg taaagaaact tccaaatact ggttctgaag aaatggattt accattaaaa    6540
gaattagcac taattacagg cgcagcatta ttagctagaa gacgttctaa aaaagaaaaa    6600
gaatcataa                                                            6609
```

<210> SEQ ID NO 2
<211> LENGTH: 2189
<212> TYPE: PRT

<213> ORGANISM: Staphylococcus epidermidis

<400> SEQUENCE: 2

```
Met Asn Leu Leu Lys Lys Asn Lys Tyr Ser Ile Arg Lys Tyr Lys Val
1               5                   10                  15

Gly Ile Phe Ser Thr Leu Ile Gly Thr Val Leu Leu Ser Asn Pro
                20                  25                  30

Asn Gly Ala Gln Ala Leu Thr Thr Asp His Asn Val Gln Gly Gly Ser
            35                  40                  45

Asn Gln Ala Leu Pro Gly Asn Ser Gln Asn Thr Asn Ala Asp Thr Asn
        50                  55                  60

Arg Asp Ile Val Asn Asp Ser Gln Asn Thr Pro Asn Ala His Ala Thr
65                  70                  75                  80

Asp Asn Thr Ser Thr Asn Gln Ala Leu Thr Asn His Gln Asn Val Asp
                85                  90                  95

Val Ala Asn Gln Val Gly Pro Ala Pro Ile Gln Pro Ser Ala Ser Pro
            100                 105                 110

Ala Gln Asn Asn Asn Ser Asn Ala Asn Ser Thr Ala Thr Glu Pro
        115                 120                 125

Ala Ala Asn Thr Asn Asn Asn Leu Ala Ser Asn Asn Asn Thr Leu Asn
130                 135                 140

Val Pro Asn Asn Thr Asp Asn Asp Ser Ala Arg His Leu Thr Leu
145                 150                 155                 160

Lys Glu Ile Gln Glu Asp Val Arg His Ser Ser Asp Lys Pro Glu Leu
                165                 170                 175

Val Ala Ile Ala Glu Glu Ala Ser Asn Arg Pro Lys Lys Arg Ser Arg
            180                 185                 190

Arg Ala Ala Pro Thr Asp Pro Asn Ala Thr Pro Ala Asp Pro Thr Ala
        195                 200                 205

Thr Pro Ala Asp Pro Thr Ala Gly Asn Gly Ser Ala Pro Val Ala Ile
    210                 215                 220

Thr Ala Pro Tyr Thr Pro Thr Thr Asp Pro Asn Ala Asn Asn Ile Gly
225                 230                 235                 240

Gln Asn Ala Pro Asn Glu Val Leu Ser Phe Asp Asn Asn Ile Arg
                245                 250                 255

Pro Ser Thr Asn Arg Ser Val Pro Thr Val Thr Val Asp Asn Leu
            260                 265                 270

Pro Gly Tyr Thr Leu Ile Asn Gly Gly Lys Val Gly Val Phe Ser His
        275                 280                 285

Ala Met Val Arg Thr Ser Met Phe Asp Ser Gly Asp Ala Lys Asn Tyr
290                 295                 300

Gln Ala Gln Gly Asn Val Ile Ala Leu Gly Arg Ile Arg Gly Asn Asp
305                 310                 315                 320

Thr Asn Asp His Gly Asp Phe Asn Gly Ile Glu Lys Thr Leu Thr Val
                325                 330                 335

Asn Pro Asn Ser Glu Leu Ile Phe Glu Phe Asn Thr Met Thr Thr Lys
            340                 345                 350

Asn Tyr Gln Gly Met Thr Asn Leu Ile Ile Lys Asn Ala Asp Asn Asp
        355                 360                 365

Thr Val Ile Gly Glu Lys Val Ala Tyr Gly Pro Ile Trp Arg Leu
    370                 375                 380

Leu Lys Val Pro Glu Asn Val Ser His Leu Lys Ile Gln Phe Val Pro
385                 390                 395                 400
```

-continued

```
Lys Asn Asp Ala Ile Thr Asp Ala Arg Gly Ile Tyr Gln Leu Arg Asp
                405                 410                 415

Gly Tyr Lys Tyr Tyr Asp Phe Val Asp Ser Ile Gly Leu His Ser Gly
            420                 425                 430

Ser His Val Tyr Val Glu Arg Arg Thr Met Glu Pro Thr Ala Thr Asn
        435                 440                 445

Asn Lys Glu Phe Thr Val Thr Thr Ser Leu Lys Asn Asn Gly Asn Phe
    450                 455                 460

Gly Ala Ser Phe Asn Thr Asp Asp Phe Val Tyr Lys Ile Gln Leu Pro
465                 470                 475                 480

Glu Gly Val Glu Tyr Val Asn Asn Ser Leu Thr Lys Asp Phe Pro Ser
                485                 490                 495

Gly Asn Ser Gly Val Asp Ile Asn Asp Met Asn Val Thr Tyr Asp Ala
            500                 505                 510

Ala Asn Arg Ile Ile Thr Ile Lys Ser Thr Gly Gly Gly Thr Gly Asn
        515                 520                 525

Ser Pro Ala Arg Leu Met Pro Asp Lys Ile Leu Asp Leu Lys Tyr Lys
    530                 535                 540

Leu Arg Val Asn Asn Val Pro Thr Pro Arg Thr Val Thr Phe Asn Asp
545                 550                 555                 560

Thr Leu Thr Tyr Lys Thr Tyr Ser Gln Asp Phe Ile Asn Ser Pro Ala
                565                 570                 575

Glu Ser His Thr Val Ser Thr Asn Pro Tyr Thr Ile Asp Ile Ile Met
            580                 585                 590

Asn Lys Asp Ala Leu Gln Ala Glu Val Asp Arg Arg Ile Gln Gln Ala
        595                 600                 605

Asp Tyr Thr Phe Ala Ser Leu Asp Ile Phe Asn Asp Leu Lys Arg Arg
    610                 615                 620

Ala Gln Thr Ile Leu Asp Glu Asn Arg Asn Asn Val Pro Leu Asn Lys
625                 630                 635                 640

Arg Val Ser Gln Ala Asp Ile Asp Ser Leu Ala Asn Gln Met Gln His
                645                 650                 655

Thr Leu Ile Arg Ser Val Asp Ala Glu Asn Ala Val Asn Arg Lys Val
            660                 665                 670

Asp Asp Met Glu Asp Leu Val Asn Gln Asn Asp Glu Leu Thr Asp Glu
        675                 680                 685

Glu Lys Gln Ala Ala Ile Gln Val Ile Glu Glu His Lys Asn Glu Ile
    690                 695                 700

Ile Gly Asn Ile Gly Asp Gln Thr Thr Asp Asp Gly Val Thr Arg Ile
705                 710                 715                 720

Lys Asp Gln Gly Ile Gln Thr Leu Ser Gly Asp Thr Ala Thr Pro Val
                725                 730                 735

Val Lys Pro Asn Ala Lys Gln Ala Ile Arg Asp Lys Ala Ala Lys Gln
            740                 745                 750

Arg Glu Ile Ile Asn His Thr Pro Asp Ala Thr Gln Asp Glu Ile Gln
        755                 760                 765

Asp Ala Leu Asn Gln Leu Thr Thr Asp Glu Thr Ala Ile Asp Asn
    770                 775                 780

Val Thr Asn Ala Thr Thr Asn Ala Asp Val Glu Thr Ala Lys Asn Asn
785                 790                 795                 800

Gly Ile Asn Thr Ile Gly Ala Val Ala Pro Gln Val Thr His Lys Gln
                805                 810                 815

Ala Ala Arg Asp Ala Ile Asn Gln Ala Thr Ala Thr Lys Arg Gln Gln
```

-continued

```
                820                 825                 830
Ile Asn Ser Asn Arg Glu Ala Thr Gln Glu Glu Lys Asn Ala Ala Leu
            835                 840                 845
Asn Glu Leu Thr Gln Ala Thr Asn His Ala Leu Glu Gln Ile Asn Gln
        850                 855                 860
Ala Thr Thr Asn Asp Asp Val Asp Thr Ala Lys Gly Asp Gly Leu Asn
865                 870                 875                 880
Ala Ile Asn Pro Ile Ala Pro Val Thr Val Lys Gln Ala Ala Arg
                885                 890                 895
Asp Ala Val Ser His Asp Ala Gln Gln His Ile Ala Glu Ile Asn Ala
            900                 905                 910
Asn Pro Asp Ala Thr Gln Glu Glu Arg Gln Ala Ala Ile Glu Lys Val
        915                 920                 925
Tyr Ala Ala Val Ala Val Ala Asn Thr Asn Ile Leu Asn Ala Asn Thr
    930                 935                 940
Asn Ala Asp Val Glu Gln Val Lys Thr Asn Ala Ile Gln Gly Ile Gln
945                 950                 955                 960
Ala Ile Glu Pro Ala Thr Lys Val Lys Thr Asp Ala Lys Asn Ala Ile
                965                 970                 975
Asp Gln Ser Ala Glu Thr Gln His Asn Ala Ile Phe Asn Asn Asn Asp
            980                 985                 990
Ala Thr Leu Glu Glu Gln Gln Ala  Ala Gln Gln Leu Leu  Asp Gln Ala
        995                 1000                 1005
Val Ala  Thr Ala Lys Gln Asn  Ile Asn Ala Ala Asp  Thr Asn Gln
    1010                 1015                 1020
Glu Val  Ala Gln Ala Lys Asp  Gln Gly Thr Gln Asn  Ile Val Val
    1025                 1030                 1035
Ile Gln  Pro Ala Thr Gln Val  Lys Thr Asp Ala Arg  Asn Ala Val
    1040                 1045                 1050
Asn Glu  Lys Ala Arg Glu Ala  Ile Thr Asn Ile Asn  Ala Thr Pro
    1055                 1060                 1065
Gly Ala  Thr Arg Glu Glu Lys  Gln Glu Ala Ile Asn  Arg Val Asn
    1070                 1075                 1080
Thr Leu  Lys Asn Arg Ala Leu  Asn Asp Ile Gly Val  Thr Ser Thr
    1085                 1090                 1095
Thr Ala  Met Val Asn Ser Ile  Arg Asp Asp Ala Val  Asn Gln Ile
    1100                 1105                 1110
Gly Ala  Val Gln Pro His Val  Thr Lys Lys Gln Thr  Ala Thr Gly
    1115                 1120                 1125
Val Leu  Thr Asp Leu Ala Thr  Ala Lys Lys Gln Glu  Ile Asn Gln
    1130                 1135                 1140
Asn Thr  Asn Ala Thr Thr Glu  Glu Lys Gln Val Ala  Leu Asn Gln
    1145                 1150                 1155
Val Asp  Gln Asp Leu Ala Thr  Ala Ile Asn Asn Ile  Asn Gln Ala
    1160                 1165                 1170
Asp Thr  Asn Ala Glu Val Asp  Gln Ala Gln Gln Leu  Gly Thr Lys
    1175                 1180                 1185
Ala Ile  Asn Ala Ile Gln Pro  Asn Ile Val Lys Lys  Pro Ala Ala
    1190                 1195                 1200
Leu Ala  Gln Thr Asn Gln His  Tyr Ser Ala Lys Leu  Val Glu Ile
    1205                 1210                 1215
Asn Ala  Thr Pro Asp Ala Thr  Asp Asp Glu Lys Asn  Ala Ala Ile
    1220                 1225                 1230
```

```
Asn Thr Leu Asn Gln Asp Arg Gln Gln Ala Ile Glu Ser Ile Lys
    1235                1240                1245

Gln Ala Asn Thr Asn Ala Glu Val Asp Gln Ala Ala Thr Val Ala
    1250                1255                1260

Glu Asn Asn Ile Asp Ala Val Gln Val Asp Val Val Lys Lys Gln
    1265                1270                1275

Ala Ala Arg Asp Lys Ile Thr Ala Glu Val Ala Lys Arg Ile Glu
    1280                1285                1290

Ala Val Lys Gln Thr Pro Asn Ala Thr Asp Glu Lys Gln Ala
    1295                1300                1305

Ala Val Asn Gln Ile Asn Gln Leu Lys Asp Gln Ala Phe Asn Gln
    1310                1315                1320

Ile Asn Gln Asn Gln Thr Asn Asp Gln Val Asp Ala Thr Thr Asn
    1325                1330                1335

Gln Ala Ile Asn Ala Ile Asp Asn Val Glu Ala Glu Val Val Ile
    1340                1345                1350

Lys Pro Lys Ala Ile Ala Asp Ile Glu Lys Ala Val Lys Glu Lys
    1355                1360                1365

Gln Gln Gln Ile Asp Asn Ser Leu Asp Ser Thr Asp Asn Glu Lys
    1370                1375                1380

Glu Val Ala Leu Gln Ala Leu Ala Lys Glu Lys Glu Lys Ala Leu
    1385                1390                1395

Ala Ala Ile Asp Gln Ala Gln Thr Asn Ser Gln Val Asn Gln Ala
    1400                1405                1410

Ala Thr Asn Gly Val Ser Ala Ile Lys Ile Ile Gln Pro Glu Thr
    1415                1420                1425

Lys Ile Lys Pro Ala Ala Arg Glu Lys Ile Asn Gln Lys Ala Asn
    1430                1435                1440

Glu Leu Arg Ala Gln Ile Asn Gln Asp Lys Glu Ala Thr Ala Glu
    1445                1450                1455

Glu Arg Gln Ala Ala Leu Asp Lys Ile Asn Asp Leu Val Ala Lys
    1460                1465                1470

Ala Met Thr Asn Ile Thr Asn Asp Arg Thr Asn Gln Gln Val Asn
    1475                1480                1485

Asp Ser Thr Asn Gln Ala Leu Asp Asp Ile Ala Leu Val Thr Pro
    1490                1495                1500

Asp His Ile Val Arg Ala Ala Arg Asp Ala Val Lys Gln Gln
    1505                1510                1515

Tyr Glu Ala Lys Lys His Glu Ile Glu Gln Ala Glu His Ala Thr
    1520                1525                1530

Asp Glu Glu Lys Gln Val Ala Leu Asn Gln Leu Ala Asn Asn Glu
    1535                1540                1545

Lys Arg Ala Leu Gln Asn Ile Asn Gln Ala Ile Ala Asn Asn Asp
    1550                1555                1560

Val Lys Arg Val Glu Ser Asn Gly Ile Ala Thr Leu Lys Gly Val
    1565                1570                1575

Glu Pro His Ile Val Val Lys Pro Glu Ala Gln Glu Ala Ile Lys
    1580                1585                1590

Ala Ser Ala Asp Asn Gln Val Glu Ser Ile Lys Asp Thr Pro His
    1595                1600                1605

Ala Thr Thr Asp Glu Leu Asp Glu Ala Asn Gln Gln Ile Asn Asp
    1610                1615                1620
```

-continued

```
Thr Leu Lys Gln Gly Gln Gln Asp Ile Asp Asn Thr Thr Gln Asp
1625                1630                1635
Ala Ala Val Asn Asp Val Arg Asn Gln Thr Ile Lys Ala Ile Glu
1640                1645                1650
Gln Ile Lys Pro Lys Val Arg Arg Lys Arg Ala Ala Leu Asp Asn
1655                1660                1665
Ile Asp Glu Ser Asn Asn Asn Gln Leu Asp Ala Ile Arg Asn Thr
1670                1675                1680
Leu Asp Thr Thr Gln Asp Glu Arg Asn Val Ala Ile Ala Ala Leu
1685                1690                1695
Asn Lys Ile Val Asn Ala Ile Lys Asn Asp Ile Ala Gln Asn Lys
1700                1705                1710
Thr Asn Ala Glu Val Asp Gln Thr Glu Ala Asp Gly Asn Asn Asn
1715                1720                1725
Ile Lys Val Ile Leu Pro Lys Val Gln Val Lys Pro Ala Ala Arg
1730                1735                1740
Gln Ser Val Ser Ala Lys Ala Glu Ala Gln Asn Ala Leu Ile Asp
1745                1750                1755
Gln Ser Asp Leu Ser Thr Glu Glu Glu Arg Leu Ala Ala Lys His
1760                1765                1770
Leu Val Glu Gln Ala Leu Asn Gln Ala Ile Asp Gln Ile Asn His
1775                1780                1785
Ala Asp Lys Thr Ala Gln Val Asn Gln Asn Ser Ile Asp Ala Gln
1790                1795                1800
Asn Ile Ile Ser Lys Ile Lys Pro Ala Thr Thr Val Lys Ala Thr
1805                1810                1815
Ala Leu Gln Gln Ile Gln Asn Ile Ala Thr Asn Lys Ile Asn Leu
1820                1825                1830
Ile Lys Ala Asn Asn Glu Ala Thr Asp Glu Glu Gln Asn Ala Ala
1835                1840                1845
Ile Val Gln Val Glu Lys Glu Leu Ile Lys Ala Lys Gln Gln Ile
1850                1855                1860
Ala Gly Ala Val Thr Asn Ala Asp Val Ala Tyr Leu Leu His Asp
1865                1870                1875
Gly Lys Asn Glu Ile Arg Glu Ile Glu Pro Val Ile Asn Lys Lys
1880                1885                1890
Ala Thr Ala Arg Glu Gln Leu Thr Thr Leu Phe Asn Asp Lys Lys
1895                1900                1905
Gln Ala Ile Glu Ala Asn Val Gln Ala Thr Val Glu Glu Arg Asn
1910                1915                1920
Ser Ile Leu Ala Gln Leu Gln Asn Ile Tyr Asp Thr Ala Ile Gly
1925                1930                1935
Gln Ile Asp Gln Asp Arg Ser Asn Ala Gln Val Asp Lys Thr Ala
1940                1945                1950
Thr Leu Asn Leu Gln Thr Ile His Asp Leu Asp Val His Pro Ile
1955                1960                1965
Lys Lys Pro Asp Ala Glu Lys Thr Ile Asn Asp Asp Leu Ala Arg
1970                1975                1980
Val Thr His Leu Val Gln Asn Tyr Arg Lys Val Ser Asp Arg Asn
1985                1990                1995
Lys Ala Asp Ala Leu Lys Ala Ile Thr Ala Leu Lys Leu Gln Met
2000                2005                2010
Asp Glu Glu Leu Lys Thr Ala Arg Thr Asn Ala Asp Val Asp Ala
```

-continued

```
                2015                2020                2025
Val Leu Lys Arg Phe Asn Val Ala Leu Gly Asp Ile Glu Ala Val
        2030                2035                2040

Ile Thr Glu Lys Glu Asn Ser Leu Leu Arg Ile Asp Asn Ile Ala
        2045                2050                2055

Gln Gln Thr Tyr Ala Lys Phe Lys Ala Ile Ala Thr Pro Glu Gln
        2060                2065                2070

Leu Ala Lys Val Lys Ala Leu Ile Asp Gln Tyr Val Ala Asp Gly
        2075                2080                2085

Asn Arg Met Val Asp Glu Asp Ala Thr Leu Asn Asp Ile Lys Lys
        2090                2095                2100

Asp Thr Gln Leu Ile Ile Asp Glu Ile Leu Ala Ile Lys Leu Pro
        2105                2110                2115

Ala Glu Val Ile Lys Ala Ser Pro Lys Val Gly Gln Pro Ala Pro
        2120                2125                2130

Lys Val Cys Thr Pro Ile Lys Lys Glu Asp Lys Gln Glu Val Arg
        2135                2140                2145

Lys Val Val Lys Glu Leu Pro Asn Thr Gly Ser Glu Glu Met Asp
        2150                2155                2160

Leu Pro Leu Lys Glu Leu Ala Leu Ile Thr Gly Ala Ala Leu Leu
        2165                2170                2175

Ala Arg Arg Arg Ser Lys Lys Glu Lys Glu Ser
        2180                2185
```

```
<210> SEQ ID NO 3
<211> LENGTH: 6852
<212> TYPE: DNA
<213> ORGANISM: Staphylococcus epidermidis

<400> SEQUENCE: 3
tctaatgaat gtaaagataa tacaaggagt tattacatga gtaaaagaca gaaagcattt      60
catgacagct tagcaaacga aaaaacaaga gtaagacttt ataaatctgg aaaaaattgg     120
gtaaaatccg gaattaaaga aatagaaatg ttcaaaatta tggggctacc atttattagt     180
catagtttag tgagtcaaga taatcaaagc attagtaaaa aaatgacggg atacggactg     240
aaaactacgg cggttattgg tggtgcattc acggtaaata tgttcatga ccagcaagct     300 tttgcggctt ctgatgcacc attaacttct gaattaaaca cacaaagtga acagtaggt     360 aatcaaaact caacgacaat cgaagcatca acatcaacag ccgattccac aagtgtaacg     420
aaaaatagta gttcggtaca aacatcaaat agtgacacag tctcaagtga aaagtctgaa     480
aaggtcactt cgacaactaa tagtacaagc aatcaacaag agaaattgac atctacatca     540
gaatcaacat cctcaaagaa tactacatca agttctgata ctaaatctgt agcttcaact     600
tcaagtacag aacaaccaat taatacatca acaaatcaaa gtactgcatc aaataacact     660
tcacaaagca caacgccatc ttcggtcaac ttaaacaaaa ctagcacaac gtcaactagc     720
accgcaccag taaacttcg aactttcagt cgcttagcta tgtcaacatt tgcgtcagca     780
gcgacgacaa ccgcagtaac tgctaataca attacagtta ataagataa cttaaaacaa     840 tatatgacaa cgtcaggtaa tgctacctat gatcaaagta ccggtattgt gacgttaaca     900
caggatgcat acagccaaaa aggtgctatt acattaggaa cacgtattga ctctaataag     960
agttttcatt tttctggaaa agtaaattta ggtaacaaat atgaagggca tggaaatggt    1020
ggagatggta tcggttttgc cttttcacca ggtgtattag gtgaaacagg gttaaacggt    1080
```

-continued

```
gccgcagtag gtattggtgg cttaagtaac gcatttggct tcaaattgga tacgtatcac    1140
aatacatcta aaccaaattc agctgcaaag gcgaatgctg acccatctaa tgtagctggt    1200
ggaggtgcgt ttggtgcatt tgtaacaaca gatagttatg gtgttgcgac aacgtataca    1260
tcaagttcaa cagctgataa tgctgcgaag ttaaatgttc aacctacaaa taacacgttc    1320
caagattttg atattaacta taatggtgat acaaaggtta tgactgtcaa atatgcaggt    1380
caaacatgga cacgtaatat ttcagattgg attgcgaaaa gtggtacgac caacttttca    1440
ttatcaatga cagcctcaac aggtggcgcg acaaatttac aacaagtaca atttggaaca    1500
ttcgaatata cagagtctgc tgttacacaa gtgagatacg ttgatgtaac aacaggtaaa    1560
gatattattc caccaaaaac atattcagga atgttgatc aagtcgtgac aatcgataat    1620
cagcaatctg cattgactgc taaaggatat aactacacgt ccgtcgatag ttcatatgcg    1680
tcaacttata atgatacaaa taaaactgta aaaatgacga atgctggaca atcagtgaca    1740
tattatttta ctgatgtaaa agcaccaact gtaactgtag gcaatcaaac catagaagtg    1800
ggtaaaacaa tgaatcctat tgtattgact acaacggata tggtactgg gactgtgaca    1860 aatacagtta caggattacc aagcggatta agttacgata gtgcaacgaa ttcaatcatt    1920
gggacaccaa caaaaattgg tcaatcaaca gtgacagttg tgtctactga ccaagcaaat    1980
aacaaatcga cgacaacttt tacaataaat gttgtggata cgacagcacc aacagtgaca    2040
ccaataggag atcaatcatc agaagtgtat tcaccaatat ccccgattaa aattgctacg    2100
caagataaca gtggaaatgc ggtgacgaat acagtgactg gattgccatc cggactaaca    2160
tttgatagta caaataatac tattagtggt acaccaacaa acattggtac aagtactata    2220
tcaatcgttt ctacagatgc gagcggtaac aaaacgacga caacttttaa atatgaagta    2280
acaagaaata gcatgagtga ttccgtatca acatcaggaa gtacacaaca atctcaaagt    2340
gtgtcaacaa gtaaagctga ctcacaaagt gcatcaacga gtacatcagg atcgattgtg    2400
gtatctacat cagctagtac ctcgaaatcg acaagtgtaa gcctatctga ttctgtgagt    2460
gcatctaagt cattaagcac atctgaaagt aatagtgtat caagctcaac aagcacaagt    2520
ttagtgaatt cacaaagtgt atcatcaagc atgtcggatt cagctagtaa atcaacatca    2580
ttaagcgatt ctatttcaaa ctctagcagt actgaaaaat ccgaaagtct atcaacaagt    2640
acatctgatt cattgcgtac atcaacatca ctcagtgact cattaagtat gagtacatca    2700
ggaagcttgt ctaagtcaca aagcttatca acgagtatat cagggtcgtc tagtacatca    2760
gcatcattaa gtgacagtac atcgaatgca attagtacat caacatcatt gagcgagtca    2820
gctagcaccT cggactctat cagtatttca aatagcatag ccaactctca aagtgcgtca    2880
acaagcaaat cagattcaca aagtacatca atatcattaa gtacaagtga ttcaaaatcg    2940
atgagtacat cagaatcatt gagcgattcg acgagcacaa gtggttctgt ttctggatca    3000
ctaagcatag cagcatcaca aagtgtctca acaagtacat cagactcgat gagtacttca    3060
gagatagtaa gtgactctat cagtacaagt gggtcattat ctgcatcaga cagtaaatca    3120
atgtccgtaa gtagttcaat gagcacgtct cagtcaggta gtacatcaga atcattaagt    3180
gattcacaaa gtacatctga ttctgatagt aagtcattat cacaaagtac tagtcaatca    3240
ggttcaacaa gtacatcaac gtcgacaagt gcttcagtac gtacttcgga atcacaaagt    3300
acgtctggtt caatgagtgc aagtcaatcc gattcaatga gcatatcaac gtcgtttagt    3360
gattcaacga gtgatagcaa atcagcatca actgcatcaa gtgaatcaat atcacaaagt    3420
gcttctacga gcacatctgg ttcggtaagt acttcgacat cgttaagtac aagtaattca    3480
```

```
gaacgtacat caacatctat gagtgattcc acaagcttaa gtacatcaga gtctgattca    3540
ataagtgaat caacgtcaac gagcgactct ataagtgaag caatatctgc ttcagagagc    3600
acgtttatat cattaagtga atcaaatagt actagcgatt cagaatcaca aagtgcatct    3660 gccttttttaa gtgaatcatt aagtgaaagt acgtctgaat caacatcaga gtcagtgagt    3720
agttcgacaa gtgagagtac gtcattatca gacagtacat cagaatctgg tagcacatca    3780
acatcattaa gtaattcaac aagtggtagt acgtccattt caacatcgac aagtatcagt    3840
gaatcaacgt caacgtttaa gagcgagagt gttttcaacat cactgagtat gtcaacgagt    3900
acaagtttgt ctgactctac aagtttgtca acatcattaa gtgattccac aagtgatagt    3960
aagtctgatt cattaagtac atcaatgtcg acaagtgatt caatcagtac aagtaaatct    4020
gattccatta gtacatccac atcattaagt ggttctacaa gtgaaagtga atccgactca    4080
acatcatcaa gtgaaagtaa atccgattca acatcaatga gcataagtat gtctcaatca    4140
acatcaggaa gtacaagtac gtcaacgagt acaagtttgt ctgactcaac gagtacatca    4200
ttgtcactaa gtgcctcaat gaatcaaagc ggagtagact caaactcagc aagccaaagt    4260
gcctcaaact caacaagtac aagcacgagc gaatccgatt cacaaagcac atcatcatat    4320
acaagtcagt caacaagcca aagtgaatcc acatcgacat caacgtcact aagcgattca    4380
acaagtatat ctaaaagtac gagtcaatca ggttcggtaa gcacatcagc gtcattaagt    4440
ggttcagaga gtgaatctga ttcacaaagt atctcaacaa gtgcaagtga gtcaacatca    4500
gaaagtgcgt caacatcact cagtgactca acaagtacaa gtaactcagg atcagcaagt    4560
acgtcaacat cgctcagtaa ctcagcaagc gcaagtgaat ccgatttgtc gtcaacatct    4620
ttaagtgatt caacatctgc gtcaatgcaa agcagtgaat ccgattcaca aagcacatca    4680
gcatcattaa gtgattcgct aagtacatca acttcaaacc gcatgtcgac cattgcaagt    4740
ttatctacat cggtaagtac atcagagtct ggctcaacat cagaaagtac aagtgaatcc    4800
gattcaacat caacatcatt aagcgattca caaagcacat caagaagtac aagtgcatca    4860
ggatcagcaa gtacatcaac atcaacaagt gactctcgta gtacatcagc ttcaactagt    4920
acttcgatgc gtacaagtac tagtgattca caaagtatgt cgctttcgac aagtacatca    4980
acaagtatga gtgattcaac gtcattatct gatagtgtta gtgattcaac atcagactca    5040
acaagtgcga gtacatctgg ttcgatgagt gtgtctatat cgttaagtga ttcgacaagt    5100
acatcaacat cggctagtga agtaatgagc gcaagcatat ctgattcaca agtatgtca    5160 gaatctgtaa atgattcaga aagtgtaagt gaatctaatt ctgaaagtga ctctaaatcg    5220
atgagtggct caacaagtgt cagtgattct ggctcattga gcgtctcaac gtcattaaga    5280
aaatcagaaa gtgtaagcga gtcaagttca ttgagttgct cacaatcgat gagcgattca    5340
gtaagcacaa gcgattcgtc atcattaagt gtatcgacgt cactaagaag ttcagaaagc    5400
gtgagtgaat ctgattcatt aagtgattca aaatcaacaa gtggttcgac ttcaacaagt    5460
acatctggtt cattgagtac ctcaacatca ttaagtggtt cagaaagcgt aagcgagtct    5520
acctcgctaa gtgattcaat atcaatgagt gattctacta gtacaagtga ctccgactca    5580
ttaagtggat caatatcttt aagtggttcc acaagtctta gcacttcgga ttcattaagt    5640
gattcaaaat cattgagtag ctcgcaaagt atgagtggat cagaatcaac gtcaacaagt    5700
gtgagcgatt cgcagtcaag ctcaacaagt aatagtcaat ttgactctat gagcatcagt    5760
gcatcagaaa gcgactcaat gtctacaagt gattcgtcta gcatcagtgg atcaaattca    5820
```

-continued

```
acgagtacat cactttcaac atctgactca atgagcggaa gcgtatcagt ttcaacatcg    5880
acaagtttaa gtgactcaat atcaggttca acaagtgtaa gtgactcgag ctcaacaagc    5940
acatctacat cattaagtga ttcaatgtca caaagccagt caacaagtac aagtgcatct    6000
ggttccttaa gtacatcgat atcaacatca atgtcaatga gtgctagtac atcgtcatca    6060
caaagcacat cggtgtcgac atcattatca acatcagaca gtatcagtga ttctacttca    6120
ataagtatca gtggttcaca agtacagta gaatcagaat ctacaagtga ttcaacttct     6180
atcagtgact cagaatcatt gagtacatca gattcagact cgacatcgac aagtacatcg    6240
gactcaacaa gtggttcaac ttcaacaagc atatctgaat cattaagtac gtctggttca    6300
ggttcaacga gcgtatctga ctcaacatca atgagtgaat ctaattcatc gagtgtttca    6360
atgtcacaag acaaatccga ctcaacatca attagtgact cagaatcagt gtcaacaagc    6420
acatcaacgt cattgagcac atccgattcg acaagcacat ccgaatcact gagtacatct    6480
atgtctggtt cacaaagcat ttctgactca acatcaacaa gtatgtccgg ctcaacaagt    6540
acatctgaat ctaactcaat gcatccgtca gactcaatga gtatgcatca tactcacagc    6600
acgagcacat ctcgcttatc aagtgaagca acaacgagca cgagtgaatc tcagtctaca    6660
ttaagtgcaa catctgaagt gactaaacat aatggcacac cagcacaaag tgaaaaaaga    6720
ttgccagata caggtgactc aataaaaacaa aatggattac taggtggcgt tatgacatta    6780
ttagttggtt taggtttaat gaagagaaag aaaaagaaag atgaaaatga tcaagatgat    6840
tctcaagcat aa                                                        6852
```

<210> SEQ ID NO 4
<211> LENGTH: 2283
<212> TYPE: PRT
<213> ORGANISM: Staphylococcus epidermidis

<400> SEQUENCE: 4

```
Ser Asn Glu Cys Lys Asp Asn Thr Arg Ser Tyr Tyr Met Ser Lys Arg
1               5                   10                  15

Gln Lys Ala Phe His Asp Ser Leu Ala Asn Glu Lys Thr Arg Val Arg
            20                  25                  30

Leu Tyr Lys Ser Gly Lys Asn Trp Val Lys Ser Gly Ile Lys Glu Ile
        35                  40                  45

Glu Met Phe Lys Ile Met Gly Leu Pro Phe Ile Ser His Ser Leu Val
    50                  55                  60

Ser Gln Asp Asn Gln Ser Ile Ser Lys Lys Met Thr Gly Tyr Gly Leu
65                  70                  75                  80

Lys Thr Thr Ala Val Ile Gly Gly Ala Phe Thr Val Asn Met Leu His
                85                  90                  95

Asp Gln Gln Ala Phe Ala Ala Ser Asp Ala Pro Leu Thr Ser Glu Leu
            100                 105                 110

Asn Thr Gln Ser Glu Thr Val Gly Asn Gln Asn Ser Thr Thr Ile Glu
        115                 120                 125

Ala Ser Thr Ser Thr Ala Asp Ser Thr Ser Val Thr Lys Asn Ser Ser
    130                 135                 140

Ser Val Gln Thr Ser Asn Ser Asp Thr Val Ser Ser Glu Lys Ser Glu
145                 150                 155                 160

Lys Val Thr Ser Thr Thr Asn Ser Thr Ser Asn Gln Gln Glu Lys Leu
                165                 170                 175

Thr Ser Thr Ser Glu Ser Thr Ser Ser Lys Asn Thr Thr Ser Ser Ser
            180                 185                 190
```

-continued

```
Asp Thr Lys Ser Val Ala Ser Thr Ser Ser Thr Glu Gln Pro Ile Asn
        195                 200                 205
Thr Ser Thr Asn Gln Ser Thr Ala Ser Asn Asn Thr Ser Gln Ser Thr
    210                 215                 220
Thr Pro Ser Ser Val Asn Leu Asn Lys Thr Ser Thr Thr Ser Thr Ser
225                 230                 235                 240
Thr Ala Pro Val Lys Leu Arg Thr Phe Ser Arg Leu Ala Met Ser Thr
                245                 250                 255
Phe Ala Ser Ala Ala Thr Thr Thr Ala Val Thr Ala Asn Thr Ile Thr
            260                 265                 270
Val Asn Lys Asp Asn Leu Lys Gln Tyr Met Thr Thr Ser Gly Asn Ala
        275                 280                 285
Thr Tyr Asp Gln Ser Thr Gly Ile Val Thr Leu Thr Gln Asp Ala Tyr
    290                 295                 300
Ser Gln Lys Gly Ala Ile Thr Leu Gly Thr Arg Ile Asp Ser Asn Lys
305                 310                 315                 320
Ser Phe His Phe Ser Gly Lys Val Asn Leu Gly Asn Lys Tyr Glu Gly
                325                 330                 335
His Gly Asn Gly Gly Asp Gly Ile Gly Phe Ala Phe Ser Pro Gly Val
            340                 345                 350
Leu Gly Glu Thr Gly Leu Asn Gly Ala Ala Val Gly Ile Gly Gly Leu
        355                 360                 365
Ser Asn Ala Phe Gly Phe Lys Leu Asp Thr Tyr His Asn Thr Ser Lys
    370                 375                 380
Pro Asn Ser Ala Ala Lys Ala Asn Ala Asp Pro Ser Asn Val Ala Gly
385                 390                 395                 400
Gly Gly Ala Phe Gly Ala Phe Val Thr Thr Asp Ser Tyr Gly Val Ala
                405                 410                 415
Thr Thr Tyr Thr Ser Ser Thr Ala Asp Asn Ala Ala Lys Leu Asn
            420                 425                 430
Val Gln Pro Thr Asn Asn Thr Phe Gln Asp Phe Asp Ile Asn Tyr Asn
        435                 440                 445
Gly Asp Thr Lys Val Met Thr Val Lys Tyr Ala Gly Gln Thr Trp Thr
    450                 455                 460
Arg Asn Ile Ser Asp Trp Ile Ala Lys Ser Gly Thr Thr Asn Phe Ser
465                 470                 475                 480
Leu Ser Met Thr Ala Ser Thr Gly Gly Ala Thr Asn Leu Gln Gln Val
                485                 490                 495
Gln Phe Gly Thr Phe Glu Tyr Thr Glu Ser Ala Val Thr Gln Val Arg
            500                 505                 510
Tyr Val Asp Val Thr Thr Gly Lys Asp Ile Ile Pro Lys Thr Tyr
        515                 520                 525
Ser Gly Asn Val Asp Gln Val Val Thr Ile Asp Asn Gln Gln Ser Ala
    530                 535                 540
Leu Thr Ala Lys Gly Tyr Asn Tyr Thr Ser Val Asp Ser Ser Tyr Ala
545                 550                 555                 560
Ser Thr Tyr Asn Asp Thr Asn Lys Thr Val Lys Met Thr Asn Ala Gly
                565                 570                 575
Gln Ser Val Thr Tyr Tyr Phe Thr Asp Val Lys Ala Pro Thr Val Thr
            580                 585                 590
Val Gly Asn Gln Thr Ile Glu Val Gly Lys Thr Met Asn Pro Ile Val
        595                 600                 605
```

-continued

```
Leu Thr Thr Thr Asp Asn Gly Thr Gly Thr Val Thr Asn Thr Val Thr
    610                 615                 620
Gly Leu Pro Ser Gly Leu Ser Tyr Asp Ser Ala Thr Asn Ser Ile Ile
625                 630                 635                 640
Gly Thr Pro Thr Lys Ile Gly Gln Ser Thr Val Thr Val Val Ser Thr
                645                 650                 655
Asp Gln Ala Asn Asn Lys Ser Thr Thr Thr Phe Thr Ile Asn Val Val
                660                 665                 670
Asp Thr Thr Ala Pro Thr Val Thr Pro Ile Gly Asp Gln Ser Ser Glu
            675                 680                 685
Val Tyr Ser Pro Ile Ser Pro Ile Lys Ile Ala Thr Gln Asp Asn Ser
    690                 695                 700
Gly Asn Ala Val Thr Asn Thr Val Thr Gly Leu Pro Ser Gly Leu Thr
705                 710                 715                 720
Phe Asp Ser Thr Asn Asn Thr Ile Ser Gly Thr Pro Thr Asn Ile Gly
                725                 730                 735
Thr Ser Thr Ile Ser Ile Val Ser Thr Asp Ala Ser Gly Asn Lys Thr
                740                 745                 750
Thr Thr Thr Phe Lys Tyr Glu Val Thr Arg Asn Ser Met Ser Asp Ser
            755                 760                 765
Val Ser Thr Ser Gly Ser Thr Gln Gln Ser Gln Ser Val Ser Thr Ser
    770                 775                 780
Lys Ala Asp Ser Gln Ser Ala Ser Thr Ser Thr Ser Gly Ser Ile Val
785                 790                 795                 800
Val Ser Thr Ser Ala Ser Ser Lys Ser Thr Ser Val Ser Leu Ser
                805                 810                 815
Asp Ser Val Ser Ala Ser Lys Ser Leu Ser Thr Ser Glu Ser Asn Ser
            820                 825                 830
Val Ser Ser Thr Ser Thr Ser Leu Val Asn Ser Gln Ser Val Ser
    835                 840                 845
Ser Met Ser Asp Ser Ala Ser Lys Ser Thr Ser Leu Ser Asp Ser
850                 855                 860
Ile Ser Asn Ser Ser Ser Thr Glu Lys Ser Glu Ser Leu Ser Thr Ser
865                 870                 875                 880
Thr Ser Asp Ser Leu Arg Thr Ser Thr Ser Leu Ser Asp Ser Leu Ser
                885                 890                 895
Met Ser Thr Ser Gly Ser Leu Ser Lys Ser Gln Ser Leu Ser Thr Ser
                900                 905                 910
Ile Ser Gly Ser Ser Ser Thr Ser Ala Ser Leu Ser Asp Ser Thr Ser
    915                 920                 925
Asn Ala Ile Ser Thr Ser Thr Ser Leu Ser Glu Ser Ala Ser Thr Ser
930                 935                 940
Asp Ser Ile Ser Ile Ser Asn Ser Ile Ala Asn Ser Gln Ser Ala Ser
945                 950                 955                 960
Thr Ser Lys Ser Asp Ser Gln Ser Thr Ser Ile Ser Leu Ser Thr Ser
                965                 970                 975
Asp Ser Lys Ser Met Ser Thr Ser Glu Ser Leu Ser Asp Ser Thr Ser
            980                 985                 990
Thr Ser Gly Ser Val Ser Gly Ser  Leu Ser Ile Ala Ala  Ser Gln Ser
    995                 1000                1005
Val Ser  Thr Ser Thr Ser Asp  Ser Met Ser Thr Ser  Glu Ile Val
    1010                1015                1020
Ser Asp  Ser Ile Ser Thr Ser  Gly Ser Leu Ser Ala  Ser Asp Ser
```

-continued

```
                1025                1030                1035
Lys Ser Met Ser Val Ser Ser Met Ser Thr Ser Gln Ser Gly
    1040                1045                1050
Ser Thr Ser Glu Ser Leu Ser Asp Ser Gln Ser Thr Ser Asp Ser
    1055                1060                1065
Asp Ser Lys Ser Leu Ser Gln Ser Thr Ser Gln Ser Gly Ser Thr
    1070                1075                1080
Ser Thr Ser Thr Ser Thr Ser Ala Ser Val Arg Thr Ser Glu Ser
    1085                1090                1095
Gln Ser Thr Ser Gly Ser Met Ser Ala Ser Gln Ser Asp Ser Met
    1100                1105                1110
Ser Ile Ser Thr Ser Phe Ser Asp Ser Thr Ser Asp Ser Lys Ser
    1115                1120                1125
Ala Ser Thr Ala Ser Ser Glu Ser Ile Ser Gln Ser Ala Ser Thr
    1130                1135                1140
Ser Thr Ser Gly Ser Val Ser Thr Ser Thr Ser Leu Ser Thr Ser
    1145                1150                1155
Asn Ser Glu Arg Thr Ser Thr Ser Met Ser Asp Ser Thr Ser Leu
    1160                1165                1170
Ser Thr Ser Glu Ser Asp Ser Ile Ser Glu Ser Thr Ser Thr Ser
    1175                1180                1185
Asp Ser Ile Ser Glu Ala Ile Ser Ala Ser Glu Ser Thr Phe Ile
    1190                1195                1200
Ser Leu Ser Glu Ser Asn Ser Thr Ser Asp Ser Glu Ser Gln Ser
    1205                1210                1215
Ala Ser Ala Phe Leu Ser Glu Ser Leu Ser Glu Ser Thr Ser Glu
    1220                1225                1230
Ser Thr Ser Glu Ser Val Ser Ser Ser Thr Ser Glu Ser Thr Ser
    1235                1240                1245
Leu Ser Asp Ser Thr Ser Glu Ser Gly Ser Thr Ser Thr Ser Leu
    1250                1255                1260
Ser Asn Ser Thr Ser Gly Ser Thr Ser Ile Ser Thr Ser Thr Ser
    1265                1270                1275
Ile Ser Glu Ser Thr Ser Thr Phe Lys Ser Glu Ser Val Ser Thr
    1280                1285                1290
Ser Leu Ser Met Ser Thr Ser Thr Ser Leu Ser Asp Ser Thr Ser
    1295                1300                1305
Leu Ser Thr Ser Leu Ser Asp Ser Thr Ser Asp Ser Lys Ser Asp
    1310                1315                1320
Ser Leu Ser Thr Ser Met Ser Thr Ser Asp Ser Ile Ser Thr Ser
    1325                1330                1335
Lys Ser Asp Ser Ile Ser Thr Ser Thr Ser Leu Ser Gly Ser Thr
    1340                1345                1350
Ser Glu Ser Glu Ser Asp Ser Thr Ser Ser Glu Ser Lys Ser
    1355                1360                1365
Asp Ser Thr Ser Met Ser Ile Ser Met Ser Gln Ser Thr Ser Gly
    1370                1375                1380
Ser Thr Ser Thr Ser Thr Ser Thr Ser Leu Ser Asp Ser Thr Ser
    1385                1390                1395
Thr Ser Leu Ser Leu Ser Ala Ser Met Asn Gln Ser Gly Val Asp
    1400                1405                1410
Ser Asn Ser Ala Ser Gln Ser Ala Ser Asn Ser Thr Ser Thr Ser
    1415                1420                1425
```

```
Thr Ser Glu Ser Asp Ser Gln  Ser Thr Ser Ser Tyr  Thr Ser Gln
    1430            1435                1440

Ser Thr Ser Gln Ser Glu Ser  Thr Ser Thr Ser Thr  Ser Leu Ser
    1445            1450                1455

Asp Ser Thr Ser Ile Ser Lys  Ser Thr Ser Gln Ser  Gly Ser Val
    1460            1465                1470

Ser Thr Ser Ala Ser Leu Ser  Gly Ser Glu Ser Glu  Ser Asp Ser
    1475            1480                1485

Gln Ser Ile Ser Thr Ser Ala  Ser Glu Ser Thr Ser  Glu Ser Ala
    1490            1495                1500

Ser Thr Ser Leu Ser Asp Ser  Thr Ser Thr Ser Asn  Ser Gly Ser
    1505            1510                1515

Ala Ser Thr Ser Thr Ser Leu  Ser Asn Ser Ala Ser  Ala Ser Glu
    1520            1525                1530

Ser Asp Leu Ser Ser Thr Ser  Leu Ser Asp Ser Thr  Ser Ala Ser
    1535            1540                1545

Met Gln Ser Ser Glu Ser Asp  Ser Gln Ser Thr Ser  Ala Ser Leu
    1550            1555                1560

Ser Asp Ser Leu Ser Thr Ser  Thr Ser Asn Arg Met  Ser Thr Ile
    1565            1570                1575

Ala Ser Leu Ser Thr Ser Val  Ser Thr Ser Glu Ser  Gly Ser Thr
    1580            1585                1590

Ser Glu Ser Thr Ser Glu Ser  Asp Ser Thr Ser Thr  Ser Leu Ser
    1595            1600                1605

Asp Ser Gln Ser Thr Ser Arg  Ser Thr Ser Ala Ser  Gly Ser Ala
    1610            1615                1620

Ser Thr Ser Thr Ser Thr Ser  Asp Ser Arg Ser Thr  Ser Ala Ser
    1625            1630                1635

Thr Ser Thr Ser Met Arg Thr  Ser Thr Ser Asp Ser  Gln Ser Met
    1640            1645                1650

Ser Leu Ser Thr Ser Thr Ser  Thr Ser Met Ser Asp  Ser Thr Ser
    1655            1660                1665

Leu Ser Asp Ser Val Ser Asp  Ser Thr Ser Asp Ser  Thr Ser Ala
    1670            1675                1680

Ser Thr Ser Gly Ser Met Ser  Val Ser Ile Ser Leu  Ser Asp Ser
    1685            1690                1695

Thr Ser Thr Ser Thr Ser Ala  Ser Glu Val Met Ser  Ala Ser Ile
    1700            1705                1710

Ser Asp Ser Gln Ser Met Ser  Glu Ser Val Asn Asp  Ser Glu Ser
    1715            1720                1725

Val Ser Glu Ser Asn Ser Glu  Ser Asp Ser Lys Ser  Met Ser Gly
    1730            1735                1740

Ser Thr Ser Val Ser Asp Ser  Gly Ser Leu Ser Val  Ser Thr Ser
    1745            1750                1755

Leu Arg Lys Ser Glu Ser Val  Ser Glu Ser Ser Ser  Leu Ser Cys
    1760            1765                1770

Ser Gln Ser Met Ser Asp Ser  Val Ser Thr Ser Asp  Ser Ser Ser
    1775            1780                1785

Leu Ser Val Ser Thr Ser Leu  Arg Ser Ser Glu Ser  Val Ser Glu
    1790            1795                1800

Ser Asp Ser Leu Ser Asp Ser  Lys Ser Thr Ser Gly  Ser Thr Ser
    1805            1810                1815
```

-continued

```
Thr Ser Thr Ser Gly Ser Leu Ser Thr Ser Leu Ser Gly
    1820            1825            1830

Ser Glu Ser Val Ser Glu Ser Thr Ser Leu Ser Asp Ser Ile Ser
    1835            1840            1845

Met Ser Asp Ser Thr Ser Thr Ser Asp Ser Asp Ser Leu Ser Gly
    1850            1855            1860

Ser Ile Ser Leu Ser Gly Ser Thr Ser Leu Ser Thr Ser Asp Ser
    1865            1870            1875

Leu Ser Asp Ser Lys Ser Leu Ser Ser Ser Gln Ser Met Ser Gly
    1880            1885            1890

Ser Glu Ser Thr Ser Thr Ser Val Ser Asp Ser Gln Ser Ser Ser
    1895            1900            1905

Thr Ser Asn Ser Gln Phe Asp Ser Met Ser Ile Ser Ala Ser Glu
    1910            1915            1920

Ser Asp Ser Met Ser Thr Ser Asp Ser Ser Ser Ile Ser Gly Ser
    1925            1930            1935

Asn Ser Thr Ser Thr Ser Leu Ser Thr Ser Asp Ser Met Ser Gly
    1940            1945            1950

Ser Val Ser Val Ser Thr Ser Thr Ser Leu Ser Asp Ser Ile Ser
    1955            1960            1965

Gly Ser Thr Ser Val Ser Asp Ser Ser Ser Thr Ser Thr Ser Thr
    1970            1975            1980

Ser Leu Ser Asp Ser Met Ser Gln Ser Gln Ser Thr Ser Thr Ser
    1985            1990            1995

Ala Ser Gly Ser Leu Ser Thr Ser Ile Ser Thr Ser Met Ser Met
    2000            2005            2010

Ser Ala Ser Thr Ser Ser Ser Gln Ser Thr Ser Val Ser Thr Ser
    2015            2020            2025

Leu Ser Thr Ser Asp Ser Ile Ser Asp Ser Thr Ser Ile Ser Ile
    2030            2035            2040

Ser Gly Ser Gln Ser Thr Val Glu Ser Glu Ser Thr Ser Asp Ser
    2045            2050            2055

Thr Ser Ile Ser Asp Ser Glu Ser Leu Ser Thr Ser Asp Ser Asp
    2060            2065            2070

Ser Thr Ser Thr Ser Thr Ser Asp Ser Thr Ser Gly Ser Thr Ser
    2075            2080            2085

Thr Ser Ile Ser Glu Ser Leu Ser Thr Ser Gly Ser Gly Ser Thr
    2090            2095            2100

Ser Val Ser Asp Ser Thr Ser Met Ser Glu Ser Asn Ser Ser Ser
    2105            2110            2115

Val Ser Met Ser Gln Asp Lys Ser Asp Ser Thr Ser Ile Ser Asp
    2120            2125            2130

Ser Glu Ser Val Ser Thr Ser Thr Ser Thr Ser Leu Ser Thr Ser
    2135            2140            2145

Asp Ser Thr Ser Thr Ser Glu Ser Leu Ser Thr Ser Met Ser Gly
    2150            2155            2160

Ser Gln Ser Ile Ser Asp Ser Thr Ser Thr Ser Met Ser Gly Ser
    2165            2170            2175

Thr Ser Thr Ser Glu Ser Asn Ser Met His Pro Ser Asp Ser Met
    2180            2185            2190

Ser Met His His Thr His Ser Thr Ser Thr Ser Arg Leu Ser Ser
    2195            2200            2205

Glu Ala Thr Thr Ser Thr Ser Glu Ser Gln Ser Thr Leu Ser Ala
```

-continued

```
            2210                  2215                  2220
Thr Ser Glu Val Thr Lys His Asn Gly Thr Pro Ala Gln Ser Glu
    2225                  2230                  2235

Lys Arg Leu Pro Asp Thr Gly Asp Ser Ile Lys Gln Asn Gly Leu
    2240                  2245                  2250

Leu Gly Gly Val Met Thr Leu Leu Val Gly Leu Gly Leu Met Lys
    2255                  2260                  2265

Arg Lys Lys Lys Lys Asp Glu Asn Asp Gln Asp Asp Ser Gln Ala
    2270                  2275                  2280
```

<210> SEQ ID NO 5
<211> LENGTH: 2730
<212> TYPE: DNA
<213> ORGANISM: Staphylococcus epidermidis

<400> SEQUENCE: 5

| | | | | | |
|---|---|---|---|---|---|
| ttattatcaa | ttaaatataa | tcttatagga | gttgttaaca | acatgaacaa | acatcaccca | 60 |
| aaattaaggt | ctttctattc | tattagaaaa | tcaactctag | gcgttgcatc | ggtcattgtc | 120 |
| agtacactat | ttttaattac | ttctcaacat | caagcacaag | cagcagaaaa | tacaaatact | 180 |
| tcagataaaa | tctcggaaaa | tcaaaataat | aatgcaacta | caactcagcc | acctaaggat | 240 |
| acaaatcaaa | cacaacctgc | tacgcaacca | gcaaacactg | cgaaaaacta | tcctgcagcg | 300 |
| gatgaatcac | ttaaagatgc | aattaaagat | cctgcattag | aaaataaaga | acatgatata | 360 |
| ggtccaagag | aacaagtcaa | tttccagtta | ttagataaaa | acaatgaaac | gcagtactat | 420 |
| cacttttca | gcatcaaaga | tccagcagat | gtgtattaca | ctaaaaagaa | agcagaagtt | 480 |
| gaattagaca | tcaatactgc | ttcaacatgg | aagaagtttg | aagtctatga | aaacaatcaa | 540 |
| aaattgccag | tgagacttgt | atcatatagt | cctgtaccag | aagaccatgc | ctatattcga | 600 |
| ttcccagttt | cagatggcac | acaagaattg | aaaattgttt | cttcgactca | aattgatgat | 660 |
| ggagaagaaa | caaattatga | ttatactaaa | ttagtatttg | ctaaacctat | ttataacgat | 720 |
| ccttcacttg | taaaatcaga | tacaaatgat | gcagtagtaa | cgaatgatca | atcaagttca | 780 |
| gtcgcaagta | atcaaacaaa | cacgaataca | tctaatcaaa | atatatcaac | gatcaacaat | 840 |
| gctaataatc | aaccgcaggc | aacgaccaat | atgagtcaac | ctgcacaacc | aaaatcgtca | 900 |
| acgaatgcag | atcaagcgtc | aagccaacca | gctcatgaaa | caaattctaa | tggtaatact | 960 |
| aacgataaaa | cgaatgagtc | aagtaatcag | tcggatgtta | tcaacagta | tccaccagca | 1020 |
| gatgaatcac | tacaagatgc | aattaaaaac | ccggctatca | tcgataaaga | acatacagct | 1080 |
| gataattggc | gaccaattga | ttttcaaatg | aaaaatgata | aggtgaaag | acagttctat | 1140 |
| cattatgcta | gtactgttga | accagcaact | gtcatttta | caaaacagg | accaataatt | 1200 |
| gaattaggtt | taaagacagc | ttcaacatgg | aagaaatttg | aagtttatga | aggtgacaaa | 1260 |
| aagttaccag | tcgaattagt | atcatatgat | tctgataaag | attatgccta | tattcgtttc | 1320 |
| ccagtatcta | atggtacgag | agaagttaaa | attgtgtcat | ctattgaata | tggtgagaac | 1380 |
| atccatgaag | actatgatta | tacgctaatg | gtctttgcac | agcctattac | taataaccca | 1440 |
| gacgactatg | tggatgaaga | aacatacaat | ttacaaaaat | tattagctcc | gtatcacaaa | 1500 |
| gctaaaacgt | tagaaagaca | agtttatgaa | ttagaaaaat | tacaagagaa | attgccagaa | 1560 |
| aaatataagg | cggaatataa | aaagaaatta | gatcaaacta | gagtagagtt | agctgatcaa | 1620 |
| gttaaatcag | cagtgacgga | atttgaaaat | gttacaccta | caaatgatca | attaacagat | 1680 |
| ttacaagaag | cgcattttgt | tgttttttgaa | agtgaagaaa | atagtgagtc | agttatggac | 1740 |

```
ggctttgttg aacatccatt ctatacagca actttaaatg gtcaaaaata tgtagtgatg    1800
aaaacaaagg atgacagtta ctggaaagat ttaattgtag aaggtaaacg tgtcactact    1860
gtttctaaag atcctaaaaa taattctaga acgctgattt tcccatatat acctgacaaa    1920
gcagtttaca atgcgattgt taaagtcgtt gtggcaaaca ttggttatga aggtcaatat    1980
catgtcagaa ttataaatca ggatatcaat acaaaagatg atgatacatc acaaaataac    2040
acgagtgaac cgctaaatgt acaaacagga caagaaggta aggttgctga tacagatgta    2100
gctgaaaata gcagcactgc aacaaatcct aaagatgcgt ctgataaagc agatgtgata    2160
gaaccagagt ctgacgtggt taaagatgct gataataata ttgataaaga tgtgcaacat    2220
gatgttgatc atttatccga tatgtcggat aataatcact tcgataaata tgatttaaaa    2280
gaaatggata ctcaaattgc caaagatact gatagaaatg tggataaaga tgccgataat    2340
agcgttggta tgtcatctaa tgtcgatact gataaagact ctaataaaaa taaagacaaa    2400
gtcatacagc tgaatcatat tgccgataaa aataatcata ctggaaaagc agcaaagctt    2460
gacgtagtga aacaaaatta taataataca gacaaagtta ctgacaaaaa aacaactgaa    2520
catctgccga gtgatattca taaaactgta gataaaacag tgaaaacaaa agaaaaagcc    2580
ggcacaccat cgaaagaaaa caaacttagt caatctaaaa tgctaccaaa aactggagaa    2640
acaacttcaa gccaatcatg gtggggctta tatgcgttat taggtatgtt agctttattc    2700
attcctaaat tcagaaaaga atctaaataa                                     2730
```

<210> SEQ ID NO 6
<211> LENGTH: 909
<212> TYPE: PRT
<213> ORGANISM: Staphylococcus epidermidis

<400> SEQUENCE: 6

```
Leu Leu Ser Ile Lys Tyr Asn Leu Ile Gly Val Val Asn Asn Met Asn
 1               5                  10                  15

Lys His His Pro Lys Leu Arg Ser Phe Tyr Ser Ile Arg Lys Ser Thr
            20                  25                  30

Leu Gly Val Ala Ser Val Ile Val Ser Thr Leu Phe Leu Ile Thr Ser
        35                  40                  45

Gln His Gln Ala Gln Ala Ala Glu Asn Thr Asn Thr Ser Asp Lys Ile
    50                  55                  60

Ser Glu Asn Gln Asn Asn Asn Ala Thr Thr Thr Gln Pro Pro Lys Asp
65                  70                  75                  80

Thr Asn Gln Thr Gln Pro Ala Thr Gln Pro Ala Asn Thr Ala Lys Asn
                85                  90                  95

Tyr Pro Ala Ala Asp Glu Ser Leu Lys Asp Ala Ile Lys Asp Pro Ala
           100                 105                 110

Leu Glu Asn Lys Glu His Asp Ile Gly Pro Arg Glu Gln Val Asn Phe
       115                 120                 125

Gln Leu Leu Asp Lys Asn Asn Glu Thr Gln Tyr Tyr His Phe Phe Ser
   130                 135                 140

Ile Lys Asp Pro Ala Asp Val Tyr Tyr Thr Lys Lys Ala Glu Val
145                 150                 155                 160

Glu Leu Asp Ile Asn Thr Ala Ser Thr Trp Lys Lys Phe Glu Val Tyr
               165                 170                 175

Glu Asn Asn Gln Lys Leu Pro Val Arg Leu Val Ser Tyr Ser Pro Val
           180                 185                 190
```

-continued

```
Pro Glu Asp His Ala Tyr Ile Arg Phe Pro Val Ser Asp Gly Thr Gln
        195                 200                 205
Glu Leu Lys Ile Val Ser Ser Thr Gln Ile Asp Asp Gly Glu Glu Thr
    210                 215                 220
Asn Tyr Asp Tyr Thr Lys Leu Val Phe Ala Lys Pro Ile Tyr Asn Asp
225                 230                 235                 240
Pro Ser Leu Val Lys Ser Asp Thr Asn Asp Ala Val Val Thr Asn Asp
                245                 250                 255
Gln Ser Ser Ser Val Ala Ser Asn Gln Thr Asn Thr Asn Thr Ser Asn
            260                 265                 270
Gln Asn Ile Ser Thr Ile Asn Asn Ala Asn Asn Gln Pro Gln Ala Thr
        275                 280                 285
Thr Asn Met Ser Gln Pro Ala Gln Pro Lys Ser Ser Thr Asn Ala Asp
    290                 295                 300
Gln Ala Ser Ser Gln Pro Ala His Glu Thr Asn Ser Asn Gly Asn Thr
305                 310                 315                 320
Asn Asp Lys Thr Asn Glu Ser Ser Asn Gln Ser Asp Val Asn Gln Gln
                325                 330                 335
Tyr Pro Pro Ala Asp Glu Ser Leu Gln Asp Ala Ile Lys Asn Pro Ala
            340                 345                 350
Ile Ile Asp Lys Glu His Thr Ala Asp Asn Trp Arg Pro Ile Asp Phe
        355                 360                 365
Gln Met Lys Asn Asp Lys Gly Glu Arg Gln Phe Tyr His Tyr Ala Ser
    370                 375                 380
Thr Val Glu Pro Ala Thr Val Ile Phe Thr Lys Thr Gly Pro Ile Ile
385                 390                 395                 400
Glu Leu Gly Leu Lys Thr Ala Ser Thr Trp Lys Lys Phe Glu Val Tyr
                405                 410                 415
Glu Gly Asp Lys Lys Leu Pro Val Glu Leu Val Ser Tyr Asp Ser Asp
            420                 425                 430
Lys Asp Tyr Ala Tyr Ile Arg Phe Pro Val Ser Asn Gly Thr Arg Glu
        435                 440                 445
Val Lys Ile Val Ser Ser Ile Glu Tyr Gly Glu Asn Ile His Glu Asp
    450                 455                 460
Tyr Asp Tyr Thr Leu Met Val Phe Ala Gln Pro Ile Thr Asn Asn Pro
465                 470                 475                 480
Asp Asp Tyr Val Asp Glu Glu Thr Tyr Asn Leu Gln Lys Leu Leu Ala
                485                 490                 495
Pro Tyr His Lys Ala Lys Thr Leu Glu Arg Gln Val Tyr Glu Leu Glu
            500                 505                 510
Lys Leu Gln Glu Lys Leu Pro Glu Lys Tyr Lys Ala Glu Tyr Lys Lys
        515                 520                 525
Lys Leu Asp Gln Thr Arg Val Glu Leu Ala Asp Gln Val Lys Ser Ala
    530                 535                 540
Val Thr Glu Phe Glu Asn Val Thr Pro Thr Asn Asp Gln Leu Thr Asp
545                 550                 555                 560
Leu Gln Glu Ala His Phe Val Val Phe Glu Ser Glu Asn Ser Glu
                565                 570                 575
Ser Val Met Asp Gly Phe Val Glu His Pro Phe Tyr Thr Ala Thr Leu
            580                 585                 590
Asn Gly Gln Lys Tyr Val Val Met Lys Thr Lys Asp Asp Ser Tyr Trp
        595                 600                 605
Lys Asp Leu Ile Val Glu Gly Lys Arg Val Thr Thr Val Ser Lys Asp
```

```
            610                 615                 620
Pro Lys Asn Asn Ser Arg Thr Leu Ile Phe Pro Tyr Ile Pro Asp Lys
625                 630                 635                 640

Ala Val Tyr Asn Ala Ile Val Lys Val Val Ala Asn Ile Gly Tyr
                645                 650                 655

Glu Gly Gln Tyr His Val Arg Ile Ile Asn Gln Asp Ile Asn Thr Lys
                660                 665                 670

Asp Asp Asp Thr Ser Gln Asn Asn Thr Ser Glu Pro Leu Asn Val Gln
                675                 680                 685

Thr Gly Gln Glu Gly Lys Val Ala Asp Thr Asp Val Ala Glu Asn Ser
690                 695                 700

Ser Thr Ala Thr Asn Pro Lys Asp Ala Ser Asp Lys Ala Asp Val Ile
705                 710                 715                 720

Glu Pro Glu Ser Asp Val Val Lys Asp Ala Asp Asn Ile Asp Lys
                725                 730                 735

Asp Val Gln His Asp Val Asp His Leu Ser Asp Met Ser Asp Asn Asn
                740                 745                 750

His Phe Asp Lys Tyr Asp Leu Lys Glu Met Asp Thr Gln Ile Ala Lys
                755                 760                 765

Asp Thr Asp Arg Asn Val Asp Lys Asp Ala Asp Asn Ser Val Gly Met
770                 775                 780

Ser Ser Asn Val Asp Thr Asp Lys Asp Ser Asn Lys Asn Lys Asp Lys
785                 790                 795                 800

Val Ile Gln Leu Asn His Ile Ala Asp Lys Asn His Thr Gly Lys
                805                 810                 815

Ala Ala Lys Leu Asp Val Val Lys Gln Asn Tyr Asn Asn Thr Asp Lys
                820                 825                 830

Val Thr Asp Lys Lys Thr Thr Glu His Leu Pro Ser Asp Ile His Lys
835                 840                 845

Thr Val Asp Lys Thr Val Lys Thr Lys Glu Lys Ala Gly Thr Pro Ser
850                 855                 860

Lys Glu Asn Lys Leu Ser Gln Ser Lys Met Leu Pro Lys Thr Gly Glu
865                 870                 875                 880

Thr Thr Ser Ser Gln Ser Trp Trp Gly Leu Tyr Ala Leu Leu Gly Met
                885                 890                 895

Leu Ala Leu Phe Ile Pro Lys Phe Arg Lys Glu Ser Lys
                900                 905

<210> SEQ ID NO 7
<211> LENGTH: 1065
<212> TYPE: DNA
<213> ORGANISM: Staphylococcus epidermidis

<400> SEQUENCE: 7
gaggaaaaca acatgacaaa acattattta aacagtaagt atcaatcaga acaacgttca      60
tcagctatga aaagattac aatgggtaca gcatctatca ttttaggttc ccttgtatac      120
ataggcgcag acagccaaca agtcaatgcg gcaacagaag ctacgaacgc aactaataat      180
caaagcacac aagtttctca agcaacatca caaccaatta atttccaagt gcaaaaagat      240
ggctcttcag agaagtcaca catggatgac tatatgcaac accctggtaa agtaattaaa      300
caaaataata atattatttt ccaaaccgtg ttaaacaatg catcattctg gaagaatac       360 aaattttaca atgcaaacaa tcaagaatta gcaacaactg ttgttaacga ataataaaaaa     420 gcggatacta gaacaatcaa tgttgcagtt gaacctggat ataagagctt aactactaaa     480
```

-continued

```
gtacatattg tcgtgccaca aattaattac aatcatagat atactacgca tttggaattt      540
gaaaaagcaa ttcctacatt agctgacgca gcaaaaccaa acaatgttaa accggttcaa      600
ccaaaaccag ctcaacctaa aacacctact gagcaaacta aaccagttca acctaaagtt      660
gaaaaagtta aacctactgt aactacaaca agcaaagttg aagacaatca ctctactaaa      720
gttgtaagta ctgacacaac aaaagatcaa actaaaacac aaactgctca tacagttaaa      780
acagcacaaa ctgctcaaga acaaaataaa gttcaaacac ctgttaaaga tgttgcaaca      840
gcgaaatctg aaagcaacaa tcaagctgta agtgataata aatcacaaca aactaacaaa      900
gttacaaaac ataacgaaac gcctaaacaa gcatctaaag ctaaagaatt accaaaaact      960
ggtttaactt cagttgataa cttttattagc acagttgcct tcgcaacact tgcccttta     1020 ggttcattat ctttattact tttcaaaaga aaagaatcta aataa                     1065
```

<210> SEQ ID NO 8
<211> LENGTH: 354
<212> TYPE: PRT
<213> ORGANISM: Staphylococcus epidermidis

<400> SEQUENCE: 8

```
Glu Glu Asn Asn Met Thr Lys His Tyr Leu Asn Ser Lys Tyr Gln Ser
1               5                   10                  15

Glu Gln Arg Ser Ser Ala Met Lys Lys Ile Thr Met Gly Thr Ala Ser
            20                  25                  30

Ile Ile Leu Gly Ser Leu Val Tyr Ile Gly Ala Asp Ser Gln Gln Val
        35                  40                  45

Asn Ala Ala Thr Glu Ala Thr Asn Ala Thr Asn Asn Gln Ser Thr Gln
    50                  55                  60

Val Ser Gln Ala Thr Ser Gln Pro Ile Asn Phe Gln Val Gln Lys Asp
65                  70                  75                  80

Gly Ser Ser Glu Lys Ser His Met Asp Asp Tyr Met Gln His Pro Gly
                85                  90                  95

Lys Val Ile Lys Gln Asn Asn Lys Tyr Tyr Phe Gln Thr Val Leu Asn
            100                 105                 110

Asn Ala Ser Phe Trp Lys Glu Tyr Lys Phe Tyr Asn Ala Asn Asn Gln
        115                 120                 125

Glu Leu Ala Thr Thr Val Val Asn Asp Asn Lys Lys Ala Asp Thr Arg
    130                 135                 140

Thr Ile Asn Val Ala Val Glu Pro Gly Tyr Lys Ser Leu Thr Thr Lys
145                 150                 155                 160

Val His Ile Val Val Pro Gln Ile Asn Tyr Asn His Arg Tyr Thr Thr
                165                 170                 175

His Leu Glu Phe Glu Lys Ala Ile Pro Thr Leu Ala Asp Ala Ala Lys
            180                 185                 190

Pro Asn Asn Val Lys Pro Val Gln Pro Lys Pro Ala Gln Pro Lys Thr
        195                 200                 205

Pro Thr Glu Gln Thr Lys Pro Val Gln Pro Lys Val Glu Lys Val Lys
    210                 215                 220

Pro Thr Val Thr Thr Thr Ser Lys Val Glu Asp Asn His Ser Thr Lys
225                 230                 235                 240

Val Val Ser Thr Asp Thr Thr Lys Asp Gln Thr Lys Thr Gln Thr Ala
                245                 250                 255

His Thr Val Lys Thr Ala Gln Thr Ala Gln Glu Gln Asn Lys Val Gln
            260                 265                 270
```

```
Thr Pro Val Lys Asp Val Ala Thr Ala Lys Ser Glu Ser Asn Asn Gln
            275                 280                 285

Ala Val Ser Asp Asn Lys Ser Gln Gln Thr Asn Lys Val Thr Lys His
        290                 295                 300

Asn Glu Thr Pro Lys Gln Ala Ser Lys Ala Lys Glu Leu Pro Lys Thr
305                 310                 315                 320

Gly Leu Thr Ser Val Asp Asn Phe Ile Ser Thr Val Ala Phe Ala Thr
                325                 330                 335

Leu Ala Leu Leu Gly Ser Leu Ser Leu Leu Leu Phe Lys Arg Lys Glu
            340                 345                 350

Ser Lys

<210> SEQ ID NO 9
<211> LENGTH: 1965
<212> TYPE: DNA
<213> ORGANISM: Staphylococcus epidermidis

<400> SEQUENCE: 9
```

| | | | | | |
|---|---|---|---|---|---|
| tatacaatta | ggagttgttt | ctacaacatg | aacaaacagc | aaaaagaatt | taaatcattt | 60 |
| tattcaatta | gaaagtcatc | actaggcgtt | gcatctgtag | caattagtac | acttttatta | 120 |
| ttaatgtcaa | atggcgaagc | acaagcagca | gctgaagaaa | caggtggtac | aaatacagaa | 180 |
| gcacaaccaa | aaactgaagc | agttgcaagt | ccaacaacaa | catctgaaaa | agctccagaa | 240 |
| actaaaccag | tagctaatgc | tgtctcagta | tctaataaag | aagttgaggc | ccctacttct | 300 |
| gaaacaaaag | aagctaaaga | agttaaagaa | gttaaagccc | taaggaaac | aaaagaagtt | 360 |
| aaaccagcag | caaaagccac | taacaataca | tatcctatt | tgaatcagga | acttagagaa | 420 |
| gcgattaaaa | accctgcaat | aaaagacaaa | gatcatagcg | caccaaactc | tcgtccaatt | 480 |
| gattttgaaa | tgaaaagaa | agatggaact | caacagtttt | atcattatgc | aagttctgtt | 540 |
| aaacctgcta | gagttatttt | cactgattca | aaaccagaaa | ttgaattagg | attacaatca | 600 |
| ggtcaatttt | ggagaaaatt | tgaagtttat | gaaggtgaca | aaaagttgcc | aattaaatta | 660 |
| gtatcatacg | atactgttaa | agattatgct | tacattcgct | tctctgtatc | aaacggaaca | 720 |
| aaagctgtta | aaattgttag | ttcaacacac | ttcaataaca | aagaagaaaa | atacgattac | 780 |
| acattaatgg | aattcgcaca | accaatttat | aacagtgcag | ataaattcaa | aactgaagaa | 840 |
| gattataaag | ctgaaaaatt | attagcgcca | tataaaaag | cgaaaacact | agaaagacaa | 900 |
| gtttatgaat | taaataaat | tcaagataaa | cttcctgaaa | aattaaaggc | tgagtacaag | 960 |
| aagaaattag | aggatacaaa | gaaagcttta | gatgagcaag | tgaaatcagc | tattactgaa | 1020 |
| ttccaaaatg | tacaaccaac | aaatgaaaaa | atgactgatt | acaagatac | aaaatatgtt | 1080 |
| gtttatgaaa | gtgttgagaa | taacgaatct | atgatggata | cttttgttaa | acaccctatt | 1140 |
| aaaacaggta | tgcttaacgg | caaaaaatat | atggtcatgg | aaactactaa | tgacgattac | 1200 |
| tggaaagatt | tcatggttga | aggtcaacgt | gttagaacta | taagcaaaga | tgctaaaaat | 1260 |
| aatactagaa | caattatttt | cccatatgtt | gaaggtaaaa | ctctatatga | tgctatcgtt | 1320 |
| aaagttcacg | taaaacgat | tgattatgat | ggacaatacc | atgtcagaat | cgttgataaa | 1380 |
| gaagcattta | caaaagccaa | taccgataaa | tctaacaaaa | agaacaaca | agataactca | 1440 |
| gctaagaagg | aagctactcc | agctacgcct | agcaaaccaa | caccatcacc | tgttgaaaaa | 1500 |
| gaatcacaaa | aacaagacag | ccaaaaagat | gacaataaac | aattaccaag | tgttgaaaaa | 1560 |
| gaaaatgacg | catctagtga | gtcaggtaaa | gacaaaacgc | ctgctacaaa | accaactaaa | 1620 |

-continued

```
ggtgaagtag aatcaagtag tacaactcca actaaggtag tatctacgac tcaaaatgtt    1680
gcaaaaccaa caactgcttc atcaaaaaca acaaagatg ttgttcaaac ttcagcaggt     1740
tctagcgaag caaagatag tgctccatta caaaaagcaa acattaaaaa cacaaatgat     1800
ggacacactc aaagccaaaa caataaaaat acacaagaaa ataaagcaaa atcattacca    1860
caaactggtg aagaatcaaa taagatatg acattaccat taatggcatt attagcttta    1920
agtagcatcg ttgcattcgt attacctaga aaacgtaaaa actaa                   1965
```

<210> SEQ ID NO 10
<211> LENGTH: 654
<212> TYPE: PRT
<213> ORGANISM: Staphylococcus epidermidis

<400> SEQUENCE: 10

```
Tyr Thr Ile Arg Ser Cys Phe Tyr Asn Met Asn Lys Gln Gln Lys Glu
1               5                   10                  15

Phe Lys Ser Phe Tyr Ser Ile Arg Lys Ser Ser Leu Gly Val Ala Ser
            20                  25                  30

Val Ala Ile Ser Thr Leu Leu Leu Met Ser Asn Gly Glu Ala Gln
        35                  40                  45

Ala Ala Ala Glu Glu Thr Gly Gly Thr Asn Thr Glu Ala Gln Pro Lys
    50                  55                  60

Thr Glu Ala Val Ala Ser Pro Thr Thr Thr Ser Glu Lys Ala Pro Glu
65                  70                  75                  80

Thr Lys Pro Val Ala Asn Ala Val Ser Val Ser Asn Lys Glu Val Glu
                85                  90                  95

Ala Pro Thr Ser Glu Thr Lys Glu Ala Lys Glu Val Lys Glu Val Lys
            100                 105                 110

Ala Pro Lys Glu Thr Lys Glu Val Lys Pro Ala Ala Lys Ala Thr Asn
        115                 120                 125

Asn Thr Tyr Pro Ile Leu Asn Gln Glu Leu Arg Glu Ala Ile Lys Asn
    130                 135                 140

Pro Ala Ile Lys Asp Lys Asp His Ser Ala Pro Asn Ser Arg Pro Ile
145                 150                 155                 160

Asp Phe Glu Met Lys Lys Lys Asp Gly Thr Gln Gln Phe Tyr His Tyr
                165                 170                 175

Ala Ser Ser Val Lys Pro Ala Arg Val Ile Phe Thr Asp Ser Lys Pro
            180                 185                 190

Glu Ile Glu Leu Gly Leu Gln Ser Gly Gln Phe Trp Arg Lys Phe Glu
        195                 200                 205

Val Tyr Glu Gly Asp Lys Lys Leu Pro Ile Lys Leu Val Ser Tyr Asp
    210                 215                 220

Thr Val Lys Asp Tyr Ala Tyr Ile Arg Phe Ser Val Ser Asn Gly Thr
225                 230                 235                 240

Lys Ala Val Lys Ile Val Ser Ser Thr His Phe Asn Asn Lys Glu Glu
                245                 250                 255

Lys Tyr Asp Tyr Thr Leu Met Glu Phe Ala Gln Pro Ile Tyr Asn Ser
            260                 265                 270

Ala Asp Lys Phe Lys Thr Glu Glu Asp Tyr Lys Ala Glu Lys Leu Leu
        275                 280                 285

Ala Pro Tyr Lys Lys Ala Lys Thr Leu Glu Arg Gln Val Tyr Glu Leu
    290                 295                 300

Asn Lys Ile Gln Asp Lys Leu Pro Glu Lys Leu Lys Ala Glu Tyr Lys
```

| | | | | | | | | | | | |
|---|---|---|---|---|---|---|---|---|---|---|---|
| | | | 305 | | | 310 | | | 315 | | 320 |
| Lys | Lys | Leu | Glu | Asp | Thr | Lys | Lys | Ala | Leu | Asp | Glu | Gln | Val | Lys | Ser |

Lys Lys Leu Glu Asp Thr Lys Lys Ala Leu Asp Glu Gln Val Lys Ser
305                 310                 315                 320

Ala Ile Thr Glu Phe Gln Asn Val Gln Pro Thr Asn Glu Lys Met Thr
            325                 330                 335
        340                 345                 350

Asp Leu Gln Asp Thr Lys Tyr Val Val Tyr Glu Ser Val Glu Asn Asn
            355                 360                 365

Glu Ser Met Met Asp Thr Phe Val Lys His Pro Ile Lys Thr Gly Met
        370                 375                 380

Leu Asn Gly Lys Lys Tyr Met Val Met Glu Thr Thr Asn Asp Asp Tyr
385                 390                 395                 400

Trp Lys Asp Phe Met Val Glu Gly Gln Arg Val Arg Thr Ile Ser Lys
                405                 410                 415

Asp Ala Lys Asn Asn Thr Arg Thr Ile Ile Phe Pro Tyr Val Glu Gly
            420                 425                 430

Lys Thr Leu Tyr Asp Ala Ile Val Lys Val His Val Lys Thr Ile Asp
            435                 440                 445

Tyr Asp Gly Gln Tyr His Val Arg Ile Val Asp Lys Glu Ala Phe Thr
450                 455                 460

Lys Ala Asn Thr Asp Lys Ser Asn Lys Lys Glu Gln Gln Asp Asn Ser
465                 470                 475                 480

Ala Lys Lys Glu Ala Thr Pro Ala Thr Pro Ser Lys Pro Thr Pro Ser
                485                 490                 495

Pro Val Glu Lys Glu Ser Gln Lys Gln Asp Ser Gln Lys Asp Asp Asn
            500                 505                 510

Lys Gln Leu Pro Ser Val Glu Lys Glu Asn Asp Ala Ser Ser Glu Ser
            515                 520                 525

Gly Lys Asp Lys Thr Pro Ala Thr Lys Pro Thr Lys Gly Glu Val Glu
        530                 535                 540

Ser Ser Ser Thr Thr Pro Thr Lys Val Val Ser Thr Thr Gln Asn Val
545                 550                 555                 560

Ala Lys Pro Thr Thr Ala Ser Ser Lys Thr Thr Lys Asp Val Val Gln
                565                 570                 575

Thr Ser Ala Gly Ser Ser Glu Ala Lys Asp Ser Ala Pro Leu Gln Lys
            580                 585                 590

Ala Asn Ile Lys Asn Thr Asn Asp Gly His Thr Gln Ser Gln Asn Asn
            595                 600                 605

Lys Asn Thr Gln Glu Asn Lys Ala Lys Ser Leu Pro Gln Thr Gly Glu
    610                 615                 620

Glu Ser Asn Lys Asp Met Thr Leu Pro Leu Met Ala Leu Leu Ala Leu
625                 630                 635                 640

Ser Ser Ile Val Ala Phe Val Leu Pro Arg Lys Arg Lys Asn
                645                 650

<210> SEQ ID NO 11
<211> LENGTH: 2406
<212> TYPE: DNA
<213> ORGANISM: Staphylococcus epidermidis

<400> SEQUENCE: 11
tttataaata atttacataa aatcaatcat tttaatataa ggattatgat aaatatattgg     60 tgtatgacag ttaatggagg gaacgaaatg aaagctttat tacttaaaac aagtgtatgg    120
ctcgttttgc ttttagtgt aatgggatta tggcaagtct cgaacgcggc tgagcagcat    180

```
acaccaatga aagcacatgc agtaacaacg atagacaaag caacaacaga taagcaacaa      240
gtaccgccaa caaaggaagc ggctcatcat tctggcaaag aagcggcaac caacgtatca      300
gcatcagcgc agggaacagc tgatgataca acagcaaag taacatccaa cgcaccatct       360
aacaaaccat ctacagtagt ttcaacaaaa gtaaacgaaa cacgcgacgt agatacacaa      420
caagcctcaa cacaaaaacc aactcacaca gcaacgttca aattatcaaa tgctaaaaca      480
gcatcacttt caccacgaat gtttgctgct aatgcaccac aaacaacaac acataaaata     540
ttacatacaa atgatatcca tggccgacta gccgaagaaa aagggcgtgt catcggtatg      600
gctaaattaa aaacagtaaa agaacaagaa agcctgatt taatgttaga cgcaggagac      660
gccttccaag gtttaccact ttcaaaccag tctaaaggtg aagaaatggc taaagcaatg      720
aatgcagtag gttatgatgc tatggcagtc ggtaaccatg aatttgactt tggatacgat      780
cagttgaaaa agttagaggg tatgttagac ttcccgatgc taagtactaa cgtttataaa      840
gatgaaaaac gcgcgtttaa gccttcaacg attgtaacaa aaaatggtat tcgttatgga      900
attattggtg taacgacacc agaaacaaag acgaaaacaa gacctgaagg cattaaaggc      960
gttgaattta gagatccatt acaaagtgtg acagcggaaa tgatgcgtat ttataaagac      1020
gtagatacat tgttgttat atcacattta ggaattgatc cttcaacaca agaaacatgg      1080
cgtggtgatt acttagtgaa acaattaagt caaaatccac aattgaagaa acgtattaca      1140
gttattgatg gtcattcaca tacagtactt caaaatggtc aaatttataa caatgatgca      1200
ttggcacaaa caggtacagc acttgcgaat atcggtaaga ttacatttaa ttatcgcaat      1260
ggagaggtat cgaatattaa accgtcattg attaatgtta aagacgttga aaatgtaaca      1320
ccgaacaaag cattagctga acaaattaat caagctgatc aaacatttag agcacaaact      1380
gcagaggtaa ttattccaaa caataccatt gatttcaaag gagaaagaga tgacgttaga      1440
acgcgtgaaa caaatttagg aaacgcgatt gcagatgcta tggaagcgta tggcgttaag      1500
aatttctcta aaaagactga ctttgccgtg acaaatggtg gaggtattcg tgcctctatc      1560
gcaaaaggta aggtgacacg ctatgattta atctcagtat taccatttgg aaatacgatt      1620
gcgcaaattg atgtaaaagg ttcagacgtc tggacggctt tcgaacatag tttaggcgca      1680
ccaacaacac aaaaggacgg taagacagtg ttaacagcga atggcggttt actacatatc      1740
tctgattcaa tccgtgttta ctatgatata aataaaccgt ctggcaaacg aattaatgct      1800
attcaaattt taaataaaga gacagttaag tttgaaaata ttgatttaaa acgtgtatat      1860
cacgtaacga tgaatgactt cacagcatca ggtggcgacg gatatagtat gttcggtggt      1920
cctagagaag aaggtatttc attagatcaa gtactagcaa gttatttaaa aacagctaac      1980
ttagctaagt atgatacgac agaaccacaa cgtatgttat taggtaaacc agcagtaagt      2040
gaacaaccag ctaaaggaca acaaggtagc aaaggtagta agtctggtaa agatacacaa      2100
ccaattggtg acgacaaagt gatggatcca gcgaaaaaac cagctccagg taaagttgta      2160
ttgttgctag cgcatagagg aactgttagt agcggtacag aaggttctgg tcgcacaata      2220
gaaggagcta ctgtatcaag caagagtggg aaacaattgg ctagaatgtc agtgcctaaa      2280
ggtagcgcgc atgagaaaca gttaccaaaa actggaacta atcaaagttc aagcccagaa      2340
gcgatgtttg tattattagc aggtataggt ttaatcgcga ctgtacgacg tagaaaagct      2400
agctaa                                                                2406
```

<210> SEQ ID NO 12
<211> LENGTH: 801

<212> TYPE: PRT
<213> ORGANISM: Staphylococcus epidermidis

<400> SEQUENCE: 12

```
Phe Ile Asn Asn Leu His Lys Ile Asn His Phe Asn Ile Arg Ile Met
1               5                   10                  15

Ile Ile Tyr Trp Cys Met Thr Val Asn Gly Asn Glu Met Lys Ala
            20                  25                  30

Leu Leu Leu Lys Thr Ser Val Trp Leu Val Leu Phe Ser Val Met
            35                  40                  45

Gly Leu Trp Gln Val Ser Asn Ala Ala Glu Gln His Thr Pro Met Lys
    50                  55                  60

Ala His Ala Val Thr Thr Ile Asp Lys Ala Thr Thr Asp Lys Gln Gln
65                  70                  75                  80

Val Pro Pro Thr Lys Glu Ala Ala His His Ser Gly Lys Glu Ala Ala
                85                  90                  95

Thr Asn Val Ser Ala Ser Ala Gln Gly Thr Ala Asp Asp Thr Asn Ser
            100                 105                 110

Lys Val Thr Ser Asn Ala Pro Ser Asn Lys Pro Ser Thr Val Val Ser
        115                 120                 125

Thr Lys Val Asn Glu Thr Arg Asp Val Asp Thr Gln Gln Ala Ser Thr
130                 135                 140

Gln Lys Pro Thr His Thr Ala Thr Phe Lys Leu Ser Asn Ala Lys Thr
145                 150                 155                 160

Ala Ser Leu Ser Pro Arg Met Phe Ala Ala Asn Ala Pro Gln Thr Thr
            165                 170                 175

Thr His Lys Ile Leu His Thr Asn Asp Ile His Gly Arg Leu Ala Glu
        180                 185                 190

Glu Lys Gly Arg Val Ile Gly Met Ala Lys Leu Lys Thr Val Lys Glu
    195                 200                 205

Gln Glu Lys Pro Asp Leu Met Leu Asp Ala Gly Asp Ala Phe Gln Gly
    210                 215                 220

Leu Pro Leu Ser Asn Gln Ser Lys Gly Glu Glu Met Ala Lys Ala Met
225                 230                 235                 240

Asn Ala Val Gly Tyr Asp Ala Met Ala Val Gly Asn His Glu Phe Asp
            245                 250                 255

Phe Gly Tyr Asp Gln Leu Lys Lys Leu Glu Gly Met Leu Asp Phe Pro
        260                 265                 270

Met Leu Ser Thr Asn Val Tyr Lys Asp Gly Lys Arg Ala Phe Lys Pro
        275                 280                 285

Ser Thr Ile Val Thr Lys Asn Gly Ile Arg Tyr Gly Ile Ile Gly Val
    290                 295                 300

Thr Thr Pro Glu Thr Lys Thr Lys Thr Arg Pro Glu Gly Ile Lys Gly
305                 310                 315                 320

Val Glu Phe Arg Asp Pro Leu Gln Ser Val Thr Ala Glu Met Met Arg
                325                 330                 335

Ile Tyr Lys Asp Val Asp Thr Phe Val Val Ile Ser His Leu Gly Ile
            340                 345                 350

Asp Pro Ser Thr Gln Glu Thr Trp Arg Gly Asp Tyr Leu Val Lys Gln
        355                 360                 365

Leu Ser Gln Asn Pro Gln Leu Lys Lys Arg Ile Thr Val Ile Asp Gly
    370                 375                 380

His Ser His Thr Val Leu Gln Asn Gly Gln Ile Tyr Asn Asn Asp Ala
385                 390                 395                 400
```

```
Leu Ala Gln Thr Gly Thr Ala Leu Ala Asn Ile Gly Lys Ile Thr Phe
            405                 410                 415
Asn Tyr Arg Asn Gly Glu Val Ser Asn Ile Lys Pro Ser Leu Ile Asn
        420                 425                 430
Val Lys Asp Val Glu Asn Val Thr Pro Asn Lys Ala Leu Ala Glu Gln
        435                 440                 445
Ile Asn Gln Ala Asp Gln Thr Phe Arg Ala Gln Thr Ala Glu Val Ile
    450                 455                 460
Ile Pro Asn Asn Thr Ile Asp Phe Lys Gly Glu Arg Asp Asp Val Arg
465                 470                 475                 480
Thr Arg Glu Thr Asn Leu Gly Asn Ala Ile Ala Asp Ala Met Glu Ala
            485                 490                 495
Tyr Gly Val Lys Asn Phe Ser Lys Lys Thr Asp Phe Ala Val Thr Asn
            500                 505                 510
Gly Gly Gly Ile Arg Ala Ser Ile Ala Lys Gly Lys Val Thr Arg Tyr
        515                 520                 525
Asp Leu Ile Ser Val Leu Pro Phe Gly Asn Thr Ile Ala Gln Ile Asp
    530                 535                 540
Val Lys Gly Ser Asp Val Trp Thr Ala Phe Glu His Ser Leu Gly Ala
545                 550                 555                 560
Pro Thr Thr Gln Lys Asp Gly Lys Thr Val Leu Thr Ala Asn Gly Gly
            565                 570                 575
Leu Leu His Ile Ser Asp Ser Ile Arg Val Tyr Tyr Asp Ile Asn Lys
            580                 585                 590
Pro Ser Gly Lys Arg Ile Asn Ala Ile Gln Ile Leu Asn Lys Glu Thr
        595                 600                 605
Gly Lys Phe Glu Asn Ile Asp Leu Lys Arg Val Tyr His Val Thr Met
        610                 615                 620
Asn Asp Phe Thr Ala Ser Gly Asp Gly Tyr Ser Met Phe Gly Gly
625                 630                 635                 640
Pro Arg Glu Glu Gly Ile Ser Leu Asp Gln Val Leu Ala Ser Tyr Leu
            645                 650                 655
Lys Thr Ala Asn Leu Ala Lys Tyr Asp Thr Thr Glu Pro Gln Arg Met
            660                 665                 670
Leu Leu Gly Lys Pro Ala Val Ser Glu Gln Pro Ala Lys Gly Gln Gln
        675                 680                 685
Gly Ser Lys Gly Ser Lys Ser Gly Lys Asp Thr Gln Pro Ile Gly Asp
    690                 695                 700
Asp Lys Val Met Asp Pro Ala Lys Lys Pro Ala Pro Gly Lys Val Val
705                 710                 715                 720
Leu Leu Leu Ala His Arg Gly Thr Val Ser Ser Gly Thr Glu Gly Ser
            725                 730                 735
Gly Arg Thr Ile Glu Gly Ala Thr Val Ser Ser Lys Ser Gly Lys Gln
            740                 745                 750
Leu Ala Arg Met Ser Val Pro Lys Gly Ser Ala His Glu Lys Gln Leu
        755                 760                 765
Pro Lys Thr Gly Thr Asn Gln Ser Ser Pro Glu Ala Met Phe Val
    770                 775                 780
Leu Leu Ala Gly Ile Gly Leu Ile Ala Thr Val Arg Arg Arg Lys Ala
785                 790                 795                 800
Ser
```

<210> SEQ ID NO 13
<211> LENGTH: 4914
<212> TYPE: DNA
<213> ORGANISM: Staphylococcus epidermidis

<400> SEQUENCE: 13

```
agtggaaaat atgaaaaag gagtatgcaa atgagagata agaaaggacc ggtaaataaa        60
agagtagatt ttctatcaaa taaattgaat aaatattcaa taagaaaatt tacagttgga       120
acagcatcta ttttaattgg ctcactaatg tatttgggaa ctcaacaaga ggcagaagca       180
gctgaaaaca atattgagaa tccaactaca ttaaaagata atgtccaatc aaaagaagtg       240
aagattgaag aagtaacaaa caaagacact gcaccacagg gtgtagaagc taaatctgaa       300
gtaacttcaa acaaagacac aatcgaacat gaaccatcag taaaagctga agatatatca       360
aaaaaggagg atacaccaaa agaagtagct gatgttgctg aagttcagcc gaaatcgtca       420
gtcactcata acgcagagac acctaaggtt agaaaagctc gttctgttga tgaaggctct       480
tttgatatta caagagattc taaaaatgta gttgaatcta ccccaattac aattcaaggt       540
aaagaacatt ttgaaggtta cggaagtgtt gatatacaaa aaaaaccaac agatttaggg       600
gtatcagagg taaccaggtt taatgttggt aatgaaagta atggtttgat aggagcttta       660
caattaaaaa ataaaataga ttttagtaag gatttcaatt ttaaagttag agtggcaaat       720
aaccatcaat caaataccac aggtgctgat ggttgggggt tcttatttag taaaggaaat       780
gcagaagaat atttaactaa tggtggaatc cttggggata aaggtctggt aaattcaggc       840
ggatttaaaa ttgatactgg atacatttat acaagttcca tggacaaaac tgaaaagcaa       900
gctggacaag gttatagagg atacggagct tttgtgaaaa atgacagttc tggtaattca       960
caaatggttg gagaaaatat tgataaatca aaaactaatt ttttaaacta tgcggacaat      1020
tcaactaata catcagatgg aaagtttcat gggcaacgtt taaatgatgt catcttaact      1080
tatgttgctt caactggtaa aatgagagca gaatatgctg gtaaaacttg ggagacttca      1140
ataacagatt taggtttatc taaaaatcag gcatataatt tcttaattac atctagtcaa      1200
agatggggcc ttaatcaagg gataaatgca atggctggaa tgagaactga cttgaaaggt      1260
tcagagttta cttttacacc agaagcgcca aaacaataa cagaattaga aaaaaagtt      1320
gaagagattc cattcaagaa agaacgtaaa tttaatccgg atttagcacc agggacagaa      1380
aaagtaacaa gagaaggaca aaaggtgag aagacaataa cgacaccaac actaaaaat      1440
ccattaactg gagtaattat tagtaaaggt gaaccaaaag aagagattac aaaagatccg      1500
attaatgaat taacagaata cggacctgaa acaatagcgc caggtcatcg agacgaattt      1560
gatccgaagt taccaacagg agagaaagag gaagttccag gtaaaccagg aattaagaat      1620
ccagaaacag gagacgtagt tagaccgccg gtcgatagcg taacaaaata tggacctgta      1680
aaaggagact cgattgtaga aaagaagag attccattcg agaaagaacg taaatttaat      1740
cctgatttag caccagggac agaaaaagta acaagagaag gacaaaaagg tgagaagaca      1800
ataacgacgc caacactaaa aaatccatta actggagaaa ttattagtaa aggtgaatcg      1860
aaagaagaaa tcacaaaaga tccgattaat gaattaacag aatacggacc agaaacgata      1920
acaccaggtc atcgagacga atttgatccg aagttaccaa caggagagaa agaggaagtt      1980
ccaggtaaac aggaattaa gaatccagaa acaggagatg tagttagacc accggtcgat      2040
agcgtaacaa aatatggacc tgtaaaagga gactcgattg tagaaaaaga gagattcca      2100
ttcgagaaag aacgtaaatt taatcctgat ttagcaccag ggacagaaaa agtaacaaga      2160
```

```
gaaggacaaa aaggtgagaa gacaataacg acaccaacac taaaaaatcc attaactgga    2220
gtaattatta gtaaaggtga accaaaagaa gaaatcacaa aagatccgat taatgaatta    2280
acagaatacg gaccagaaac gataacacca ggtcatcgag acgaatttga tccgaagtta    2340
ccaacaggag agaaagaaga agttccaggt aaaccaggaa ttaagaatcc agaaacagga    2400
gacgtagtta gaccaccggt cgatagcgta acaaaatatg gacctgtaaa aggagactcg    2460
attgtagaaa aagaagagat tccattcaag aaagaacgta aatttaatcc ggatttagca    2520
ccagggacag aaaagtaac aagagaagga caaaaaggtg agaagacaat aacgacgcca    2580
acactaaaaa atccattaac tggagaaatt attagtaaag gtgaatcgaa agaagaaatc    2640
acaaaagatc cgattaatga attaacagaa tacggaccag aaacgataac accaggtcat    2700
cgagacgaat ttgatccgaa gttaccaaca ggagagaaag aggaagttcc aggtaaacca    2760
ggaattaaga atccagaaac aggagatgta gttagaccac cggtcgatag cgtaacaaaa    2820
tatggacctg taaaggaga ctcgattgta gaaaagaag agattccatt cgagaaagaa    2880
cgtaaattta atcctgattt agcaccaggg acagaaaag taacaagaga aggacaaaaa    2940
ggtgagaaga caataacgac gccaacacta aaaaatccat taactggaga aattattagt    3000
aaaggtgaat cgaaagaaga aatcacaaaa gatccgatta atgaattaac agaatacgga    3060
ccagaaacga taacaccagg tcatcgagac gaatttgatc cgaagttacc aacaggagag    3120
aaagaggaag ttccaggtaa accaggaatt aagaatccag aaacaggaga cgtagttaga    3180
ccaccggtcg atagcgtaac aaaatatgga cctgtaaaag gagactcgat tgtagaaaaa    3240
gaagaaattc cattcaagaa agaacgtaaa tttaatcctg atttagcacc agggacagaa    3300
aaagtaacaa gagaaggaca aaaaggtgag aagacaataa cgacgccaac actaaaaaat    3360
ccattaactg gagaaattat tagtaaaggt gaatcgaaag aagaaatcac aaaagatccg    3420
attaatgaat taacagaata cggaccagaa acgataacac caggtcatcg agacgaattt    3480
gatccgaagt taccaacagg agagaaagag gaagttccag gtaaaccagg aattaagaat    3540
ccagaaacag gagatgtagt tagaccaccg gtcgatagcg taacaaaata tggacctgta    3600
aaaggagact cgattgtaga aaagaagaa attccattcg agaaagaacg taaatttaat    3660
cctgatttag caccagggac agaaaaagta acaagagaag gacaaaaagg tgagaagaca    3720
ataacgacgc caacactaaa aaatccatta actggagaaa ttattagtaa aggtgaatcg    3780
aaagaagaaa tcacaaaaga tccgattaat gaattaacag aatacggacc agaaacgata    3840
acaccaggtc atcgagacga atttgatccg aagttaccaa caggagagaa agaggaagtt    3900
ccaggtaaac caggaattaa gaatccagaa acaggagatg tagttagacc accggtcgat    3960
agcgtaacaa aatatggacc tgtaaaagga gactcgattg tagaaaaaga gaaattcca    4020 ttcgagaaag aacgtaaatt taatcctgat ttagcaccag ggacagaaaa agtaacaaga    4080
gaaggacaaa aaggtgagaa gacaataacg acgccaacac taaaaaatcc attaactgga    4140
gaaattatta gtaaaggtga atcgaaagaa gaaatcacaa aagatccagt taatgaatta    4200
acagaattcg gtggcgagaa ataccgcaa ggtcataaag atatctttga tccaaactta    4260
ccaacagatc aaacggaaaa agtaccaggt aaaccaggaa tcaagaatcc agacacagga    4320
aaagtgatcg aagagccagt ggatgatgtg attaaacacg gaccaaaaac gggtacacca    4380
gaaacaaaaa cagtagagat accgtttgaa acaaaacgtg agtttaatcc aaaattacaa    4440
cctggtgaag agcgagtgaa acaagaagga caaccaggaa gtaagacaat cacaacacca    4500
atcacagtga acccattaac aggtgaaaaa gttggcgagg gtcaaccaac agaagagatc    4560
```

```
acaaaacaac cagtagataa gattgtagag ttcggtggag agaaaccaaa agatccaaaa    4620
ggacctgaaa acccagagaa gccgagcaga ccaactcatc caagtggccc agtaaatcct    4680
aacaatccag gattatcgaa agacagagca aaaccaaatg gcccagttca ttcaatggat    4740
aaaaatgata aagttaaaaa atctaaaatt gctaaagaat cagtagctaa tcaagagaaa    4800
aaacgagcag aattaccaaa aacaggttta gaaagcacgc aaaaaggttt gatctttagt    4860
agtataattg gaattgctgg attaatgtta ttggctcgta gaagaaagaa ttaa          4914
```

<210> SEQ ID NO 14
<211> LENGTH: 1637
<212> TYPE: PRT
<213> ORGANISM: Staphylococcus epidermidis

<400> SEQUENCE: 14

```
Ser Gly Lys Tyr Gly Lys Arg Ser Met Gln Met Arg Asp Lys Lys Gly
1               5                   10                  15

Pro Val Asn Lys Arg Val Asp Phe Leu Ser Asn Lys Leu Asn Lys Tyr
            20                  25                  30

Ser Ile Arg Lys Phe Thr Val Gly Thr Ala Ser Ile Leu Ile Gly Ser
        35                  40                  45

Leu Met Tyr Leu Gly Thr Gln Gln Glu Ala Glu Ala Glu Asn Asn
    50                  55                  60

Ile Glu Asn Pro Thr Thr Leu Lys Asp Asn Val Gln Ser Lys Glu Val
65                  70                  75                  80

Lys Ile Glu Glu Val Thr Asn Lys Asp Thr Ala Pro Gln Gly Val Glu
                85                  90                  95

Ala Lys Ser Glu Val Thr Ser Asn Lys Asp Thr Ile Glu His Glu Pro
            100                 105                 110

Ser Val Lys Ala Glu Asp Ile Ser Lys Lys Glu Asp Thr Pro Lys Glu
        115                 120                 125

Val Ala Asp Val Ala Glu Val Gln Pro Lys Ser Ser Val Thr His Asn
    130                 135                 140

Ala Glu Thr Pro Lys Val Arg Lys Ala Arg Ser Val Asp Glu Gly Ser
145                 150                 155                 160

Phe Asp Ile Thr Arg Asp Ser Lys Asn Val Val Glu Ser Thr Pro Ile
                165                 170                 175

Thr Ile Gln Gly Lys Glu His Phe Glu Gly Tyr Gly Ser Val Asp Ile
            180                 185                 190

Gln Lys Lys Pro Thr Asp Leu Gly Val Ser Glu Val Thr Arg Phe Asn
        195                 200                 205

Val Gly Asn Glu Ser Asn Gly Leu Ile Gly Ala Leu Gln Leu Lys Asn
    210                 215                 220

Lys Ile Asp Phe Ser Lys Asp Phe Asn Phe Lys Val Arg Val Ala Asn
225                 230                 235                 240

Asn His Gln Ser Asn Thr Thr Gly Ala Asp Gly Trp Gly Phe Leu Phe
                245                 250                 255

Ser Lys Gly Asn Ala Glu Glu Tyr Leu Thr Asn Gly Gly Ile Leu Gly
            260                 265                 270

Asp Lys Gly Leu Val Asn Ser Gly Phe Lys Ile Asp Thr Gly Tyr
        275                 280                 285

Ile Tyr Thr Ser Ser Met Asp Lys Thr Glu Lys Gln Ala Gly Gln Gly
    290                 295                 300

Tyr Arg Gly Tyr Gly Ala Phe Val Lys Asn Asp Ser Ser Gly Asn Ser
```

-continued

```
            305                 310                 315                 320
Gln Met Val Gly Glu Asn Ile Asp Lys Ser Lys Thr Asn Phe Leu Asn
                325                 330                 335
Tyr Ala Asp Asn Ser Thr Asn Thr Ser Asp Gly Lys Phe His Gly Gln
                340                 345                 350
Arg Leu Asn Asp Val Ile Leu Thr Tyr Val Ala Ser Thr Gly Lys Met
                355                 360                 365
Arg Ala Glu Tyr Ala Gly Lys Thr Trp Glu Thr Ser Ile Thr Asp Leu
                370                 375                 380
Gly Leu Ser Lys Asn Gln Ala Tyr Asn Phe Leu Ile Thr Ser Ser Gln
385                 390                 395                 400
Arg Trp Gly Leu Asn Gln Gly Ile Asn Ala Asn Gly Trp Met Arg Thr
                405                 410                 415
Asp Leu Lys Gly Ser Glu Phe Thr Phe Thr Pro Glu Ala Pro Lys Thr
                420                 425                 430
Ile Thr Glu Leu Glu Lys Lys Val Glu Ile Pro Phe Lys Lys Glu
                435                 440                 445
Arg Lys Phe Asn Pro Asp Leu Ala Pro Gly Thr Glu Lys Val Thr Arg
450                 455                 460
Glu Gly Gln Lys Gly Glu Lys Thr Ile Thr Thr Pro Thr Leu Lys Asn
465                 470                 475                 480
Pro Leu Thr Gly Val Ile Ile Ser Lys Gly Glu Pro Lys Glu Glu Ile
                485                 490                 495
Thr Lys Asp Pro Ile Asn Glu Leu Thr Glu Tyr Gly Pro Glu Thr Ile
                500                 505                 510
Ala Pro Gly His Arg Asp Glu Phe Asp Pro Lys Leu Pro Thr Gly Glu
                515                 520                 525
Lys Glu Glu Val Pro Gly Lys Pro Gly Ile Lys Asn Pro Glu Thr Gly
                530                 535                 540
Asp Val Val Arg Pro Pro Val Asp Ser Val Thr Lys Tyr Gly Pro Val
545                 550                 555                 560
Lys Gly Asp Ser Ile Val Glu Lys Glu Ile Pro Phe Glu Lys Glu
                565                 570                 575
Arg Lys Phe Asn Pro Asp Leu Ala Pro Gly Thr Glu Lys Val Thr Arg
                580                 585                 590
Glu Gly Gln Lys Gly Glu Lys Thr Ile Thr Thr Pro Thr Leu Lys Asn
                595                 600                 605
Pro Leu Thr Gly Glu Ile Ile Ser Lys Gly Glu Ser Lys Glu Glu Ile
                610                 615                 620
Thr Lys Asp Pro Ile Asn Glu Leu Thr Glu Tyr Gly Pro Glu Thr Ile
625                 630                 635                 640
Thr Pro Gly His Arg Asp Glu Phe Asp Pro Lys Leu Pro Thr Gly Glu
                645                 650                 655
Lys Glu Glu Val Pro Gly Lys Pro Gly Ile Lys Asn Pro Glu Thr Gly
                660                 665                 670
Asp Val Val Arg Pro Pro Val Asp Ser Val Thr Lys Tyr Gly Pro Val
                675                 680                 685
Lys Gly Asp Ser Ile Val Glu Lys Glu Ile Pro Phe Glu Lys Glu
                690                 695                 700
Arg Lys Phe Asn Pro Asp Leu Ala Pro Gly Thr Glu Lys Val Thr Arg
705                 710                 715                 720
Glu Gly Gln Lys Gly Glu Lys Thr Ile Thr Thr Pro Thr Leu Lys Asn
                725                 730                 735
```

-continued

Pro Leu Thr Gly Val Ile Ile Ser Lys Gly Glu Pro Lys Glu Glu Ile
              740                 745                 750

Thr Lys Asp Pro Ile Asn Glu Leu Thr Glu Tyr Gly Pro Glu Thr Ile
              755                 760                 765

Thr Pro Gly His Arg Asp Glu Phe Asp Pro Lys Leu Pro Thr Gly Glu
              770                 775                 780

Lys Glu Glu Val Pro Gly Lys Pro Gly Ile Lys Asn Pro Glu Thr Gly
785                 790                 795                 800

Asp Val Val Arg Pro Pro Val Asp Ser Val Thr Lys Tyr Gly Pro Val
              805                 810                 815

Lys Gly Asp Ser Ile Val Glu Lys Glu Ile Pro Phe Glu Lys Lys Glu
              820                 825                 830

Arg Lys Phe Asn Pro Asp Leu Ala Pro Gly Thr Glu Lys Val Thr Arg
              835                 840                 845

Glu Gly Gln Lys Gly Glu Lys Thr Ile Thr Thr Pro Thr Leu Lys Asn
              850                 855                 860

Pro Leu Thr Gly Glu Ile Ile Ser Lys Gly Glu Ser Lys Glu Glu Ile
865                 870                 875                 880

Thr Lys Asp Pro Ile Asn Glu Leu Thr Glu Tyr Gly Pro Glu Thr Ile
              885                 890                 895

Thr Pro Gly His Arg Asp Glu Phe Asp Pro Lys Leu Pro Thr Gly Glu
              900                 905                 910

Lys Glu Glu Val Pro Gly Lys Pro Gly Ile Lys Asn Pro Glu Thr Gly
              915                 920                 925

Asp Val Val Arg Pro Pro Val Asp Ser Val Thr Lys Tyr Gly Pro Val
930                 935                 940

Lys Gly Asp Ser Ile Val Glu Lys Glu Ile Pro Phe Glu Lys Lys Glu
945                 950                 955                 960

Arg Lys Phe Asn Pro Asp Leu Ala Pro Gly Thr Glu Lys Val Thr Arg
              965                 970                 975

Glu Gly Gln Lys Gly Glu Lys Thr Ile Thr Thr Pro Thr Leu Lys Asn
              980                 985                 990

Pro Leu Thr Gly Glu Ile Ile Ser  Lys Gly Glu Ser Lys  Glu Glu Ile
              995                 1000                1005

Thr Lys  Asp Pro Ile Asn Glu  Leu Thr Glu Tyr Gly  Pro Glu Thr
              1010                1015                1020

Ile Thr  Pro Gly His Arg Asp  Glu Phe Asp Pro Lys  Leu Pro Thr
              1025                1030                1035

Gly Glu  Lys Glu Glu Val Pro  Gly Lys Pro Gly Ile  Lys Asn Pro
              1040                1045                1050

Glu Thr  Gly Asp Val Val Arg  Pro Pro Val Asp Ser  Val Thr Lys
              1055                1060                1065

Tyr Gly  Pro Val Lys Gly Asp  Ser Ile Val Glu Lys  Glu Glu Ile
              1070                1075                1080

Pro Phe  Lys Lys Glu Arg Lys  Phe Asn Pro Asp Leu  Ala Pro Gly
              1085                1090                1095

Thr Glu  Lys Val Thr Arg Glu  Gly Gln Lys Gly Glu  Lys Thr Ile
              1100                1105                1110

Thr Thr  Pro Thr Leu Lys Asn  Pro Leu Thr Gly Glu  Ile Ile Ser
              1115                1120                1125

Lys Gly  Glu Ser Lys Glu Glu  Ile Thr Lys Asp Pro  Ile Asn Glu
              1130                1135                1140

-continued

| | | | | | | | | | | | |
|---|---|---|---|---|---|---|---|---|---|---|---|
| Leu | Thr | Glu | Tyr | Gly | Pro | Glu | Thr | Ile | Thr | Pro | Gly | His | Arg | Asp |
| | 1145 | | | | 1150 | | | | 1155 | | |

Leu Thr Glu Tyr Gly Pro Glu Thr Ile Thr Pro Gly His Arg Asp
    1145                1150                1155

Glu Phe Asp Pro Lys Leu Pro Thr Gly Glu Lys Glu Glu Val Pro
    1160                1165                1170

Gly Lys Pro Gly Ile Lys Asn Pro Glu Thr Gly Asp Val Val Arg
    1175                1180                1185

Pro Pro Val Asp Ser Val Thr Lys Tyr Gly Pro Val Lys Gly Asp
    1190                1195                1200

Ser Ile Val Glu Lys Glu Glu Ile Pro Phe Glu Lys Glu Arg Lys
    1205                1210                1215

Phe Asn Pro Asp Leu Ala Pro Gly Thr Glu Lys Val Thr Arg Glu
    1220                1225                1230

Gly Gln Lys Gly Glu Lys Thr Ile Thr Thr Pro Thr Leu Lys Asn
    1235                1240                1245

Pro Leu Thr Gly Glu Ile Ile Ser Lys Gly Glu Ser Lys Glu Glu
    1250                1255                1260

Ile Thr Lys Asp Pro Ile Asn Glu Leu Thr Glu Tyr Gly Pro Glu
    1265                1270                1275

Thr Ile Thr Pro Gly His Arg Asp Glu Phe Asp Pro Lys Leu Pro
    1280                1285                1290

Thr Gly Glu Lys Glu Glu Val Pro Gly Lys Pro Gly Ile Lys Asn
    1295                1300                1305

Pro Glu Thr Gly Asp Val Val Arg Pro Pro Val Asp Ser Val Thr
    1310                1315                1320

Lys Tyr Gly Pro Val Lys Gly Asp Ser Ile Val Glu Lys Glu Glu
    1325                1330                1335

Ile Pro Phe Glu Lys Glu Arg Lys Phe Asn Pro Asp Leu Ala Pro
    1340                1345                1350

Gly Thr Glu Lys Val Thr Arg Glu Gly Gln Lys Gly Glu Lys Thr
    1355                1360                1365

Ile Thr Thr Pro Thr Leu Lys Asn Pro Leu Thr Gly Glu Ile Ile
    1370                1375                1380

Ser Lys Gly Glu Ser Lys Glu Glu Ile Thr Lys Asp Pro Val Asn
    1385                1390                1395

Glu Leu Thr Glu Phe Gly Gly Glu Lys Ile Pro Gln Gly His Lys
    1400                1405                1410

Asp Ile Phe Asp Pro Asn Leu Pro Thr Asp Gln Thr Glu Lys Val
    1415                1420                1425

Pro Gly Lys Pro Gly Ile Lys Asn Pro Asp Thr Gly Lys Val Ile
    1430                1435                1440

Glu Glu Pro Val Asp Asp Val Ile Lys His Gly Pro Lys Thr Gly
    1445                1450                1455

Thr Pro Glu Thr Lys Thr Val Glu Ile Pro Phe Glu Thr Lys Arg
    1460                1465                1470

Glu Phe Asn Pro Lys Leu Gln Pro Gly Glu Glu Arg Val Lys Gln
    1475                1480                1485

Glu Gly Gln Pro Gly Ser Lys Thr Ile Thr Thr Pro Ile Thr Val
    1490                1495                1500

Asn Pro Leu Thr Gly Glu Lys Val Gly Glu Gly Gln Pro Thr Glu
    1505                1510                1515

Glu Ile Thr Lys Gln Pro Val Asp Lys Ile Val Glu Phe Gly Gly
    1520                1525                1530

Glu Lys Pro Lys Asp Pro Lys Gly Pro Glu Asn Pro Glu Lys Pro

```
          1535                1540                1545
Ser Arg Pro Thr His Pro Ser Gly Pro Val Asn Pro Asn Asn Pro
    1550                1555                1560

Gly Leu Ser Lys Asp Arg Ala Lys Pro Asn Gly Pro Val His Ser
    1565                1570                1575

Met Asp Lys Asn Asp Lys Val Lys Lys Ser Lys Ile Ala Lys Glu
    1580                1585                1590

Ser Val Ala Asn Gln Glu Lys Lys Arg Ala Glu Leu Pro Lys Thr
    1595                1600                1605

Gly Leu Glu Ser Thr Gln Lys Gly Leu Ile Phe Ser Ser Ile Ile
    1610                1615                1620

Gly Ile Ala Gly Leu Met Leu Leu Ala Arg Arg Arg Lys Asn
    1625                1630                1635

<210> SEQ ID NO 15
<211> LENGTH: 1923
<212> TYPE: DNA
<213> ORGANISM: Staphylococcus epidermidis

<400> SEQUENCE: 15
ggaaggagta tgttgatggc taaatatcga gggaaaccgt ttcaattata tgtaaagtta      60
tcgtgttcga caatgatggc gacaagtatc attttaacga atatcttgcc gtacgatgcc    120
caagctgcat ctgaaaagga tactgaaatt acaaaagaga tattatctaa gcaagattta    180
ttagacaaag ttgacaaggc aattcgtcaa attgagcaat aaaacagtt atcggcttca     240
tctaaagaac attataaagc acaactaaat gaagcgaaaa cagcatcgca aatagatgaa    300
atcataaaac gagctaatga gttggatagc aaagacaata aaagttctca cactgaaatg    360
aacggtcaaa gtgatataga cagtaaaatta gatcaattgc ttaaagattt aaatgaggtt    420
tcttcaaatg ttgataggg tcaacaaagt ggcgaggacg atcttaatgc aatgaaaaat    480
gatatgtcac aaacggctac aacaaaacat ggagaaaaag atgataaaaa tgatgaagca    540
atggtaaata aggcgttaga agacctagac catttgaatc agcaaataca caatcgaaa     600
gatgcatcga agatacatc ggaagatcca gcagtgtcta caacagataa taatcatgaa    660
gtagctaaaa cgccaaataa tgatggttct ggacatgttg tgttaaataa attccttca    720
aatgaagaga tcaaagcca tagtaatcga ctcactgata aattacaagg aagcgataaa    780
attaatcatg ctatgattga aaaattagct aaagtaatg cctcaacgca acattacaca    840
tatcataaac tgaatacgtt acaatcttta gatcaacgta ttgcaaatac gcaacttcct    900
aaaaatcaaa atcagactt aatgagcgaa gtaaataaga cgaaagagcg tataaaagt     960
caacgaaata ttattttgga agaacttgca cgtactgatg ataaaaagta tgctacacaa  1020
agcattttag aaagtatatt taataaagac gaggcagtta aaattctaaa agatatacgt   1080
gttgatggta aaacagatca acaaattgca gatcaaatta ctcgtcatat tgatcaatta   1140
tctctgacaa cgagtgatga tttattaacg tcattgattg atcaatcaca agataagtcg   1200
ctattgattt ctcaaatttt acaaacgaaa ttaggaaaag ctgaagcaga taaattggct   1260
aaagattgga cgaataaagg attatcaaat cgccaaatcg ttgaccaatt gaagaaacat   1320
tttgcatcaa ctggcgacac gtcttcgat gatatattaa aagcaatttt gaataatgcc   1380
aaagataaaa aacaagcaat tgaaacgatt ttagcaacac gtatagaaag acaaaaggca   1440
aaattactgg cagatttaat tactaaaata gaaacagatc aaaataaaat ttttaattta   1500
gttaaatcgg cattgaatgg taaagcggat gatttattga atttacaaaa gagactcaat   1560
```

```
caaacgaaaa aagatataga ttatatttta tcaccaatag taaatcgtcc aagtttacta   1620
gatcgattga ataaaaatgg gaaaacgaca gatttaaata agttagcaaa tttaatgaat   1680
caaggatcag atttattaga cagtattcca gatataccca caccaaagcc agaaaagacg   1740
ttaacacttg gtaaaggtaa tggattgtta agtggattat taaatgctga tggtaatgta   1800
tctttgccta aagcgggga aacgataaaa gaacattggt tgccgatatc tgtaattgtt   1860
ggtgcaatgg gtgtactaat gatttggtta tcacgacgca ataagttgaa aaataaagca   1920
taa                                                                1923
```

<210> SEQ ID NO 16
<211> LENGTH: 640
<212> TYPE: PRT
<213> ORGANISM: Staphylococcus epidermidis

<400> SEQUENCE: 16

```
Gly Arg Ser Met Leu Met Ala Lys Tyr Arg Gly Lys Pro Phe Gln Leu
1               5                  10                  15

Tyr Val Lys Leu Ser Cys Ser Thr Met Met Ala Thr Ser Ile Ile Leu
            20                  25                  30

Thr Asn Ile Leu Pro Tyr Asp Ala Gln Ala Ala Ser Glu Lys Asp Thr
        35                  40                  45

Glu Ile Thr Lys Glu Ile Leu Ser Lys Gln Asp Leu Leu Asp Lys Val
    50                  55                  60

Asp Lys Ala Ile Arg Gln Ile Glu Gln Leu Lys Gln Leu Ser Ala Ser
65                  70                  75                  80

Ser Lys Glu His Tyr Lys Ala Gln Leu Asn Glu Ala Lys Thr Ala Ser
                85                  90                  95

Gln Ile Asp Glu Ile Ile Lys Arg Ala Asn Glu Leu Asp Ser Lys Asp
            100                 105                 110

Asn Lys Ser Ser His Thr Glu Met Asn Gly Gln Ser Asp Ile Asp Ser
        115                 120                 125

Lys Leu Asp Gln Leu Leu Lys Asp Leu Asn Glu Val Ser Ser Asn Val
    130                 135                 140

Asp Arg Gly Gln Gln Ser Gly Glu Asp Leu Asn Ala Met Lys Asn
145                 150                 155                 160

Asp Met Ser Gln Thr Ala Thr Thr Lys His Gly Glu Lys Asp Asp Lys
                165                 170                 175

Asn Asp Glu Ala Met Val Asn Lys Ala Leu Glu Asp Leu Asp His Leu
            180                 185                 190

Asn Gln Gln Ile His Lys Ser Lys Asp Ala Ser Lys Asp Thr Ser Glu
        195                 200                 205

Asp Pro Ala Val Ser Thr Thr Asp Asn Asn His Glu Val Ala Lys Thr
    210                 215                 220

Pro Asn Asn Asp Gly Ser Gly His Val Val Leu Asn Lys Phe Leu Ser
225                 230                 235                 240

Asn Glu Glu Asn Gln Ser His Ser Asn Arg Leu Thr Asp Lys Leu Gln
                245                 250                 255

Gly Ser Asp Lys Ile Asn His Ala Met Ile Glu Lys Leu Ala Lys Ser
            260                 265                 270

Asn Ala Ser Thr Gln His Tyr Thr Tyr His Lys Leu Asn Thr Leu Gln
        275                 280                 285

Ser Leu Asp Gln Arg Ile Ala Asn Thr Gln Leu Pro Lys Asn Gln Lys
    290                 295                 300
```

```
Ser Asp Leu Met Ser Glu Val Asn Lys Thr Lys Glu Arg Ile Lys Ser
305                 310                 315                 320

Gln Arg Asn Ile Ile Leu Glu Leu Ala Arg Thr Asp Asp Lys Lys
            325                 330                 335

Tyr Ala Thr Gln Ser Ile Leu Glu Ser Ile Phe Asn Lys Asp Glu Ala
            340                 345                 350

Val Lys Ile Leu Lys Asp Ile Arg Val Asp Gly Lys Thr Asp Gln Gln
            355                 360                 365

Ile Ala Asp Gln Ile Thr Arg His Ile Asp Gln Leu Ser Leu Thr Thr
        370                 375                 380

Ser Asp Asp Leu Leu Thr Ser Leu Ile Asp Gln Ser Gln Asp Lys Ser
385                 390                 395                 400

Leu Leu Ile Ser Gln Ile Leu Gln Thr Lys Leu Gly Lys Ala Glu Ala
                405                 410                 415

Asp Lys Leu Ala Lys Asp Trp Thr Asn Lys Gly Leu Ser Asn Arg Gln
            420                 425                 430

Ile Val Asp Gln Leu Lys Lys His Phe Ala Ser Thr Gly Asp Thr Ser
        435                 440                 445

Ser Asp Asp Ile Leu Lys Ala Ile Leu Asn Asn Ala Lys Asp Lys Lys
450                 455                 460

Gln Ala Ile Glu Thr Ile Leu Ala Thr Arg Ile Glu Arg Gln Lys Ala
465                 470                 475                 480

Lys Leu Leu Ala Asp Leu Ile Thr Lys Ile Glu Thr Asp Gln Asn Lys
                485                 490                 495

Ile Phe Asn Leu Val Lys Ser Ala Leu Asn Gly Lys Ala Asp Asp Leu
            500                 505                 510

Leu Asn Leu Gln Lys Arg Leu Asn Gln Thr Lys Lys Asp Ile Asp Tyr
        515                 520                 525

Ile Leu Ser Pro Ile Val Asn Arg Pro Ser Leu Leu Asp Arg Leu Asn
    530                 535                 540

Lys Asn Gly Lys Thr Thr Asp Leu Asn Lys Leu Ala Asn Leu Met Asn
545                 550                 555                 560

Gln Gly Ser Asp Leu Leu Asp Ser Ile Pro Asp Ile Pro Thr Pro Lys
                565                 570                 575

Pro Glu Lys Thr Leu Thr Leu Gly Lys Gly Asn Gly Leu Leu Ser Gly
            580                 585                 590

Leu Leu Asn Ala Asp Gly Asn Val Ser Leu Pro Lys Ala Gly Glu Thr
        595                 600                 605

Ile Lys Glu His Trp Leu Pro Ile Ser Val Ile Val Gly Ala Met Gly
    610                 615                 620

Val Leu Met Ile Trp Leu Ser Arg Arg Asn Lys Leu Lys Asn Lys Ala
625                 630                 635                 640

<210> SEQ ID NO 17
<211> LENGTH: 522
<212> TYPE: PRT
<213> ORGANISM: Staphylococcus epidermidis

<400> SEQUENCE: 17

Ala Ser Glu Thr Pro Ile Thr Ser Glu Ile Ser Ser Asn Ser Glu Thr
1               5                   10                  15

Val Ala Asn Gln Asn Ser Thr Thr Ile Lys Asn Ser Gln Lys Glu Thr
            20                  25                  30

Val Asn Ser Thr Ser Leu Glu Ser Asn His Ser Asn Ser Thr Asn Lys
```

-continued

```
                35                  40                  45
Gln Met Ser Ser Glu Val Thr Asn Thr Ala Gln Ser Ser Glu Lys Ala
             50                  55                  60
Gly Ile Ser Gln Gln Ser Ser Glu Thr Ser Asn Gln Ser Ser Lys Leu
 65                  70                  75                  80
Asn Thr Tyr Ala Ser Thr Asp His Val Glu Ser Thr Ile Asn Asn
                 85                  90                  95
Asp Asn Thr Ala Gln Gln Asp Gln Asn Lys Ser Ser Asn Val Thr Ser
                100                 105                 110
Lys Ser Thr Gln Ser Asn Thr Ser Ser Glu Lys Asn Ile Ser Ser
                115                 120                 125
Asn Leu Thr Gln Ser Ile Glu Thr Lys Ala Thr Asp Ser Leu Ala Thr
            130                 135                 140
Ser Glu Ala Arg Thr Ser Thr Asn Gln Ile Ser Asn Leu Thr Ser Thr
145                 150                 155                 160
Ser Thr Ser Asn Gln Ser Ser Pro Thr Ser Phe Ala Asn Leu Arg Thr
                165                 170                 175
Phe Ser Arg Phe Thr Val Leu Asn Thr Met Ala Ala Pro Thr Thr Thr
            180                 185                 190
Ser Thr Thr Thr Thr Ser Ser Leu Thr Ser Asn Ser Val Val Val Asn
        195                 200                 205
Lys Asp Asn Phe Asn Glu His Met Asn Leu Ser Gly Ser Ala Thr Tyr
210                 215                 220
Asp Pro Lys Thr Gly Ile Ala Thr Leu Thr Pro Asp Ala Tyr Ser Gln
225                 230                 235                 240
Lys Gly Ala Ile Ser Leu Asn Thr Arg Leu Asp Ser Asn Arg Ser Phe
            245                 250                 255
Arg Phe Ile Gly Lys Val Asn Leu Gly Asn Arg Tyr Glu Gly Tyr Ser
            260                 265                 270
Pro Asp Gly Val Ala Gly Gly Asp Gly Ile Gly Phe Ala Phe Ser Pro
            275                 280                 285
Gly Pro Leu Gly Gln Ile Gly Lys Glu Gly Ala Ala Val Gly Ile Gly
290                 295                 300
Gly Leu Asn Asn Ala Phe Gly Phe Lys Leu Asp Thr Tyr His Asn Thr
305                 310                 315                 320
Ser Thr Pro Arg Ser Asp Ala Lys Ala Lys Ala Asp Pro Arg Asn Val
                325                 330                 335
Gly Gly Gly Gly Ala Phe Gly Ala Phe Val Ser Thr Asp Arg Asn Gly
            340                 345                 350
Met Ala Thr Thr Glu Glu Ser Thr Ala Ala Lys Leu Asn Val Gln Pro
            355                 360                 365
Thr Asp Asn Ser Phe Gln Asp Phe Val Ile Asp Tyr Asn Gly Asp Thr
            370                 375                 380
Lys Val Met Thr Val Thr Tyr Ala Gly Gln Thr Phe Thr Arg Asn Leu
385                 390                 395                 400
Thr Asp Trp Ile Lys Asn Ser Gly Gly Thr Thr Phe Ser Leu Ser Met
                405                 410                 415
Thr Ala Ser Thr Gly Gly Ala Lys Asn Leu Gln Gln Val Gln Phe Gly
            420                 425                 430
Thr Phe Glu Tyr Thr Glu Ser Ala Val Ala Lys Val Arg Tyr Val Asp
            435                 440                 445
Ala Asn Thr Gly Lys Asp Ile Ile Pro Pro Lys Thr Ile Ala Gly Glu
450                 455                 460
```

```
Val Asp Gly Thr Val Asn Ile Asp Lys Gln Leu Asn Asn Phe Lys Asn
465                 470                 475                 480

Leu Gly Tyr Ser Tyr Val Gly Thr Asp Ala Leu Lys Ala Pro Asn Tyr
                485                 490                 495

Thr Glu Thr Ser Gly Thr Pro Thr Leu Lys Leu Thr Asn Ser Ser Gln
            500                 505                 510

Thr Val Ile Tyr Lys Phe Lys Asp Val Gln
        515                 520

<210> SEQ ID NO 18
<211> LENGTH: 485
<212> TYPE: PRT
<213> ORGANISM: Staphylococcus epidermidis

<400> SEQUENCE: 18

Ala Ser Asp Ala Pro Leu Thr Ser Glu Leu Asn Thr Gln Ser Glu Thr
1               5                   10                  15

Val Gly Asn Gln Asn Ser Thr Thr Ile Glu Ala Ser Thr Ser Thr Ala
                20                  25                  30

Asp Ser Thr Ser Val Thr Lys Asn Ser Ser Val Gln Thr Ser Asn
            35                  40                  45

Ser Asp Thr Val Ser Ser Glu Lys Ser Glu Lys Val Thr Ser Thr Thr
50                  55                  60

Asn Ser Thr Ser Asn Gln Gln Glu Lys Leu Thr Ser Thr Ser Glu Ser
65                  70                  75                  80

Thr Ser Ser Lys Asn Thr Thr Ser Ser Asp Thr Lys Ser Val Ala
                85                  90                  95

Ser Thr Ser Ser Thr Glu Gln Pro Ile Asn Thr Ser Thr Asn Gln Ser
            100                 105                 110

Thr Ala Ser Asn Asn Thr Ser Gln Ser Thr Thr Pro Ser Ser Val Asn
            115                 120                 125

Leu Asn Lys Thr Ser Thr Thr Ser Thr Ser Thr Ala Pro Val Lys Leu
130                 135                 140

Arg Thr Phe Ser Arg Leu Ala Met Ser Thr Phe Ala Ser Ala Ala Thr
145                 150                 155                 160

Thr Thr Ala Val Thr Ala Asn Thr Ile Thr Val Asn Lys Asp Asn Leu
                165                 170                 175

Lys Gln Tyr Met Thr Thr Ser Gly Asn Ala Thr Tyr Asp Gln Ser Thr
                180                 185                 190

Gly Ile Val Thr Leu Thr Gln Asp Ala Tyr Ser Gln Lys Gly Ala Ile
            195                 200                 205

Thr Leu Gly Thr Arg Ile Asp Ser Asn Lys Ser Phe His Phe Ser Gly
210                 215                 220

Lys Val Asn Leu Gly Asn Lys Tyr Glu Gly His Gly Asn Gly Gly Asp
225                 230                 235                 240

Gly Ile Gly Phe Ala Phe Ser Pro Gly Val Leu Gly Glu Thr Gly Leu
                245                 250                 255

Asn Gly Ala Ala Val Gly Ile Gly Gly Leu Ser Asn Ala Phe Gly Phe
                260                 265                 270

Lys Leu Asp Thr Tyr His Asn Thr Ser Lys Pro Asn Ser Ala Ala Lys
            275                 280                 285

Ala Asn Ala Asp Pro Ser Asn Val Ala Gly Gly Ala Phe Gly Ala
            290                 295                 300

Phe Val Thr Thr Asp Ser Tyr Gly Val Ala Thr Thr Tyr Thr Ser Ser
```

```
        305                 310                 315                 320
Ser Thr Ala Asp Asn Ala Ala Lys Leu Asn Val Gln Pro Thr Asn Asn
                325                 330                 335

Thr Phe Gln Asp Phe Asp Ile Asn Tyr Asn Gly Asp Thr Lys Val Met
            340                 345                 350

Thr Val Lys Tyr Ala Gly Gln Thr Trp Thr Arg Asn Ile Ser Asp Trp
        355                 360                 365

Ile Ala Lys Ser Gly Thr Thr Asn Phe Ser Leu Ser Met Thr Ala Ser
    370                 375                 380

Thr Gly Gly Ala Thr Asn Leu Gln Gln Val Gln Phe Gly Thr Phe Glu
385                 390                 395                 400

Tyr Thr Glu Ser Ala Val Thr Gln Val Arg Tyr Val Asp Val Thr Thr
                405                 410                 415

Gly Lys Asp Ile Ile Pro Pro Lys Thr Tyr Ser Gly Asn Val Asp Gln
            420                 425                 430

Val Val Thr Ile Asp Asn Gln Ser Ala Leu Thr Ala Lys Gly Tyr
        435                 440                 445

Asn Tyr Thr Ser Val Asp Ser Ser Tyr Ala Ser Thr Tyr Asn Asp Thr
    450                 455                 460

Asn Lys Thr Val Lys Met Thr Asn Ala Gly Gln Ser Val Thr Tyr Tyr
465                 470                 475                 480

Phe Thr Asp Val Val
                485

<210> SEQ ID NO 19
<211> LENGTH: 1245
<212> TYPE: PRT
<213> ORGANISM: Staphylococcus epidermidis

<400> SEQUENCE: 19

Met Gly Lys Arg Arg Gln Gly Pro Ile Asn Lys Val Asp Phe Leu
1               5                   10                  15

Pro Asn Lys Leu Asn Lys Tyr Ser Ile Arg Lys Phe Thr Val Gly Thr
            20                  25                  30

Ala Ser Ile Leu Leu Gly Ser Thr Leu Ile Phe Gly Ser Ser Ser His
        35                  40                  45

Glu Ala Lys Ala Ala Glu Glu Lys Gln Val Asp Pro Ile Thr Gln Ala
    50                  55                  60

Asn Gln Asn Asp Ser Ser Glu Arg Ser Leu Glu Asn Thr Asn Gln Pro
65                  70                  75                  80

Thr Val Asn Asn Glu Ala Pro Gln Met Ser Ser Thr Leu Gln Ala Glu
                85                  90                  95

Glu Gly Ser Asn Ala Glu Ala Pro Gln Ser Glu Pro Thr Lys Ala Glu
            100                 105                 110

Glu Gly Gly Asn Ala Glu Ala Ala Gln Ser Glu Pro Thr Lys Ala Glu
        115                 120                 125

Glu Gly Gly Asn Ala Glu Ala Pro Gln Ser Glu Pro Thr Lys Ala Glu
    130                 135                 140

Glu Gly Gly Asn Ala Glu Ala Ala Gln Ser Glu Pro Thr Lys Thr Glu
145                 150                 155                 160

Glu Gly Ser Asn Val Lys Ala Ala Gln Ser Glu Pro Thr Lys Ala Glu
                165                 170                 175

Glu Gly Ser Asn Ala Glu Ala Pro Gln Ser Glu Pro Thr Lys Thr Glu
            180                 185                 190
```

```
Glu Gly Ser Asn Ala Lys Ala Ala Gln Ser Glu Pro Thr Lys Ala Glu
            195                 200                 205

Glu Gly Gly Asn Ala Glu Ala Ala Gln Ser Glu Pro Thr Lys Thr Glu
            210                 215                 220

Glu Gly Ser Asn Ala Glu Ala Pro Gln Ser Glu Pro Thr Lys Ala Glu
225                 230                 235                 240

Glu Gly Gly Asn Ala Glu Ala Pro Gln Ser Glu Pro Thr Lys Thr Glu
            245                 250                 255

Glu Gly Gly Asn Ala Glu Ala Pro Asn Val Pro Thr Ile Lys Ala Asn
            260                 265                 270

Ser Asp Asn Asp Thr Gln Thr Gln Phe Ser Glu Ala Pro Thr Arg Asn
            275                 280                 285

Asp Leu Ala Arg Lys Glu Asp Ile Pro Ala Val Ser Lys Asn Glu Glu
            290                 295                 300

Leu Gln Ser Ser Gln Pro Asn Thr Asp Ser Lys Ile Glu Pro Thr Thr
305                 310                 315                 320

Ser Glu Pro Val Asn Leu Asn Tyr Ser Ser Pro Phe Met Ser Leu Leu
            325                 330                 335

Ser Met Pro Ala Asp Ser Ser Ser Asn Asn Thr Lys Asn Thr Ile Asp
            340                 345                 350

Ile Pro Pro Thr Thr Val Lys Gly Arg Asp Asn Tyr Asp Phe Tyr Gly
            355                 360                 365

Arg Val Asp Ile Glu Ser Asn Pro Thr Asp Leu Asn Ala Thr Asn Leu
            370                 375                 380

Thr Arg Tyr Asn Tyr Gly Gln Pro Pro Gly Thr Thr Thr Ala Gly Ala
385                 390                 395                 400

Val Gln Phe Lys Asn Gln Val Ser Phe Asp Lys Asp Phe Asp Phe Asn
            405                 410                 415

Ile Arg Val Ala Asn Asn Arg Gln Ser Asn Thr Thr Gly Ala Asp Gly
            420                 425                 430

Trp Gly Phe Met Phe Ser Lys Lys Asp Gly Asp Phe Leu Lys Asn
            435                 440                 445

Gly Gly Ile Leu Arg Glu Lys Gly Thr Pro Ser Ala Ala Gly Phe Arg
            450                 455                 460

Ile Asp Thr Gly Tyr Tyr Asn Asn Asp Pro Leu Asp Lys Ile Gln Lys
465                 470                 475                 480

Gln Ala Gly Gln Gly Tyr Arg Gly Tyr Gly Thr Phe Val Lys Asn Asp
            485                 490                 495

Ser Gln Gly Asn Thr Ser Lys Val Gly Ser Gly Thr Pro Ser Thr Asp
            500                 505                 510

Phe Leu Asn Tyr Ala Asp Asn Thr Thr Asn Asp Leu Asp Gly Lys Phe
            515                 520                 525

His Gly Gln Lys Leu Asn Asn Val Asn Leu Lys Tyr Asn Ala Ser Asn
            530                 535                 540

Gln Thr Phe Thr Ala Thr Tyr Ala Gly Lys Thr Trp Thr Ala Thr Leu
545                 550                 555                 560

Ser Glu Leu Gly Leu Ser Pro Thr Asp Ser Tyr Asn Phe Leu Val Thr
            565                 570                 575

Ser Ser Gln Tyr Gly Asn Gly Asn Ser Gly Thr Tyr Ala Ser Gly Val
            580                 585                 590

Met Arg Ala Asp Leu Asp Gly Ala Thr Leu Thr Tyr Thr Pro Lys Ala
            595                 600                 605

Val Asp Gly Asp Pro Ile Ile Ser Thr Lys Glu Ile Pro Phe Asn Lys
```

-continued

```
            610                 615                 620
Lys Arg Glu Phe Asp Pro Asn Leu Ala Pro Gly Thr Glu Lys Val Val
625                 630                 635                 640

Gln Lys Gly Glu Pro Gly Ile Glu Thr Thr Thr Pro Thr Tyr Val
                645                 650                 655

Asn Pro Asn Thr Gly Glu Lys Val Gly Glu Glu Pro Thr Glu Lys
                660                 665                 670

Ile Thr Lys Gln Pro Val Asp Glu Ile Val His Tyr Gly Gly Glu
                675                 680                 685

Ile Lys Pro Gly His Lys Asp Glu Phe Asp Pro Asn Ala Pro Lys Gly
690                 695                 700

Ser Gln Thr Thr Gln Pro Gly Lys Pro Val Lys Asn Pro Asp Thr
705                 710                 715                 720

Gly Glu Val Val Thr Pro Val Asp Val Thr Lys Tyr Gly Pro
                725                 730                 735

Val Asp Gly Asp Pro Ile Thr Ser Glu Glu Ile Pro Phe Asp Lys
                740                 745                 750

Lys Arg Glu Phe Asn Pro Asp Leu Lys Pro Gly Glu Glu Arg Val Lys
                755                 760                 765

Gln Lys Gly Glu Pro Gly Thr Lys Thr Ile Thr Thr Pro Thr Lys
770                 775                 780

Asn Pro Leu Thr Gly Glu Lys Val Gly Glu Gly Pro Thr Glu Lys
785                 790                 795                 800

Ile Thr Lys Gln Pro Val Asp Glu Ile Thr Glu Tyr Gly Gly Glu Glu
                805                 810                 815

Ile Lys Pro Gly His Lys Asp Glu Phe Asp Pro Asn Ala Pro Lys Gly
                820                 825                 830

Ser Gln Glu Asp Val Pro Gly Lys Pro Gly Val Lys Asn Pro Gly Thr
                835                 840                 845

Gly Glu Val Val Thr Pro Val Asp Asp Val Thr Lys Tyr Gly Pro
                850                 855                 860

Val Asp Gly Asp Pro Ile Thr Ser Thr Glu Glu Ile Pro Phe Asp Lys
865                 870                 875                 880

Lys Arg Glu Phe Asn Pro Asp Leu Lys Pro Gly Glu Glu Arg Val Lys
                885                 890                 895

Gln Lys Gly Glu Pro Gly Thr Lys Thr Ile Thr Thr Pro Thr Thr Lys
                900                 905                 910

Asn Pro Leu Thr Gly Glu Lys Val Gly Glu Gly Pro Thr Glu Lys
                915                 920                 925

Ile Thr Lys Gln Pro Val Asp Glu Ile Val His Tyr Gly Gly Glu Gln
                930                 935                 940

Ile Pro Gln Gly His Lys Asp Glu Phe Asp Pro Asn Ala Pro Val Asp
945                 950                 955                 960

Ser Lys Thr Glu Val Pro Gly Lys Pro Gly Val Lys Asn Pro Asp Thr
                965                 970                 975

Gly Glu Val Val Thr Pro Pro Val Asp Asp Val Thr Lys Tyr Gly Pro
                980                 985                 990

Val Asp Gly Asp Ser Ile Thr Ser Thr Glu Glu Ile Pro Phe Asp Lys
                995                 1000                1005

Lys Arg Glu Phe Asp Pro Asn Leu Ala Pro Gly Thr Glu Lys Val
                1010                1015                1020

Val Gln Lys Gly Glu Pro Gly Thr Lys Thr Ile Thr Thr Pro Thr
                1025                1030                1035
```

```
Thr Lys Asn Pro Leu Thr Gly Glu Lys Val Gly Glu Gly Lys Ser
    1040              1045                1050
Thr Glu Lys Val Thr Lys Gln Pro Val Asp Glu Ile Val Glu Tyr
    1055              1060                1065
Gly Pro Thr Lys Ala Glu Pro Gly Lys Pro Ala Glu Pro Gly Lys
    1070              1075                1080
Pro Ala Glu Pro Gly Lys Pro Ala Glu Pro Gly Thr Pro Ala Glu
    1085              1090                1095
Pro Gly Lys Pro Ala Glu Pro Gly Thr Pro Ala Glu Pro Gly Lys
    1100              1105                1110
Pro Ala Glu Pro Gly Lys Pro Ala Glu Pro Gly Lys Pro Ala Glu
    1115              1120                1125
Pro Gly Lys Pro Ala Glu Pro Gly Thr Pro Ala Glu Pro Gly Thr
    1130              1135                1140
Pro Ala Glu Pro Gly Lys Pro Ala Glu Pro Gly Thr Pro Ala Glu
    1145              1150                1155
Pro Gly Lys Pro Ala Glu Pro Gly Thr Pro Ala Glu Pro Gly Lys
    1160              1165                1170
Pro Ala Glu Ser Gly Lys Pro Val Glu Pro Gly Thr Pro Ala Gln
    1175              1180                1185
Ser Gly Ala Pro Glu Gln Pro Asn Arg Ser Met His Ser Thr Asp
    1190              1195                1200
Asn Lys Asn Gln Leu Pro Asp Thr Gly Glu Asn Arg Gln Ala Asn
    1205              1210                1215
Glu Gly Thr Leu Val Gly Ser Leu Leu Ala Ile Val Gly Ser Leu
    1220              1225                1230
Phe Ile Phe Gly Arg Arg Lys Lys Gly Asn Glu Lys
    1235              1240                1245

<210> SEQ ID NO 20
<211> LENGTH: 3765
<212> TYPE: DNA
<213> ORGANISM: Staphylococcus epidermidis

<400> SEQUENCE: 20
atgggcaaac gtagacaagg tcctattaat aaaaaagtgg attttttacc taacaaatta      60
aacaagtatt ctataagaaa attcactgtt ggtacggcct caatattact tggttcgaca     120
cttatttttg gaagtagtag ccatgaagcg aaagctgcag aagaaaaaca agttgatcca     180
attacacaag ctaatcaaaa tgatagtagt gaaagatcac ttgaaaacac aaatcaacct     240
actgtaaaca atgaagcacc acagatgtct tctacattgc aagcagaaga aggaagcaat     300
gcagaagcac ctcaatctga gccaacgaag gcagaagaag gaggcaatgc agaagcagct     360
caatctgagc caacgaaggc agaagaagga ggcaatgcag aagcacctca atctgagcca     420
acgaaggcag aagaaggagg caatgcagaa gcagctcaat ctgagccaac gaagacagaa     480
gaaggaagca acgtaaaagc agctcaatct gagccaacga aggcagaaga aggaagcaat     540
gcagaagcac ctcaatctga gccaacgaag acagaagaag gaagcaacgc aaaagcagct     600
caatctgagc caacgaaggc agaagaagga ggcaatgcag aagcagctca atctgagcca     660
acgaagacag aagaaggaag caatgcagaa gcacctcaat ctgagccaac gaaggcagaa     720
gaaggaggca atgcagaagc acctcaatct gagccaacga agacagaaga aggaggcaat     780
gcagaagcac cgaatgttcc aactatcaaa gctaattcag ataatgatac acaaacacaa     840
```

-continued

```
ttttcagaag cccctacaag aaatgaccta gctagaaaag aagatatccc tgctgtttct    900
aaaaacgagg aattacaatc atcacaacca aacactgaca gtaaaataga acctacaact    960
tcagaacctg tgaatttaaa ttatagttct ccgtttatgt ccttattaag catgcctgct   1020
gatagttcat ccaataacac taaaaataca atagatatac cgccaactac ggttaaaggt   1080
agagataatt acgatttta cggtagagta gatatcgaaa gtaatcctac agatttaaat   1140
gcgacaaatt taacgagata taattatgga cagccacctg gtacaacaac agctggtgca   1200
gttcaattta aaaatcaagt tagttttgat aaagatttcg actttaacat tagagtagca   1260
aacaatcgtc aaagtaatac aactggtgca gatggttggg gctttatgtt cagcaagaaa   1320
gatggggatg atttcctaaa aaacggtggt atcttacgtg aaaaaggtac acctagtgca   1380
gctggtttca gaattgatac aggatattat aataacgatc cattagataa aatacagaaa   1440
caagctggtc aaggctatag agggtatggg acatttgtta aaaatgactc ccaaggtaat   1500
acttctaaag taggatcagg tactccatca acagattttc ttaactacgc agataatact   1560
actaatgatt tagatggtaa attccatggt caaaaattaa ataatgttaa tttgaaatat   1620
aatgcttcaa atcaaacttt tacagctact tatgctggta aaacttggac ggctacgtta   1680
tctgaattag gattgagtcc aactgatagt tacaattttt tagttacatc aagtcaatat   1740
ggaaatggta atagtggtac atacgcaagt ggcgttatga gagctgattt agatggtgca   1800
acattgacat acactcctaa agcagtcgat ggagatccaa ttatatcaac taaggaaata   1860
ccatttaata gaaacgtgaa atttgatcca aacttagccc caggtacaga aaagtagtc    1920
caaaaaggtg aaccaggaat tgaaacaaca acaacaccaa cttatgtcaa tcctaataca   1980
ggagaaaaag ttggcgaagg tgaaccaaca gaaaaaataa caaaacaacc agtggatgaa   2040
atcgttcatt atggtggcga agaaatcaag ccaggccata aggatgaatt tgatccaaat   2100
gcaccgaaag gtagtcaaac aacgcaacca ggtaagccgg gggttaaaaa tcctgataca   2160
ggcgaagtag ttactccacc tgtggatgat gtgacaaaat atggtccagt tgatggagat   2220
ccgatcacgt caacggaaga aattccattc gacaagaaac gtgaattcaa tcctgattta   2280
aaaccaggtg aagagcgtgt taaacaaaaa ggtgaaccag gaacaaaaac aattacaaca   2340
ccaacaacta gaacccatt aacagggaa aaagttggcg aagtgaacc aacagaaaaa   2400
ataacaaaac aaccagtaga tgaaatcaca gaatatggtg gcgaagaaat caagccaggc   2460
cataaggatg aatttgatcc aaatgcaccg aaaggtagcc aagaggacgt tccaggtaaa   2520
ccaggagtta aaaaccctgg aacaggcgaa gtagtcacac caccagtgga tgatgtgaca   2580
aaatatggtc cagttgatgg agatccgatc acgtcaacgg aagaaattcc attcgacaag   2640
aaacgtgaat caatcctga tttaaaacca ggtgaagagc gcgttaaaca gaaaggtgaa   2700
ccaggaacaa aaacaattac aacgccaaca actaagaacc cattaacagg agaaaaagtt   2760
ggcgaaggtg aaccaacaga aaaataaca aacaaccag tggatgagat tgttcattat   2820
ggtggtgaac aaataccaca aggtcataaa gatgaatttg atccaaatgc acctgtagat   2880
agtaaaactg aagttccagg taaccaggga gttaaaaatc ctgatacagg tgaagttgtt   2940
accccaccag tggatgatgt gacaaaatat ggtccagttg atggagattc gattacgtca   3000
acggaagaaa ttccgtttga taaaaacgc gaatttgatc caaacttagc gccaggtaca   3060
gagaaagtcg ttcaaaaagg tgaaccagga acaaaaacaa ttacaacgcc aacaactaag   3120
aacccattaa caggagaaaa agttggcgaa ggtaaatcaa cagaaaaagt cactaaacaa   3180
cctgttgacg aaaattgttga gtatggtcca acaaaagcag aaccaggtaa accagcggaa   3240
```

```
ccaggtaaac cagcggaacc aggtaaacca gcggaaccag gtacgccagc agaaccaggt    3300
aaaccagcgg aaccaggtac gccagcagaa ccaggtaaac cagcggaacc aggtaaacca    3360
gcggaaccag gtaaaccagc ggaaccaggt aaaccagcgg aaccaggtac gccagcagaa    3420
ccaggtacgc cagcagaacc aggtaaacca gcggaaccag gtacgccagc agaaccaggt    3480
aaaccagcgg aaccaggtac gccagcagaa ccaggtaaac cagcggaatc aggtaaacca    3540
gtggaaccag gtacgccagc acaatcaggt gcaccagaac aaccaaatag atcaatgcat    3600
tcaacagata ataaaaatca attacctgat acaggtgaaa atcgtcaagc taatgaggga    3660
actttagtcg gatctctatt agcaattgtc ggatcattgt tcatatttgg tcgtcgtaaa    3720
aaaggtaatg aaaaataatt tcatataaaa actttctgcc attaa                   3765
```

<210> SEQ ID NO 21
<211> LENGTH: 546
<212> TYPE: PRT
<213> ORGANISM: Staphylococcus epidermidis

<400> SEQUENCE: 21

```
Glu Lys Gln Val Asp Pro Ile Thr Gln Ala Asn Gln Asn Asp Ser Ser
1               5                   10                  15

Glu Arg Ser Leu Glu Asn Thr Asn Gln Pro Thr Val Asn Asn Glu Ala
            20                  25                  30

Pro Gln Met Ser Ser Thr Leu Gln Ala Glu Glu Gly Ser Asn Ala Glu
        35                  40                  45

Ala Pro Gln Ser Glu Pro Thr Lys Ala Glu Glu Gly Gly Asn Ala Glu
    50                  55                  60

Ala Ala Gln Ser Glu Pro Thr Lys Ala Glu Glu Gly Gly Asn Ala Glu
65                  70                  75                  80

Ala Pro Gln Ser Glu Pro Thr Lys Ala Glu Glu Gly Gly Asn Ala Glu
                85                  90                  95

Ala Ala Gln Ser Glu Pro Thr Lys Thr Glu Glu Gly Ser Asn Val Lys
            100                 105                 110

Ala Ala Gln Ser Glu Pro Thr Lys Ala Glu Glu Gly Ser Asn Ala Glu
        115                 120                 125

Ala Pro Gln Ser Glu Pro Thr Lys Thr Glu Glu Gly Ser Asn Ala Lys
    130                 135                 140

Ala Ala Gln Ser Glu Pro Thr Lys Ala Glu Glu Gly Gly Asn Ala Glu
145                 150                 155                 160

Ala Ala Gln Ser Glu Pro Thr Lys Thr Glu Glu Gly Ser Asn Ala Glu
                165                 170                 175

Ala Pro Gln Ser Glu Pro Thr Lys Ala Glu Glu Gly Gly Asn Ala Glu
            180                 185                 190

Ala Pro Gln Ser Glu Pro Thr Lys Thr Glu Glu Gly Gly Asn Ala Glu
        195                 200                 205

Ala Pro Asn Val Pro Thr Ile Lys Ala Asn Ser Asp Asn Asp Thr Gln
    210                 215                 220

Thr Gln Phe Ser Glu Ala Pro Thr Arg Asn Asp Leu Ala Arg Lys Glu
225                 230                 235                 240

Asp Ile Pro Ala Val Ser Lys Asn Glu Glu Leu Gln Ser Ser Gln Pro
                245                 250                 255

Asn Thr Asp Ser Lys Ile Glu Pro Thr Thr Ser Glu Pro Val Asn Leu
            260                 265                 270

Asn Tyr Ser Ser Pro Phe Met Ser Leu Leu Ser Met Pro Ala Asp Ser
```

```
                  275                 280                 285
Ser Ser Asn Asn Thr Lys Asn Thr Ile Asp Ile Pro Thr Thr Val
    290                 295                 300

Lys Gly Arg Asp Asn Tyr Asp Phe Tyr Gly Arg Val Asp Ile Glu Ser
305                 310                 315                 320

Asn Pro Thr Asp Leu Asn Ala Thr Asn Leu Thr Arg Tyr Asn Tyr Gly
                325                 330                 335

Gln Pro Pro Gly Thr Thr Ala Gly Ala Val Gln Phe Lys Asn Gln
                340                 345                 350

Val Ser Phe Asp Lys Asp Phe Asp Phe Asn Ile Arg Val Ala Asn Asn
    355                 360                 365

Arg Gln Ser Asn Thr Thr Gly Ala Asp Gly Trp Gly Phe Met Phe Ser
    370                 375                 380

Lys Lys Asp Gly Asp Asp Phe Leu Lys Asn Gly Ile Leu Arg Glu
385                 390                 395                 400

Lys Gly Thr Pro Ser Ala Ala Gly Phe Arg Ile Asp Thr Gly Tyr Tyr
                405                 410                 415

Asn Asn Asp Pro Leu Asp Lys Ile Gln Lys Gln Ala Gly Gln Gly Tyr
                420                 425                 430

Arg Gly Tyr Gly Thr Phe Val Lys Asn Asp Ser Gln Gly Asn Thr Ser
                435                 440                 445

Lys Val Gly Ser Gly Thr Pro Ser Thr Asp Phe Leu Asn Tyr Ala Asp
    450                 455                 460

Asn Thr Thr Asn Asp Leu Asp Gly Lys Phe His Gly Gln Lys Leu Asn
465                 470                 475                 480

Asn Val Asn Leu Lys Tyr Asn Ala Ser Asn Gln Thr Phe Thr Ala Thr
                485                 490                 495

Tyr Ala Gly Lys Thr Trp Thr Ala Thr Leu Ser Glu Leu Gly Leu Ser
                500                 505                 510

Pro Thr Asp Ser Tyr Asn Phe Leu Val Thr Ser Ser Gln Tyr Gly Asn
                515                 520                 525

Gly Asn Ser Gly Thr Tyr Ala Ser Gly Val Met Arg Ala Asp Leu Asp
    530                 535                 540

Gly Ala
545

<210> SEQ ID NO 22
<211> LENGTH: 36
<212> TYPE: PRT
<213> ORGANISM: Staphylococcus aureus

<400> SEQUENCE: 22

Leu Pro Asn Thr Gly Ser Glu Glu Met Asp Leu Pro Leu Lys Glu Leu
1               5                   10                  15

Ala Leu Ile Thr Gly Ala Ala Leu Leu Ala Arg Arg Arg Ser Lys Lys
                20                  25                  30

Glu Lys Glu Ser
        35

<210> SEQ ID NO 23
<211> LENGTH: 43
<212> TYPE: PRT
<213> ORGANISM: Staphylococcus aureus

<400> SEQUENCE: 23

Leu Pro Asp Thr Gly Asp Ser Ile Lys Gln Asn Gly Leu Leu Gly Gly
```

```
                1               5                  10                 15
            Val Met Thr Leu Leu Val Gly Leu Gly Leu Met Lys Arg Lys Lys Lys
                            20                 25                 30

Lys Asp Glu Asn Asp Gln Asp Ser Gln Ala
                        35                  40

<210> SEQ ID NO 24
<211> LENGTH: 35
<212> TYPE: PRT
<213> ORGANISM: Staphylococcus aureus

<400> SEQUENCE: 24

Leu Pro Lys Thr Gly Glu Thr Ser Ser Gln Ser Trp Trp Gly Leu
1               5                  10                 15

Tyr Ala Leu Leu Gly Met Leu Ala Leu Phe Ile Pro Lys Phe Arg Lys
                20                 25                 30

Glu Ser Lys
        35

<210> SEQ ID NO 25
<211> LENGTH: 38
<212> TYPE: PRT
<213> ORGANISM: Staphylococcus aureus

<400> SEQUENCE: 25

Leu Pro Lys Thr Gly Leu Thr Ser Val Asp Asn Phe Ile Ser Thr Val
1               5                  10                 15

Ala Phe Ala Thr Leu Ala Leu Leu Gly Ser Leu Ser Leu Leu Leu Phe
                20                 25                 30

Lys Arg Lys Glu Ser Lys
        35

<210> SEQ ID NO 26
<211> LENGTH: 36
<212> TYPE: PRT
<213> ORGANISM: Staphylococcus aureus

<400> SEQUENCE: 26

Leu Pro Gln Thr Gly Glu Glu Ser Asn Lys Asp Met Thr Leu Pro Leu
1               5                  10                 15

Met Ala Leu Ile Ala Leu Ser Ser Ile Val Ala Phe Val Leu Pro Arg
                20                 25                 30

Lys Arg Lys Asn
        35

<210> SEQ ID NO 27
<211> LENGTH: 34
<212> TYPE: PRT
<213> ORGANISM: Staphylococcus aureus

<400> SEQUENCE: 27

Leu Pro Lys Thr Gly Thr Asn Gln Ser Ser Ser Pro Glu Ala Met Phe
1               5                  10                 15

Val Leu Leu Ala Gly Ile Gly Leu Ile Ala Thr Val Arg Arg Arg Lys
                20                 25                 30

Ala Ser

<210> SEQ ID NO 28
<211> LENGTH: 33
<212> TYPE: PRT
```

-continued

```
<213> ORGANISM: Staphylococcus aureus

<400> SEQUENCE: 28

Leu Pro Lys Thr Gly Leu Glu Ser Thr Gln Lys Gly Leu Ile Phe Ser
1               5                   10                  15

Ser Ile Ile Gly Ile Ala Gly Leu Met Leu Leu Ala Arg Arg Arg Lys
            20                  25                  30

Asn

<210> SEQ ID NO 29
<211> LENGTH: 39
<212> TYPE: PRT
<213> ORGANISM: Staphylococcus aureus

<400> SEQUENCE: 29

Leu Pro Lys Ala Gly Glu Thr Ile Lys Glu His Trp Leu Pro Ile Ser
1               5                   10                  15

Val Ile Val Gly Ala Met Gly Val Leu Met Ile Trp Leu Ser Arg Arg
            20                  25                  30

Asn Lys Leu Lys Asn Lys Ala
            35
```